(12) United States Patent
Kadoma et al.

(10) Patent No.: US 11,665,960 B2
(45) Date of Patent: May 30, 2023

(54) ORGANIC COMPOUND, LIGHT-EMITTING ELEMENT, LIGHT-EMITTING DEVICE, ELECTRONIC DEVICE, AND LIGHTING DEVICE

(71) Applicant: SEMICONDUCTOR ENERGY LABORATORY CO., LTD., Atsugi (JP)

(72) Inventors: Hiroshi Kadoma, Kanagawa (JP); Hiroki Suzuki, Aichi (JP); Yusuke Takita, Kanagawa (JP); Tsunenori Suzuki, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 735 days.

(21) Appl. No.: 16/483,304

(22) PCT Filed: Jan. 26, 2018

(86) PCT No.: PCT/IB2018/050474
§ 371 (c)(1),
(2) Date: Aug. 2, 2019

(87) PCT Pub. No.: WO2018/146570
PCT Pub. Date: Aug. 16, 2018

(65) Prior Publication Data
US 2020/0028095 A1 Jan. 23, 2020

(30) Foreign Application Priority Data
Feb. 9, 2017 (JP) ............................. JP2017-022299

(51) Int. Cl.
*H01L 51/00* (2006.01)
*C07D 209/86* (2006.01)
(Continued)

(52) U.S. Cl.
CPC ........ *H01L 51/0072* (2013.01); *C07D 209/86* (2013.01); *C09K 11/06* (2013.01);
(Continued)

(58) Field of Classification Search
CPC ..... H01L 27/32; H01L 51/50; H01L 51/0072; H01L 51/0052; H01L 27/3248; H01L 51/5012; H01L 51/5016; H01L 51/5056; H01L 51/5072; H01L 51/5088; H01L 51/5092; H05B 33/02; H05B 33/14; C07D 209/86; C07D 209/82; C09K 11/06; C09K 2211/1018; C09K 2211/1029
USPC ....................................................... 428/690
See application file for complete search history.

(56) References Cited

U.S. PATENT DOCUMENTS 7,723,722 B2 * 5/2010 Kawakami ............. H01L 51/56
428/917
8,040,047 B2 10/2011 Ushikubo et al.
(Continued)

FOREIGN PATENT DOCUMENTS

| CN | 101270075 A | 9/2008 |
| CN | 101399315 A | 4/2009 |

(Continued)

OTHER PUBLICATIONS

CAS reg. No. 2242390-21-0, Aug. 31, 2018. (Year: 2018).*
International Search Report (Application No. PCT/IB2018/050474) dated Mar. 27, 2018.
Written Opinion (Application No. PCT/IB2018/050474) dated Mar. 27, 2018.

*Primary Examiner* — Douglas J McGinty
(74) *Attorney, Agent, or Firm* — Fish & Richardson P.C.

(57) ABSTRACT

A novel organic compound is provided. That is, a novel organic compound that is effective in improving element characteristics and reliability is provided.
The organic compound includes an anthracene skeleton and a carbazole skeleton, and is represented by the following general formula (G1).

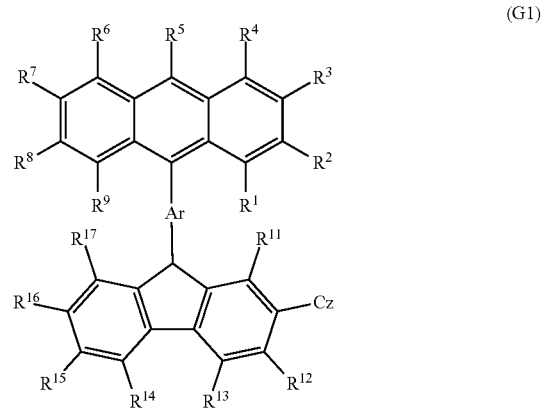

(G1)

(In the formula, Ar represents a substituted or unsubstituted arylene group having 6 to 13 carbon atoms, and when the arylene group has substituents, the substituents may be bonded to each other to form a ring. Furthermore, Cz represents a substituted or unsubstituted carbazole skeleton. Furthermore, each of $R^1$ to $R^9$ and $R^{11}$ to $R^{17}$ independently represents any of hydrogen, a substituted or unsubstituted alkyl group having 1 to 6 carbon atoms, a substituted or unsubstituted cycloalkyl group having 3 to 6 carbon atoms, or a substituted or unsubstituted aryl group having 6 to 13 carbon atoms. Furthermore, at least one of the following pairs may form a fused ring: $R^{12}$ and $R^{13}$; $R^{14}$ and $R^{15}$; $R^{15}$ and $R^{16}$; or $R^{16}$ and $R^{17}$.

13 Claims, 29 Drawing Sheets

(51) Int. Cl.
  *C09K 11/06* (2006.01)
  *H01L 27/32* (2006.01)
  *H01L 51/50* (2006.01)

(52) U.S. Cl.
  CPC .. *H01L 51/0052* (2013.01); *C09K 2211/1018* (2013.01); *H01L 27/3248* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | |
|---|---|---|---|
| 8,134,147 B2 | 3/2012 | Kawakami et al. | |
| 8,231,942 B2 | 7/2012 | Shitagaki et al. | |
| 8,251,765 B2 * | 8/2012 | Ushikubo | H01L 51/0052 313/503 |
| 8,278,655 B2 | 10/2012 | Kawakami et al. | |
| 8,283,856 B2 * | 10/2012 | Ushikubo | H01L 51/5036 313/506 |
| 8,518,492 B2 | 8/2013 | Shitagaki et al. | |
| 8,530,672 B2 | 9/2013 | Kawakami et al. | |
| 8,664,849 B2 * | 3/2014 | Ushikubo | H01L 51/5056 313/504 |
| 8,816,098 B2 * | 8/2014 | Kawakami | C07D 403/14 548/440 |
| 8,845,926 B2 | 9/2014 | Shitagaki et al. | |
| 9,136,479 B2 | 9/2015 | Kawakami et al. | |
| 9,685,623 B2 | 6/2017 | Ushikubo | |
| 10,115,926 B2 | 10/2018 | Ushikubo | |
| 10,361,379 B2 | 7/2019 | Hanaki et al. | |
| 2007/0267969 A1 | 11/2007 | Nakashima et al. | |
| 2008/0107918 A1 | 5/2008 | Egawa et al. | |
| 2008/0114178 A1 | 5/2008 | Kawakami et al. | |
| 2008/0242871 A1 * | 10/2008 | Kawakami | H01L 51/56 548/440 |
| 2009/0015140 A1 | 1/2009 | Kawakami et al. | |
| 2009/0058261 A1 | 3/2009 | Kawakami et al. | |
| 2009/0085479 A1 * | 4/2009 | Ushikubo | H01L 51/5036 313/506 |
| 2009/0102366 A1 * | 4/2009 | Ushikubo | H01L 51/5036 257/E33.044 |
| 2009/0253916 A1 | 10/2009 | Kawakami et al. | |
| 2009/0267498 A1 | 10/2009 | Kawakami et al. | |
| 2009/0284139 A1 * | 11/2009 | Ushikubo | H01L 51/5036 313/504 |
| 2009/0317539 A1 | 12/2009 | Shitagaki et al. | |
| 2010/0069647 A1 | 3/2010 | Suzuki et al. | |
| 2010/0076201 A1 | 3/2010 | Suzuki et al. | |
| 2010/0200847 A1 | 8/2010 | Kawakami et al. | |
| 2011/0050118 A1 | 3/2011 | Egawa et al. | |
| 2012/0007066 A1 | 1/2012 | Kawakami et al. | |
| 2012/0104370 A1 | 5/2012 | Suzuki et al. | |
| 2012/0104379 A1 | 5/2012 | Kawakami et al. | |
| 2012/0309984 A1 | 12/2012 | Kawakami et al. | |
| 2013/0005067 A1 | 1/2013 | Kawakami et al. | |
| 2013/0020561 A1 | 1/2013 | Suzuki et al. | |
| 2013/0323870 A1 | 12/2013 | Kawakami et al. | |
| 2014/0081031 A1 | 3/2014 | Kawakami et al. | |
| 2014/0159011 A1 | 6/2014 | Suzuki et al. | |
| 2014/0187791 A1 * | 7/2014 | Suzuki | C07D 209/88 548/440 |
| 2014/0339524 A1 | 11/2014 | Shitagaki et al. | |
| 2014/0364626 A1 | 12/2014 | Nakashima et al. | |
| 2015/0004731 A1 | 1/2015 | Kawakami et al. | |
| 2015/0053933 A1 | 2/2015 | Lee et al. | |
| 2015/0171347 A1 | 6/2015 | Suzuki et al. | |
| 2015/0249220 A1 | 9/2015 | Osaka et al. | |
| 2016/0072075 A1 | 3/2016 | Lee | |
| 2016/0126463 A1 | 5/2016 | Kadoma et al. | |
| 2016/0233437 A1 | 8/2016 | Suzuki et al. | |
| 2016/0351830 A1 | 12/2016 | Hanaki et al. | |
| 2017/0098776 A1 | 4/2017 | Nakashima et al. | |
| 2017/0125703 A1 | 5/2017 | Suzuki et al. | |
| 2017/0125704 A1 | 5/2017 | Suzuki et al. | |
| 2017/0250346 A1 | 8/2017 | Seo et al. | |
| 2018/0026207 A1 | 1/2018 | Takeda et al. | |
| 2019/0058145 A1 * | 2/2019 | Ushikubo | H01L 51/5056 |
| 2021/0242409 A1 * | 8/2021 | Seo | H01L 51/0072 |

FOREIGN PATENT DOCUMENTS

| | | |
|---|---|---|
| CN | 101414665 A | 4/2009 |
| EP | 1972619 A | 9/2008 |
| EP | 2051310 A | 4/2009 |
| JP | 2007-234651 A | 9/2007 |
| JP | 2008-266309 A | 11/2008 |
| JP | 2009-099966 A | 5/2009 |
| JP | 2009-117356 A | 5/2009 |
| JP | 2009-299049 A | 12/2009 |
| JP | 2010-182699 A | 8/2010 |
| JP | 2015-153910 A | 8/2015 |
| KR | 2008-0086844 A | 9/2008 |
| KR | 2009-0033083 A | 4/2009 |
| KR | 2009-0040233 A | 4/2009 |
| KR | 2015-0024491 A | 3/2015 |
| KR | 2016-0029893 A | 3/2016 |
| KR | 2016-0108470 A | 9/2016 |
| TW | 200907015 | 2/2009 |
| TW | 200933947 | 8/2009 |
| TW | 200935637 | 8/2009 |
| TW | 201533023 | 9/2015 |
| WO | WO-2015/122217 | 8/2015 |

* cited by examiner

ORGANIC COMPOUND, LIGHT-EMITTING ELEMENT, LIGHT-EMITTING DEVICE, ELECTRONIC DEVICE, AND LIGHTING DEVICE

CROSS REFERENCE TO RELATED APPLICATIONS

This application is a U.S. National Phase Application under 35 U.S.C. § 371 of International Application PCT/IB2018/050474, filed on Jan. 26, 2018, which is incorporated by reference and claims the benefit of a foreign priority application filed in Japan as Application No. 2017-022299 on Feb. 9, 2017.

TECHNICAL FIELD

One embodiment of the present invention relates to an organic compound, a light-emitting element, a light-emitting device, an electronic device, and a lighting device. However, one embodiment of the present invention is not limited to the above technical field. That is, one embodiment of the present invention relates to an object, a method, a manufacturing method, or a driving method. Alternatively, one embodiment of the present invention relates to a process, a machine, manufacture, or a composition of matter. Specific examples include a semiconductor device, a display device, a liquid crystal display device, and the like.

BACKGROUND ART

A light-emitting element including an EL layer between a pair of electrodes (also referred to as an organic EL element) has characteristics such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state ($S^*$) and a triplet excited state ($T^*$). Light emission from a singlet excited state is referred to as fluorescence, and light emission from a triplet excited state is referred to as phosphorescence. The statistical generation ratio thereof in the light-emitting element is considered to be $S^*:T^*=1:3$. Since the spectrum of light emitted from a light-emitting substance depends on the light-emitting substance, the use of different types of organic compounds as light-emitting substances makes it possible to obtain light-emitting elements which exhibit various colors.

In order to improve element characteristics of such a light-emitting element, improvement of an element structure, development of a material, and the like have been actively carried out (see Patent Document 1, for example).

REFERENCE

Patent Document

[Patent Document 1] Japanese Published Patent Application No. 2010-182699

SUMMARY OF THE INVENTION

Problems to be Solved by the Invention

In development of light-emitting elements, organic compounds used in the light-emitting element are very important to improve the characteristics and reliability. Thus, in one embodiment of the present invention, a novel organic compound is provided. That is, a novel organic compound that is effective in improving element characteristics and reliability is provided. In another embodiment of the present invention, a novel organic compound that can be used in a light-emitting element is provided. In another embodiment of the present invention, a novel organic compound that can be used in an EL layer of a light-emitting element is provided. In addition, a highly efficient, highly reliable, and novel light-emitting element using a novel organic compound of one embodiment of the present invention is provided. In addition, a novel light-emitting device, a novel electronic device, or a novel lighting device is provided. Note that the description of these objects does not preclude the existence of other objects. Note that in one embodiment of the present invention, there is no need to achieve all the objects. Other objects will be apparent from and can be derived from the description of the specification, the drawings, the claims, and the like.

Means for Solving the Problems

One embodiment of the present invention is an organic compound represented by the following general formula (G1), which includes an anthracene skeleton and a carbazole skeleton.

[Chemical Formula 1]

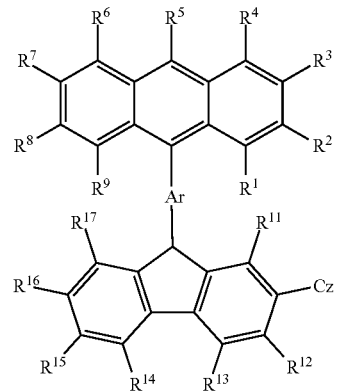

(G1)

Note that in the general formula (G1), Ar represents a substituted or unsubstituted arylene group having 6 to 13 carbon atoms, and when the arylene group has substituents, the substituents may be bonded to each other to form a ring. Furthermore, Cz represents a substituted or unsubstituted carbazole skeleton. Furthermore, each of $R^1$ to $R^9$ and $R^{11}$ to $R^{17}$ independently represents any of hydrogen, a substituted or unsubstituted alkyl group having 1 to 6 carbon atoms, a substituted or unsubstituted cycloalkyl group having 3 to 6 carbon atoms, or a substituted or unsubstituted aryl group having 6 to 13 carbon atoms. Furthermore, at least one of the following pairs may form a fused ring: $R^{12}$ and $R^{13}$; $R^{14}$ and $R^{15}$; $R^{15}$ and $R^{16}$; or $R^{16}$ and $R^{17}$.

Another embodiment of the present invention is an organic compound in which the 9-position, 3-position, or 2-position of the carbazole skeleton represented by Cz in the above general formula (G1) is bonded to the carbazole skeleton.

Another embodiment of the present invention is the organic compound in which Ar in the above general formula (G1) is a substituted or unsubstituted phenylene group or a substituted or unsubstituted biphenyldiyl group.

Another embodiment of the present invention is the organic compound in which $R^5$ in the above general formula (G1) is a substituted or unsubstituted aryl group having 6 to 13 carbon atoms.

The above-described organic compound of one embodiment of the present invention includes an anthracene skeleton and a carbazole skeleton. Although organic compounds having an anthracene skeleton have been widely developed as fluorescent host materials having a bipolar property, the organic compound of one embodiment of the present invention, including a carbazole skeleton in addition to an anthracene skeleton, is a fluorescent host material with a superior hole-transport property, compared to an organic compound that includes only an anthracene skeleton.

Furthermore, the organic compound of one embodiment of the present invention is a fluorescent host material having an anthracene skeleton and a bicarbazole skeleton. Note that for such an organic compound, the HOMO orbital is in the bicarbazole skeleton, and the HOMO level thereof tends to be shallower, compared to the case where the HOMO orbital is in the anthracene skeleton. When such a fluorescent host material having a shallow HOMO level is used for a light-emitting layer, a difference in HOMO level between the light-emitting layer and a hole-transport layer formed in contact with the light-emitting layer is small, so that the barrier against injection of holes from the hole-transport layer to the light-emitting layer is reduced, and thus the injection property of holes from the hole-transport layer to the light-emitting layer is improved. Thus, a reduction in driving voltage or an improvement in emission efficiency can be achieved.

The above-described organic compound of one embodiment of the present invention includes an anthracene skeleton and a carbazole skeleton, and a bonding position between the 2-position of a first carbazole skeleton bonded to the anthracene skeleton and a second carbazole skeleton bonded thereto is made a desired position; whereby a Stokes shift is smaller and higher singlet excitation energy can be obtained, compared to the case where the 3-position of the first carbazole skeleton is bonded to the second carbazole skeleton, so that energy transfer to the guest material with a shorter wavelength is easily performed. This can improve the emission efficiency of a light-emitting element. Moreover, the reliability of the element can be improved. Note that the organic compound of one embodiment of the present invention is easily synthesized, which is preferable, because the 2-position of the first carbazole skeleton bonded to the anthracene skeleton is bonded to the 9-position, 3-position, or 2-position of the second carbazole skeleton.

Another embodiment of the present invention is an organic compound represented by a structural formula (200), a structural formula (220), a structural formula (221), a structural formula (252), or a structural formula (253).

[Chemical Formulae 2]

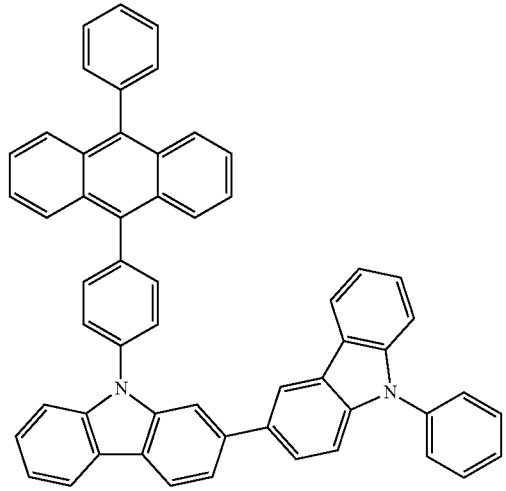

(200)

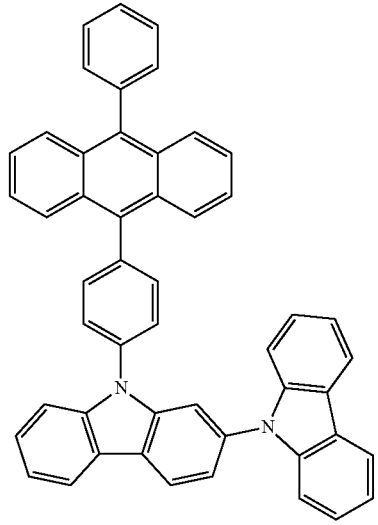

(220)

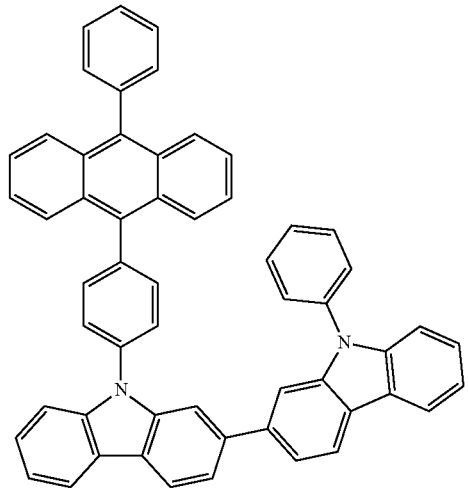

(221)

-continued (252)

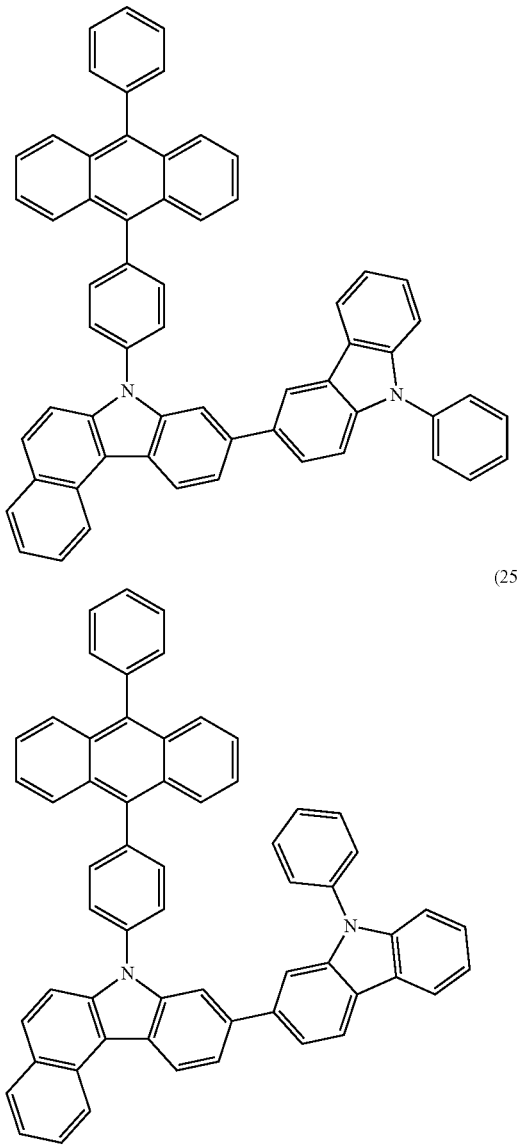

(253)

Another embodiment of the present invention is a light-emitting element in which an organic compound including an anthracene skeleton and a carbazole skeleton is used. Note that the present invention also includes a light-emitting element containing a guest material in addition to the above organic compound.

Another embodiment of the present invention is a light-emitting element in which the above-described organic compound of one embodiment of the present invention is used. Note that the present invention also includes a light-emitting element that is formed using the organic compound of one embodiment of the present invention for an EL layer between a pair of electrodes and a light-emitting layer in the EL layer. In addition to the light-emitting elements, a light-emitting device including a transistor, a substrate, and the like is also included in the scope of the invention. Furthermore, in addition to the light-emitting device, an electronic device and a lighting device that include a microphone, a camera, an operation button, an external connection portion, a housing, a cover, a support, a speaker, or the like are also included in the scope of the invention.

In addition, the scope of one embodiment of the present invention includes a light-emitting device including a light-emitting element, and a lighting device including the light-emitting device. Accordingly, the light-emitting device in this specification refers to an image display device or a light source (including a lighting device). In addition, a light-emitting device includes a module in which a light-emitting device is connected to a connector such as an FPC (Flexible Printed Circuit) or a TCP (Tape Carrier Package), a module in which a printed wiring board is provided on the tip of a TCP, or a module in which an IC (integrated circuit) is directly mounted on a light-emitting element by a COG (Chip On Glass) method.

EFFECTS OF THE INVENTION

According to one embodiment of the present invention, a novel organic compound can be provided. In other words, a novel organic compound that is effective in improving the element characteristics and reliability can be provided. In addition, according to one embodiment of the present invention, a novel organic compound that can be used in a light-emitting element can be provided. According to one embodiment of the present invention, a novel organic compound that can be used in an EL layer of a light-emitting element can be provided. In addition, a highly efficient, highly reliable, and novel light-emitting element in which a novel organic compound of one embodiment of the present invention is used can be provided. In addition, a novel light-emitting device, a novel electronic device, or a novel lighting device can be provided. Note that the description of these effects does not preclude the existence of other effects. Note that one embodiment of the present invention need not necessarily achieve all the effects. Note that other effects will be apparent from the description of the specification, the drawings, the claims, and the like, and other effects can be derived from the description of the specification, the drawings, the claims, and the like.

MODES FOR CARRYING OUT THE INVENTION

Figure 1A:
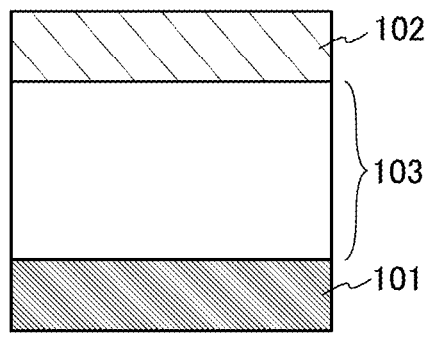
FIGS. 1A-1E Drawings illustrating the structures of light-emitting elements.

Embodiments of the present invention will be described below in detail with reference to the drawings. However, the present invention is not limited to the following description, and the modes and details can be various changed unless departing from the spirit and scope of the present invention. Thus, the present invention should not be construed as being limited to the description in the following embodiments.

Note that the position, size, range, or the like of each structure illustrated in the drawings and the like do not represent the actual position, size, range, or the like in some cases for easy understanding. Therefore, the disclosed invention is not necessarily limited to the position, size, range, or the like disclosed in the drawings and the like.

Furthermore, when describing the structures of the invention with reference to the drawings in this specification and the like, the reference numerals denoting the same components are commonly used in different drawings.

Embodiment 1

In this embodiment, organic compounds of embodiments of the present invention will be described.

The organic compound described in this embodiment has the structure represented by the following general formula (G1) which includes an anthracene skeleton and a carbazole skeleton.

[Chemica Formula 3]

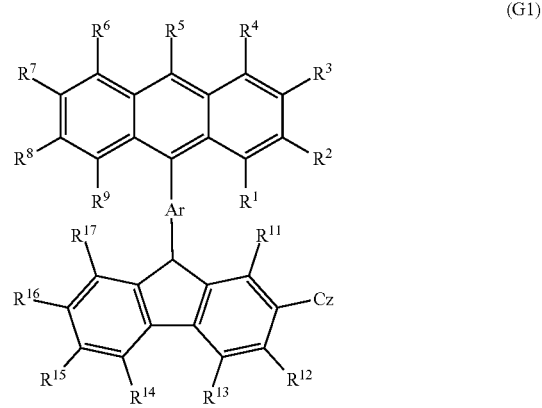

(G1)

In the general formula (G1), Ar represents a substituted or unsubstituted arylene group having 6 to 13 carbon atoms, and when the arylene group has substituents, the substituents may be bonded to each other to form a ring. Furthermore, Cz represents a substituted or unsubstituted carbazole skeleton. Furthermore, each of $R^1$ to $R^9$ and $R^{11}$ to $R^{17}$ independently represents any of hydrogen, a substituted or unsubstituted alkyl group having 1 to 6 carbon atoms, a substituted or unsubstituted cycloalkyl group having 3 to 6 carbon atoms, or a substituted or unsubstituted aryl group having 6 to 13 carbon atoms. Furthermore, at least one of the following pairs may form a fused ring: $R^{12}$ and $R^{13}$; $R^{14}$ and $R^{15}$; $R^{15}$ and $R^{16}$; or $R^{16}$ and $R^{17}$.

In the above general formula (G1), in the case where any of the substituted or unsubstituted arylene group having 6 to 13 carbon atoms, the substituted or unsubstituted carbazole skeleton, the substituted or unsubstituted alkyl group having 1 to 6 carbon atoms, the substituted or unsubstituted cycloalkyl group having 3 to 6 carbon atoms, or the substituted or unsubstituted aryl group having 6 to 13 carbon atoms includes a substituent, examples of the substituent include an alkyl group having 1 to 6 carbon atoms, such as a methyl group, an ethyl group, a propyl group, an isopropyl group, a butyl group, an isobutyl group, a sec-butyl group, a tert-butyl group, a pentyl group, or a hexyl group; a cycloalkyl group having 5 to 7 carbon atoms, such as a cyclopentyl group, a cyclohexyl group, a cycloheptyl group, a 1-norbornyl group, or a 2-norbornyl group; and an aryl group having 6 to 12 carbon atoms, such as a phenyl group or a biphenyl group.

In the above general formula (G1), specific examples of the substituted or unsubstituted arylene group having 6 to 13 carbon atoms include a phenylene group, 2,5-dimethyl-1,4-phenylene group, a naphthalenediyl group, a biphenyldiyl group, a 9,9-dimethylfluorendiyl group, 9,9-diphenylfluorendiyl group, and a 9,9'-spirobifluorendiyl group.

In the above general formula (G1), specific examples of the substituted or unsubstituted carbazole skeleton include benzo[a]carbazole, benzo[b]carbazole, benzo[c]carbazole, dibenzo[a,c]carbazole, dibenzo[a,g]carbazole, dibenzo[c,g]carbazole, dibenzo[b,g]carbazole, naphtho[2,3-c]carbazole, and naphtho[1,2-c]carbazole.

In the above general formula (G1), specific examples of the substituted or unsubstituted alkyl group having 1 to 6 carbon atoms include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

In the general formulae (G1), specific examples of the substituted or unsubstituted aryl group having 6 to 13 carbon atoms include a phenyl group, a naphthyl group (a 1-naphthyl group and a 2-naphthyl group), a tolyl group (an o-tolyl group, an m-tolyl group, and a p-tolyl group), and a biphenyl group (a biphenyl-2-yl group, a biphenyl-3-yl group, and a biphenyl-4-yl group).

The organic compound of one embodiment of the present invention represented by the general formula (G1) includes an anthracene skeleton and a carbazole skeleton. Although organic compounds having an anthracene skeleton have been widely developed as fluorescent host materials having a bipolar property, the organic compound represented by the general formula (G1) including an anthracene skeleton and a carbazole skeleton is a fluorescent host material with a superior hole-transport property, compared to an organic compound that includes only an anthracene skeleton.

The organic compound of one embodiment of the present invention represented by the general formula (G1) is a fluorescent host material having an anthracene skeleton and a bicarbazole skeleton. For such an organic compound, the HOMO orbital is in the bicarbazole skeleton, and the HOMO level thereof tends to be shallower, compared to the case where the HOMO orbital is in the anthracene skeleton. When such a fluorescent host material having a shallow HOMO level is used for a light-emitting layer, a difference in HOMO level between the light-emitting layer and the hole-transport layer formed in contact with the light-emitting layer is small, so that the barrier against injection of holes from the hole-transport layer to the light-emitting layer is reduced, and thus the injection property of holes from the hole-transport layer to the light-emitting layer is improved. Thus, a reduction in driving voltage or an improvement in emission efficiency can be achieved.

The organic compound of one embodiment of the present invention includes an anthracene skeleton and a carbazole skeleton, and the bonding position of the second phenylcarbazole bonded to the 3-position of the first phenylcarbazole bonded to the anthracene skeleton is made a desired position; whereby emission efficiency and the reliability of the light-emitting element using the organic compound can be improved. Note that the bonding position of the second phenylcarbazole bonded to the 3-position of the first phenylcarbazole is preferably the 2-position of second phenylcarbazole as shown in the general formula (G1).

Next, specific structural formulae of the above-described organic compounds of embodiments of the present invention are shown below. However, the present invention is not limited to these formulae.

[Chemical Formulae 4]

(200)

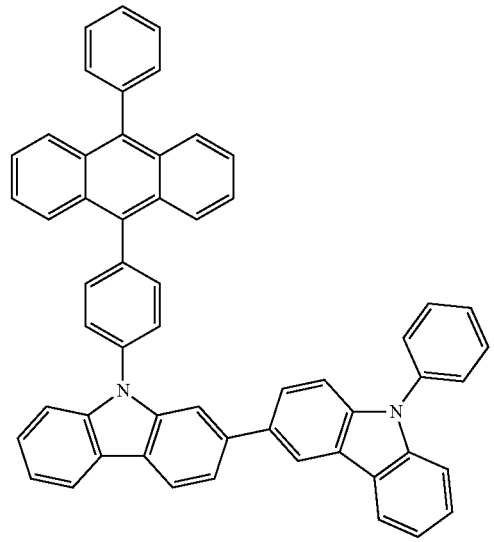

(201)

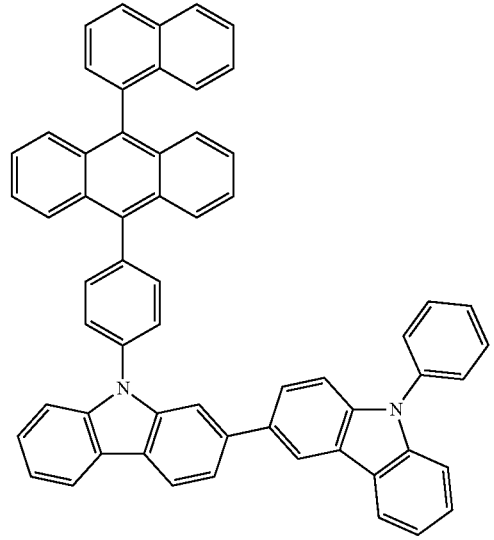

(202)
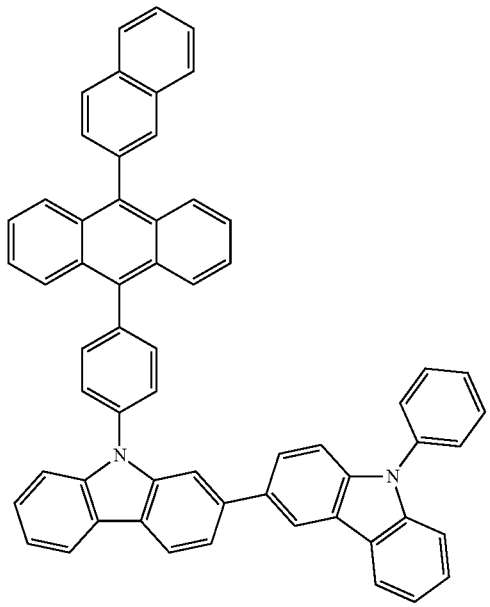
(203)
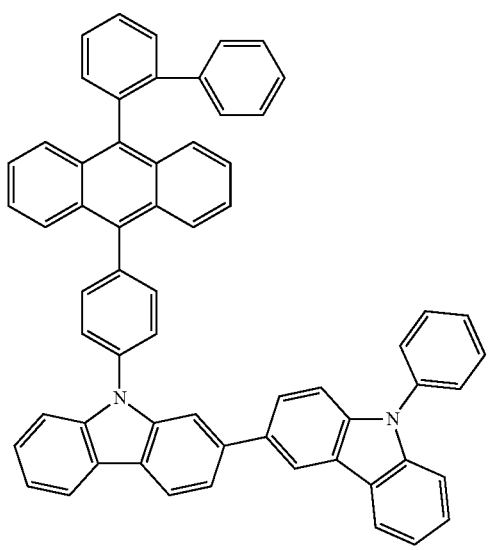
(204)
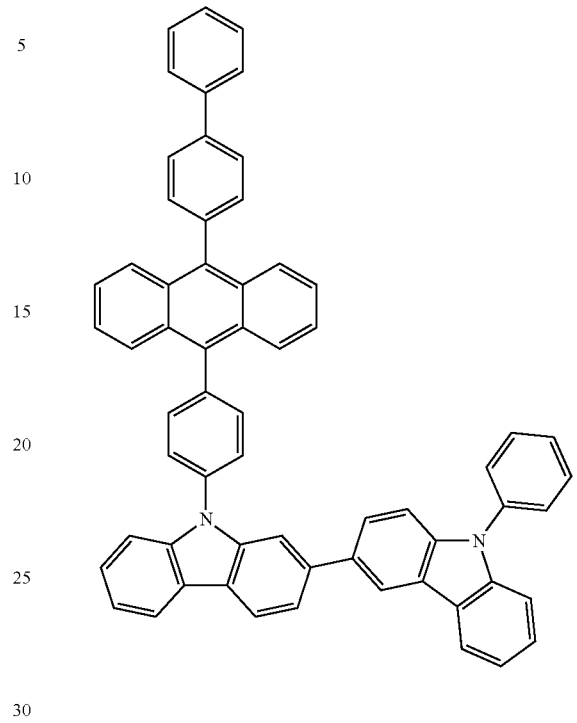
(205)
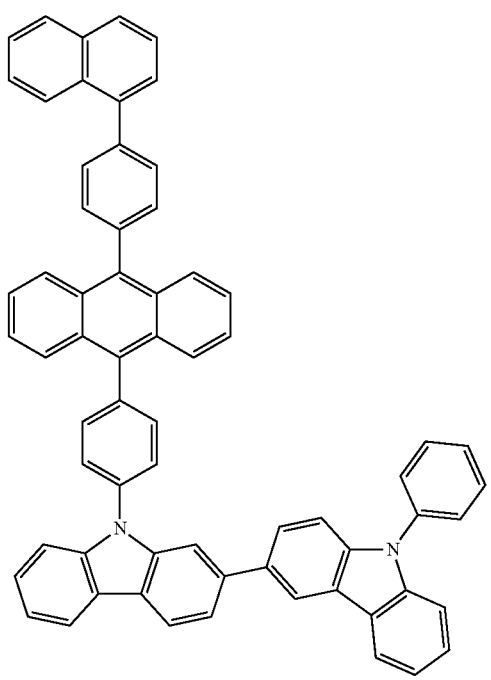

(206)
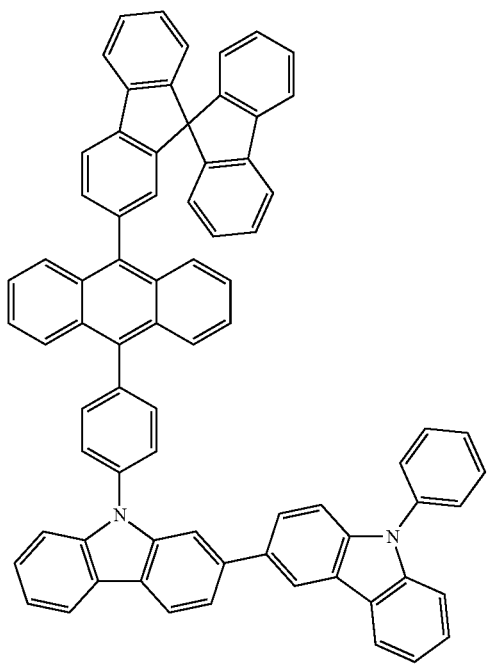
(208)
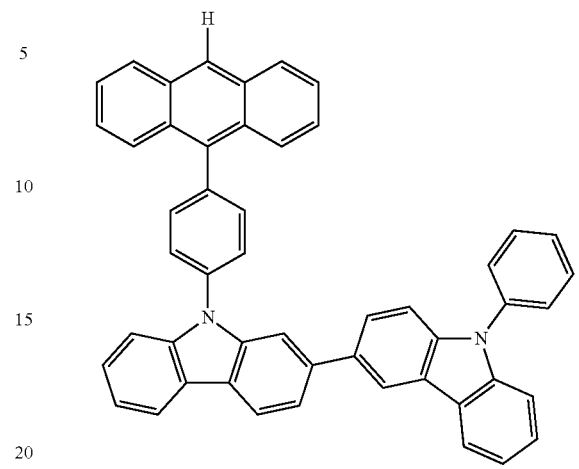
[Chemical Formulae 5]
(209)
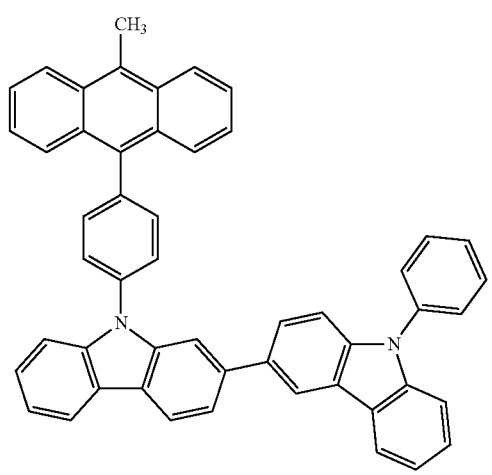
(207)
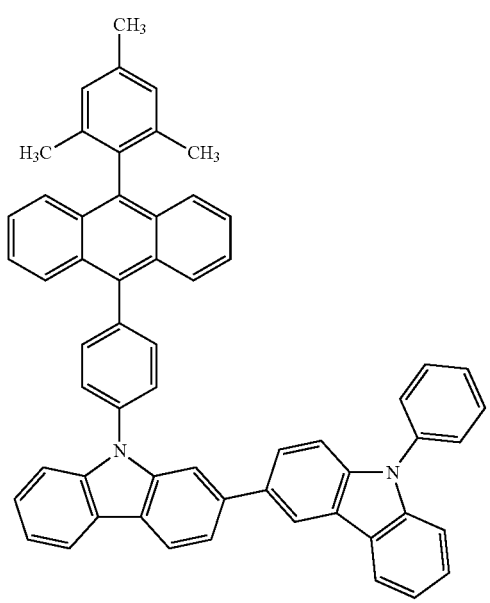
(210)
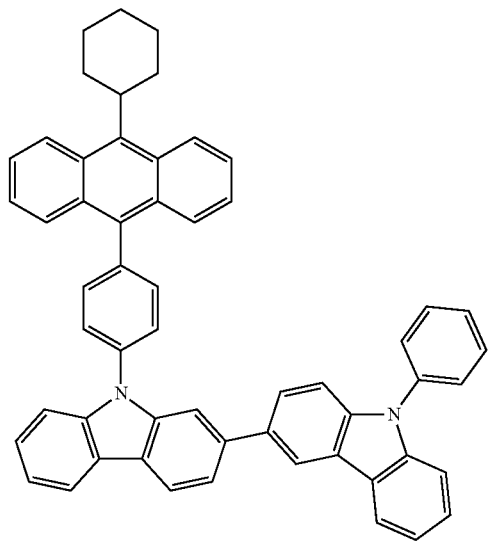

(211)
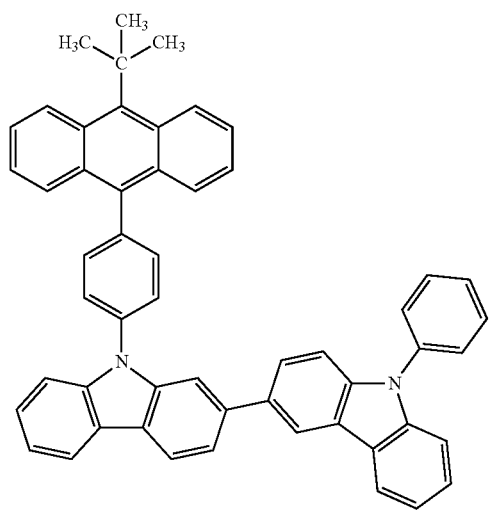
(212)
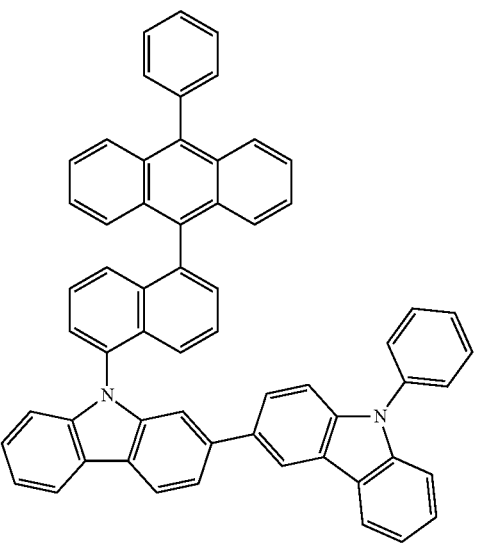
(214)
(213)
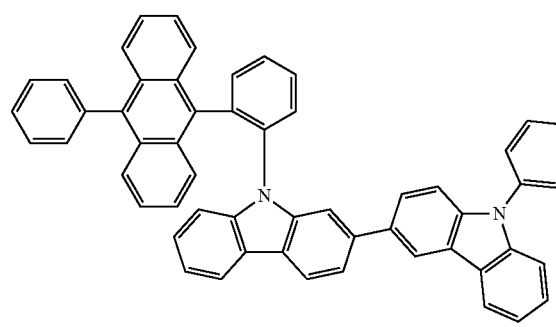
(215)
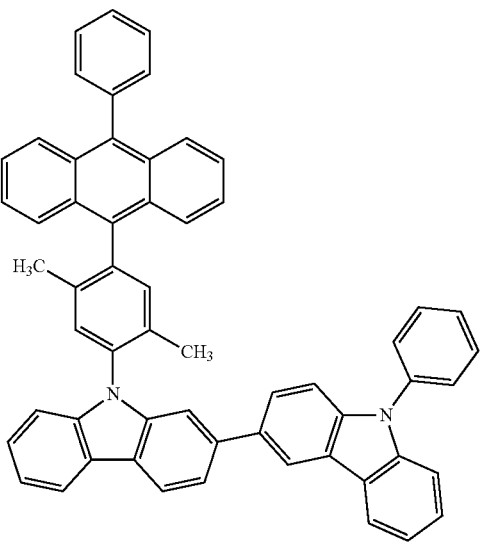

[Chemical Formulae 6]
(216)
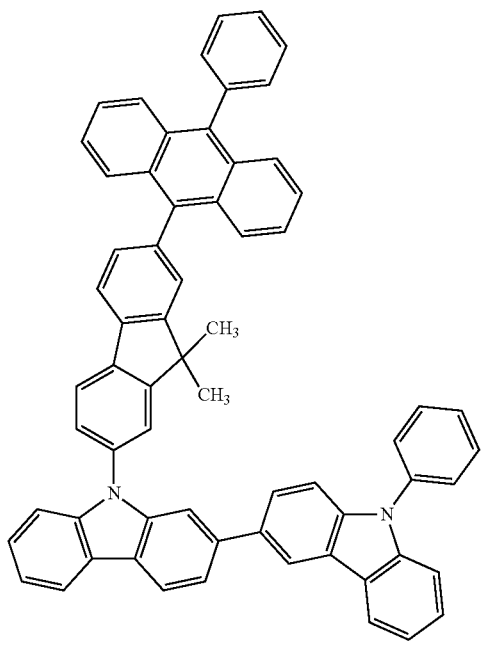
(217)
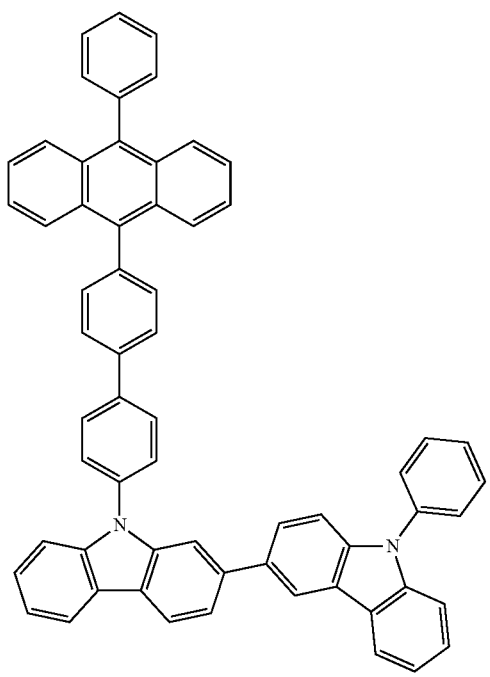
(218)
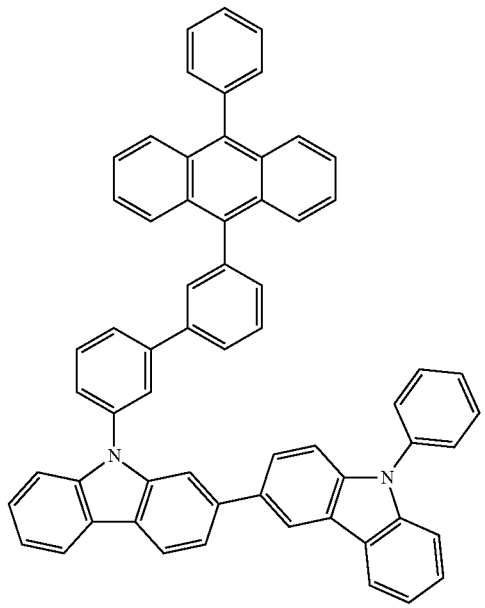
(219)
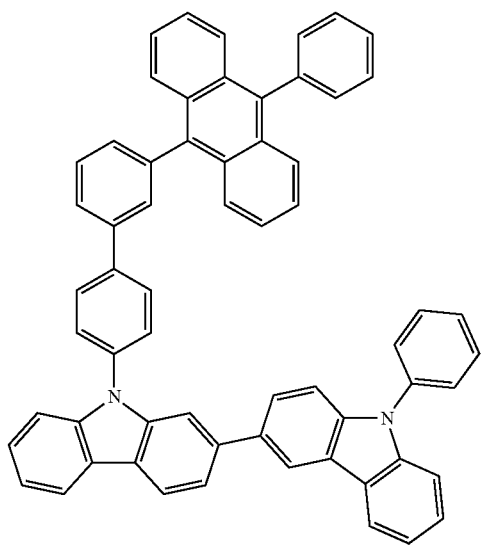

(220)
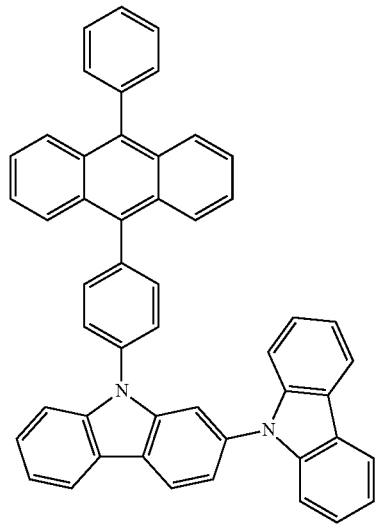
(221)
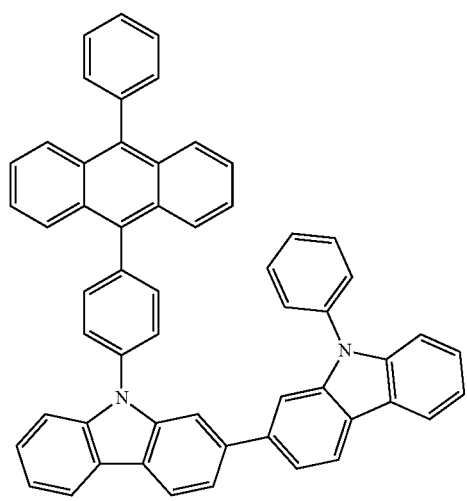
(222)
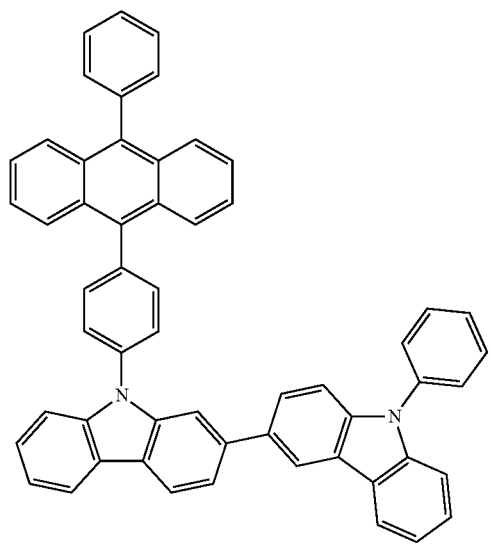
(223)
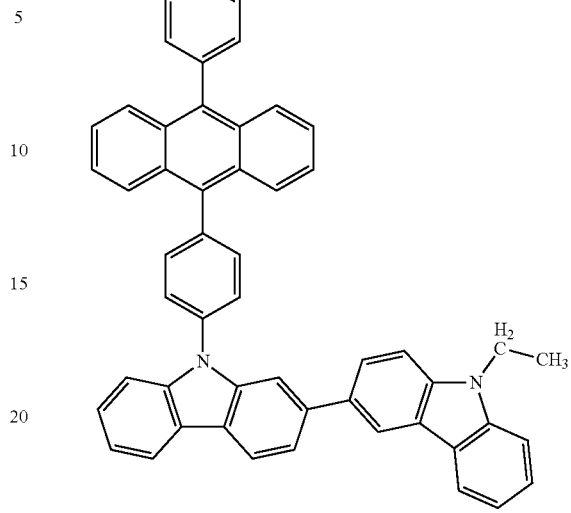
(224)
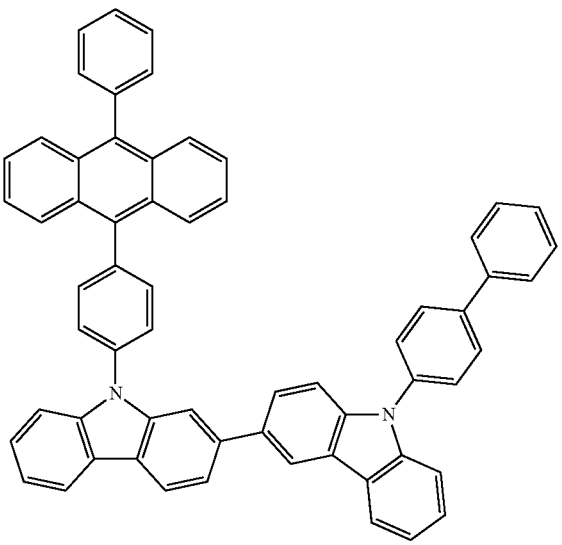

(225)
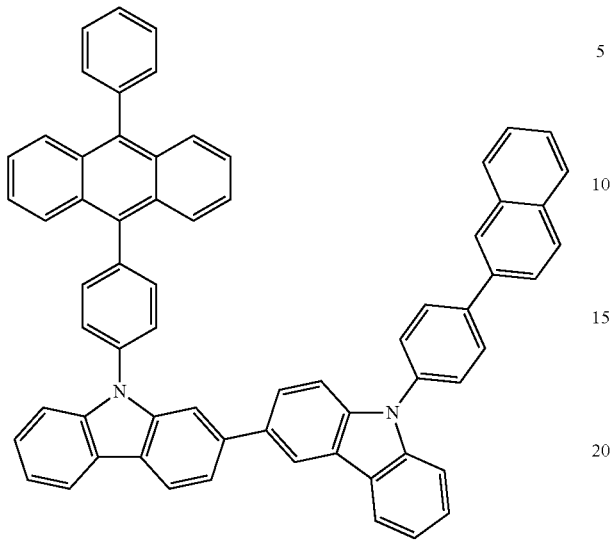
(227)
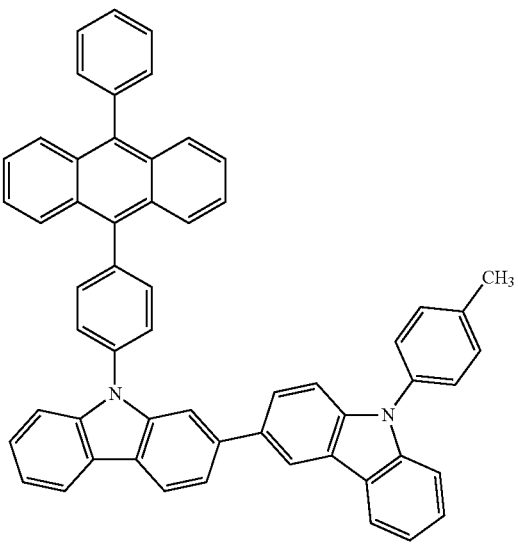
[Chemical Formulae 7]
(226)
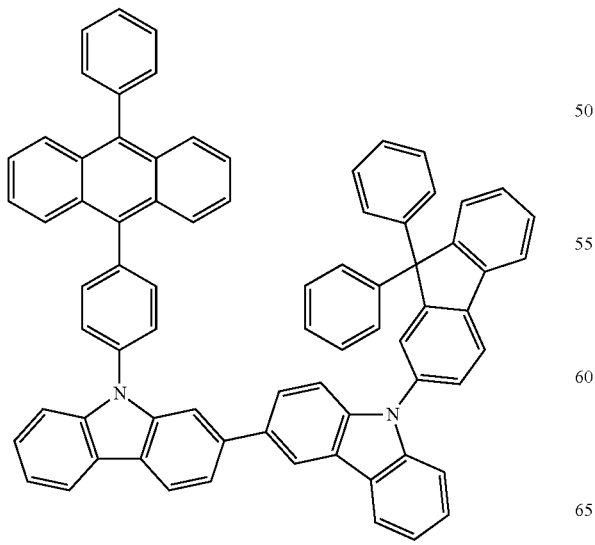
(228)
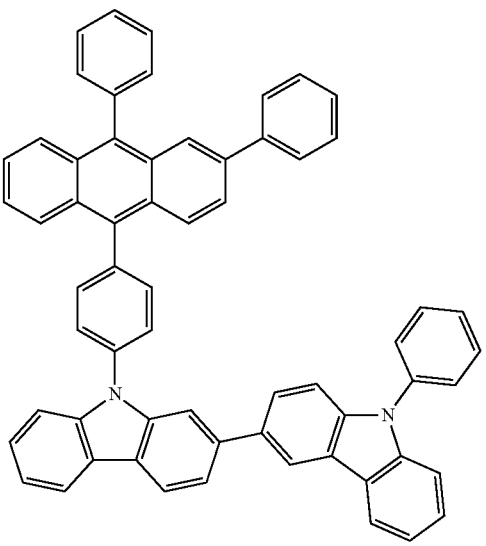

(229)
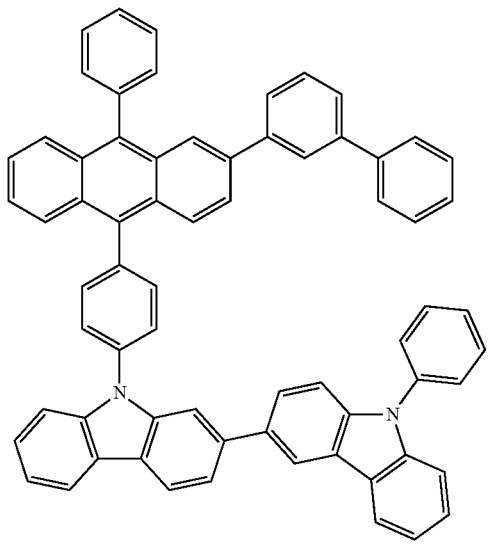
(231)
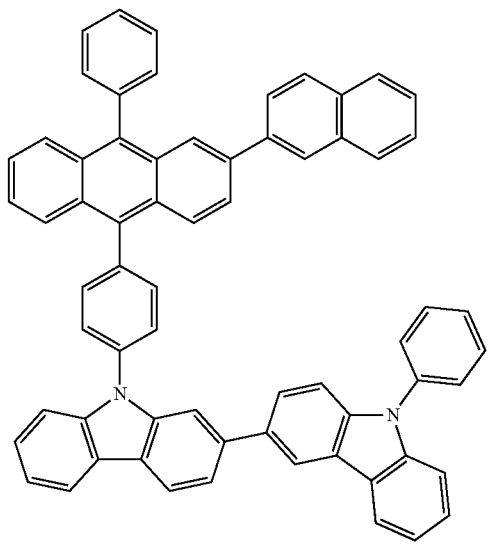
(230)
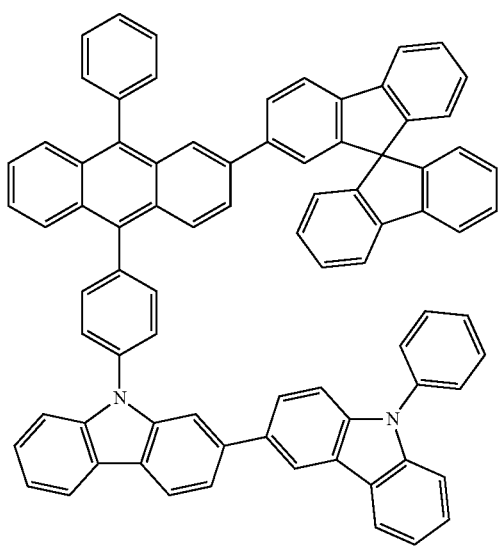
(232)
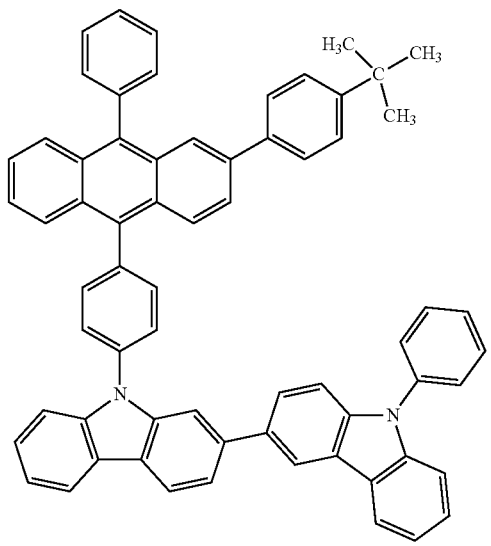

(233)
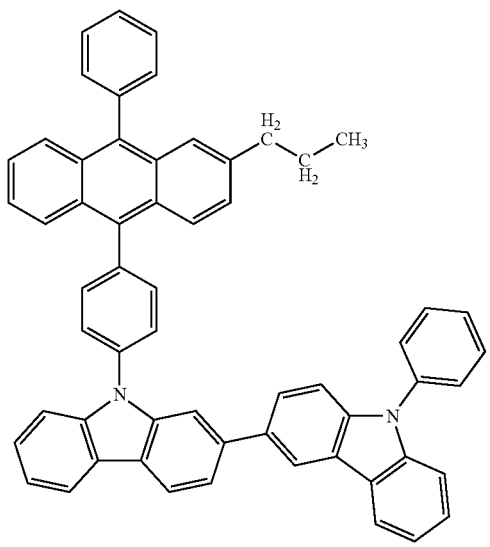
(234)
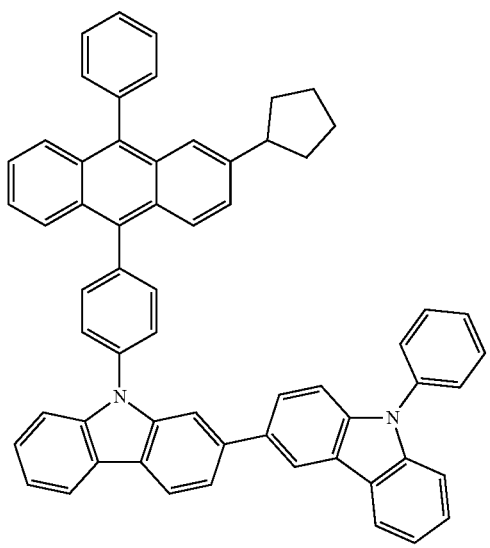
[Chemical Formulae 8]
(235)
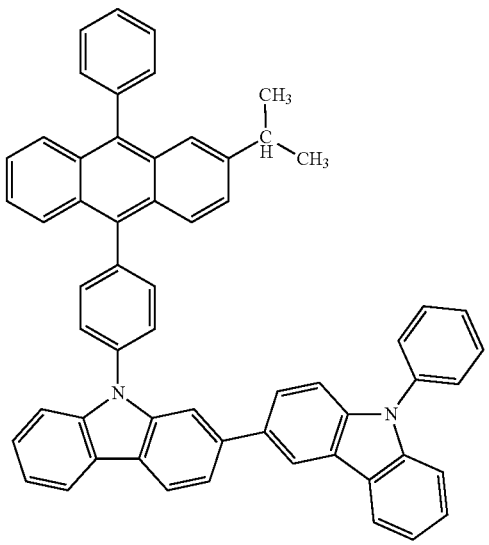
(236)
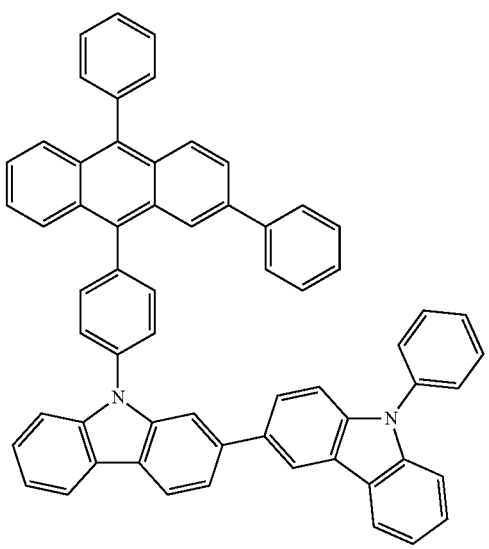

(237)
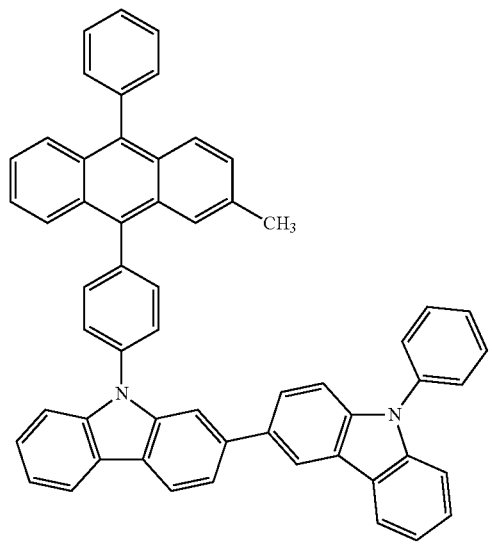
(239)
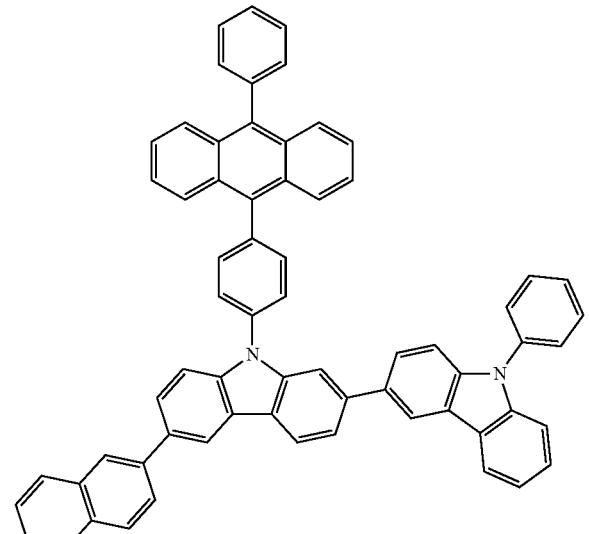
(238)
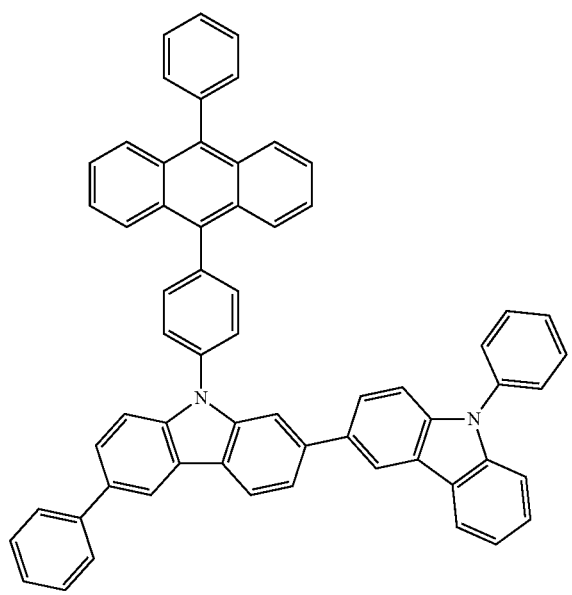
(240)
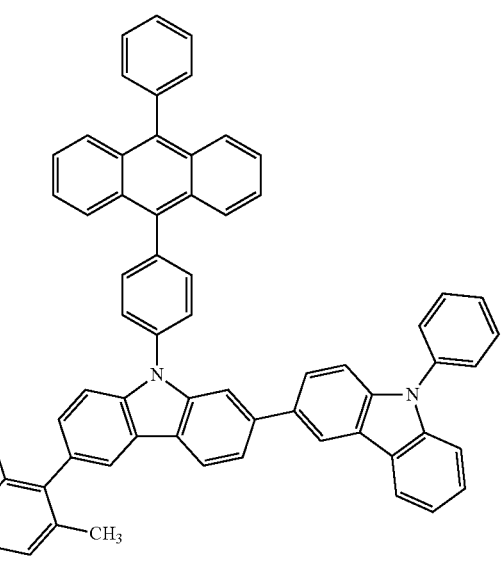

-continued
(241)
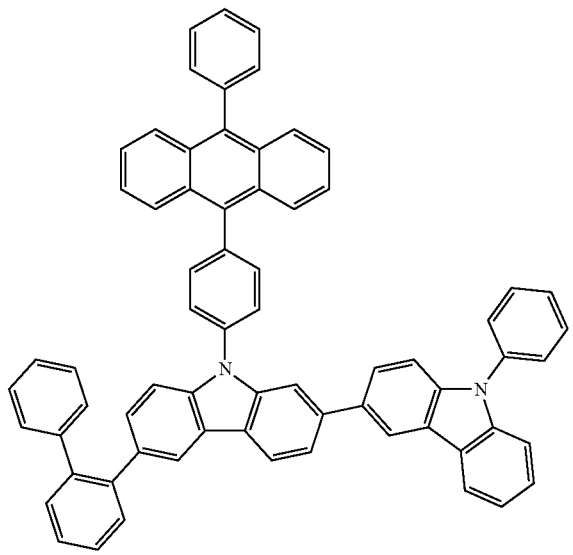
(243)
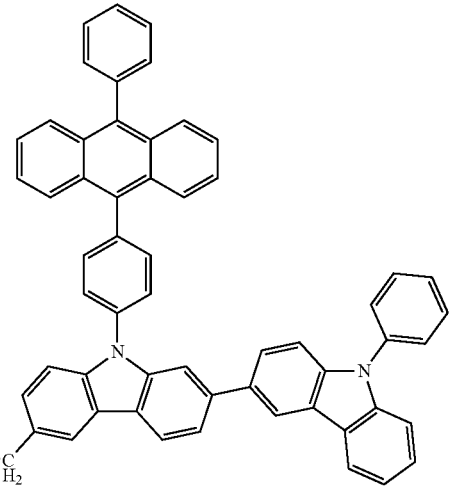
[Chemical Formulae 9]
(242)
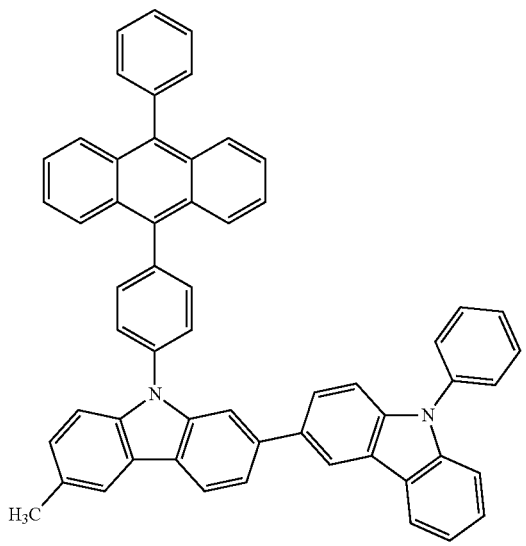
(244)
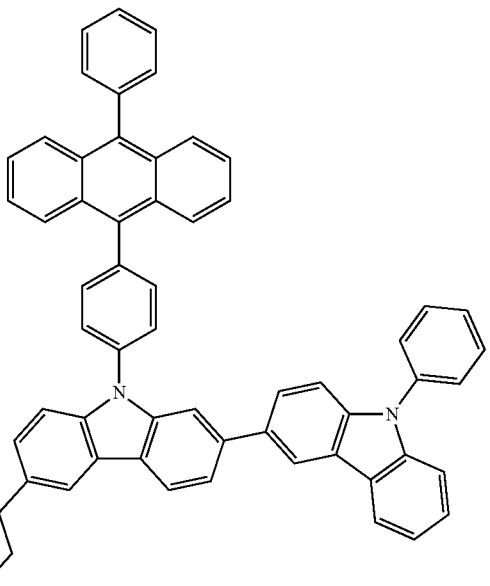

(245)
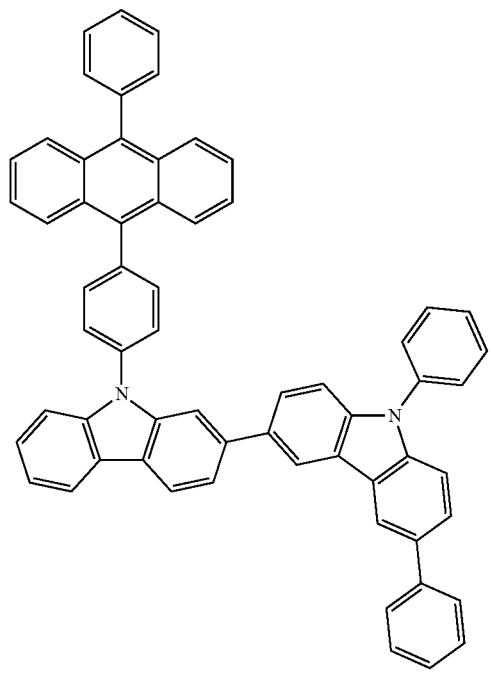
(247)
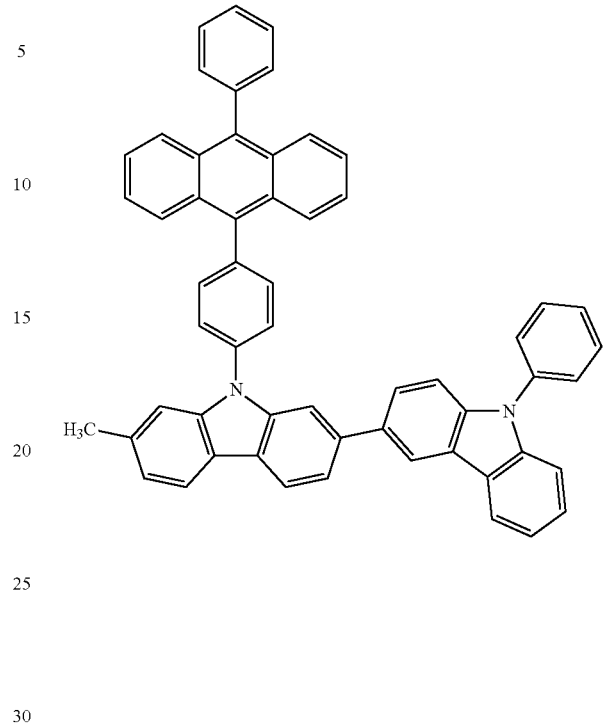
[Chemical Formulae 10]
(246)
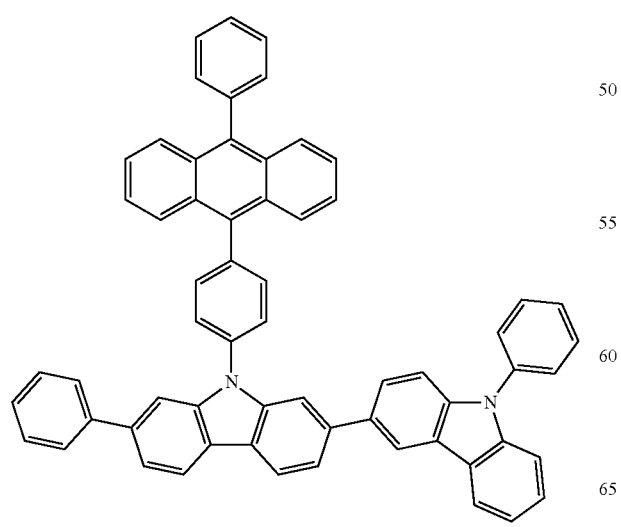
(248)
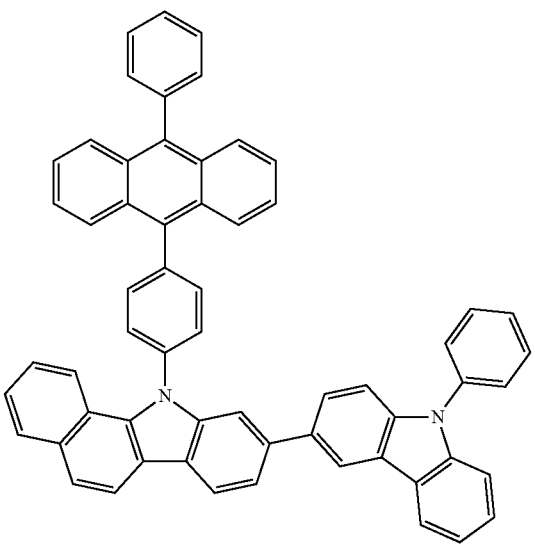

(249)
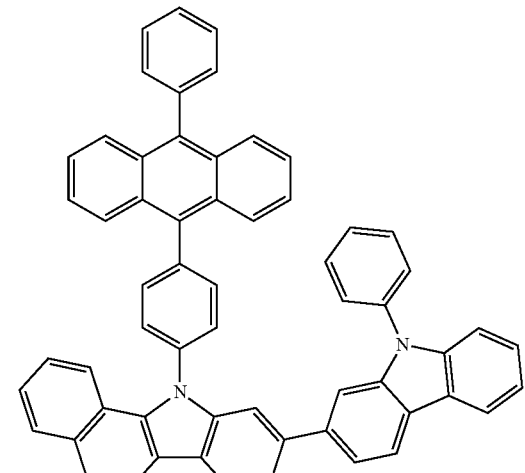
(250)
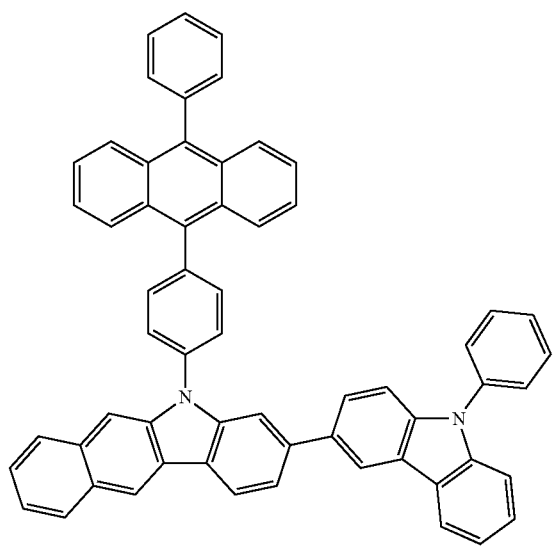
(251)
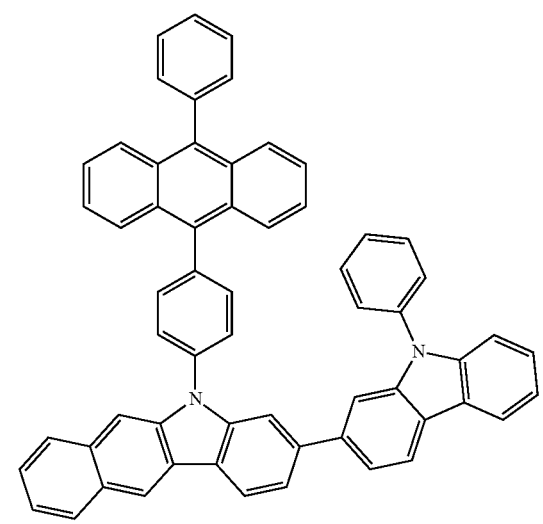
(252)
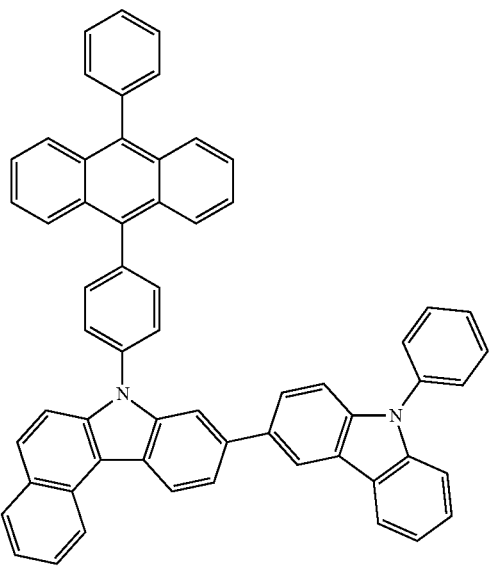
(253)
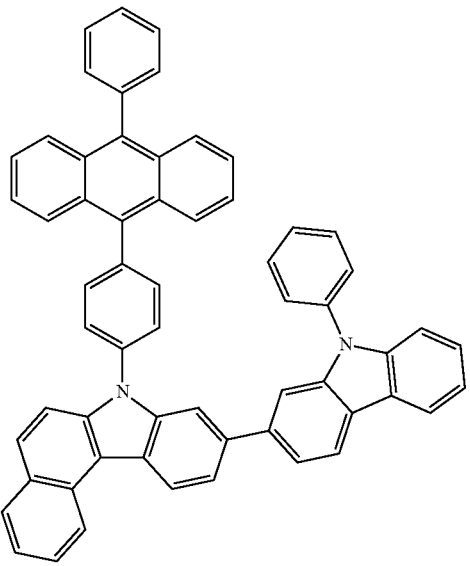

[Chemical Formulae 11]
(254)
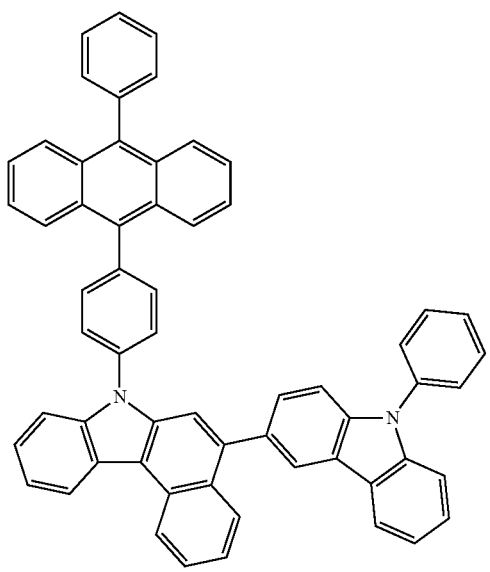
(255)
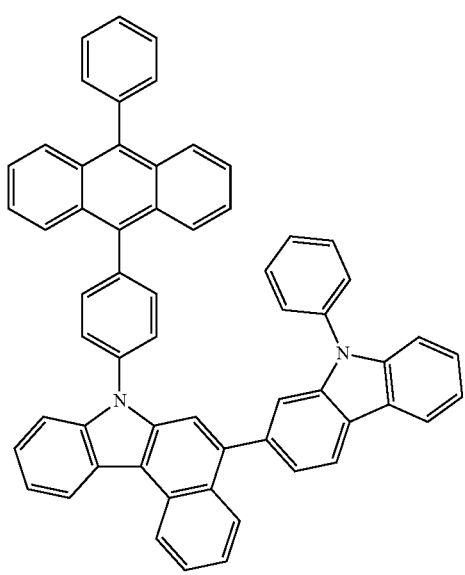
(256)
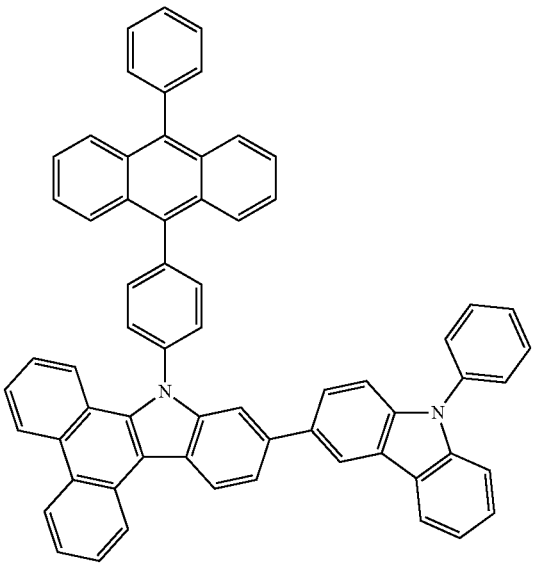
(257)
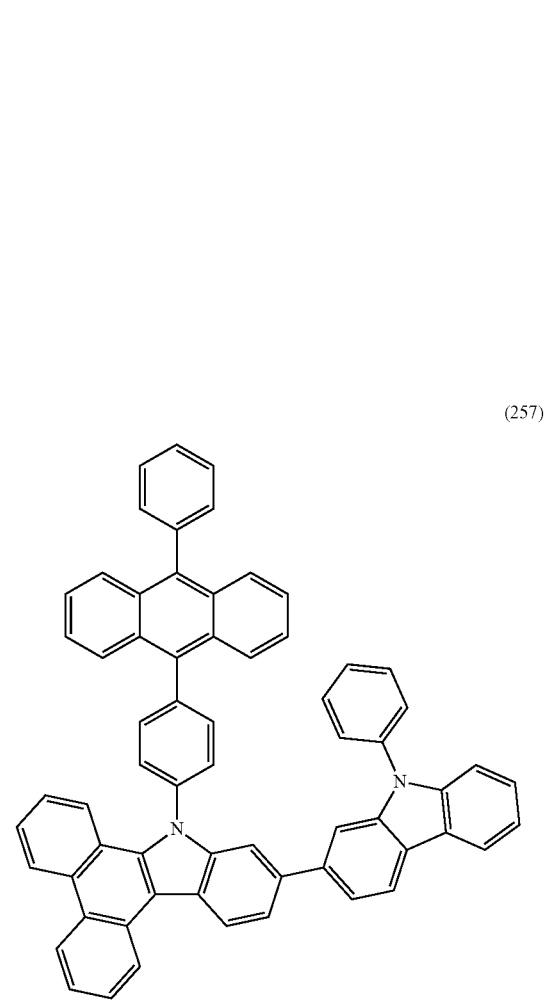

(258)

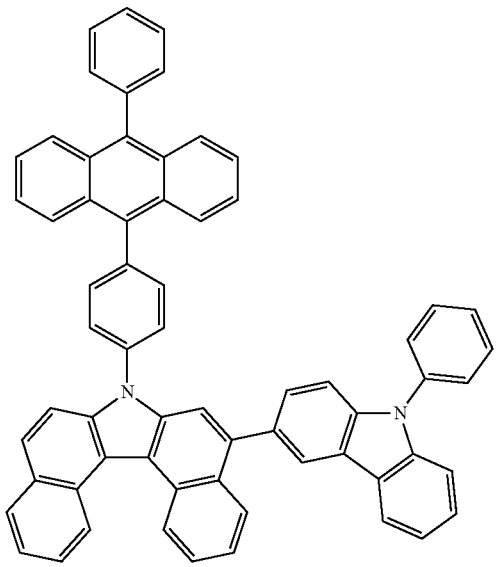

(259)

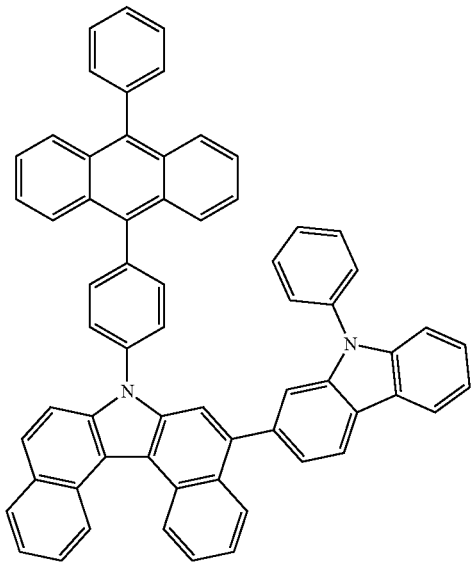

(260)

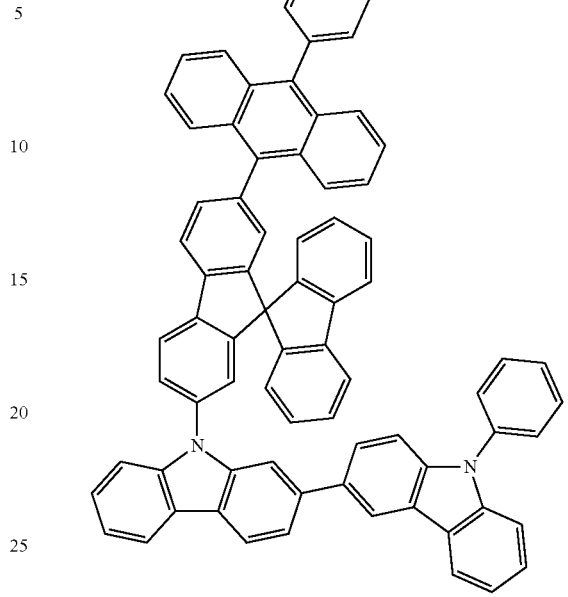

Note that the organic compounds represented by the above structural formulae (200) to (260) are examples included in the organic compound represented by the above general formula (G1), and the organic compound of one embodiment of the present invention is not limited thereto.

Next, an example of a method for synthesizing the organic compound which is one embodiment of the present invention and is represented by the general formula (G1) will be described.

<<Method for Synthesizing Organic Compound Represented by General Formula (G1)>>

First, an example of a method for synthesizing the organic compound represented by the following general formula (G1) will be described.

[Chemical Formula 12]

(G1)

In the general formula (G1), Ar represents a substituted or unsubstituted arylene group having 6 to 13 carbon atoms, and when the arylene group has substituents, the substituents may be bonded to each other to form a ring. Furthermore, Cz represents a substituted or unsubstituted carbazole skeleton. Furthermore, each of $R^1$ to $R^9$ and $R^{11}$ to $R^{17}$ independently represents any of hydrogen, a substituted or unsubstituted alkyl group having 1 to 6 carbon atoms, a substituted or unsubstituted cycloalkyl group having 3 to 6 carbon atoms, or a substituted or unsubstituted aryl group having 6 to 13 carbon atoms. Furthermore, at least one of the following pairs may form a fused ring: $R^{12}$ and $R^{13}$; $R^{14}$ and $R^{15}$; $R^{15}$ and $R^{16}$; or $R^{16}$ and $R^{17}$.

The organic compound represented by the above general formula (G1) can be synthesized by a synthesis scheme (A-1) shown below. That is, a halide of an anthracene derivative (compound 1) is coupled with an organoboron compound or a boronic acid (compound 2) of a carbazole derivative or a condensed polycyclic carbazole derivative by the Suzuki-Miyaura reaction, whereby the organic compound represented by the general formula (G1) can be obtained.

[Chemical Formula 13]

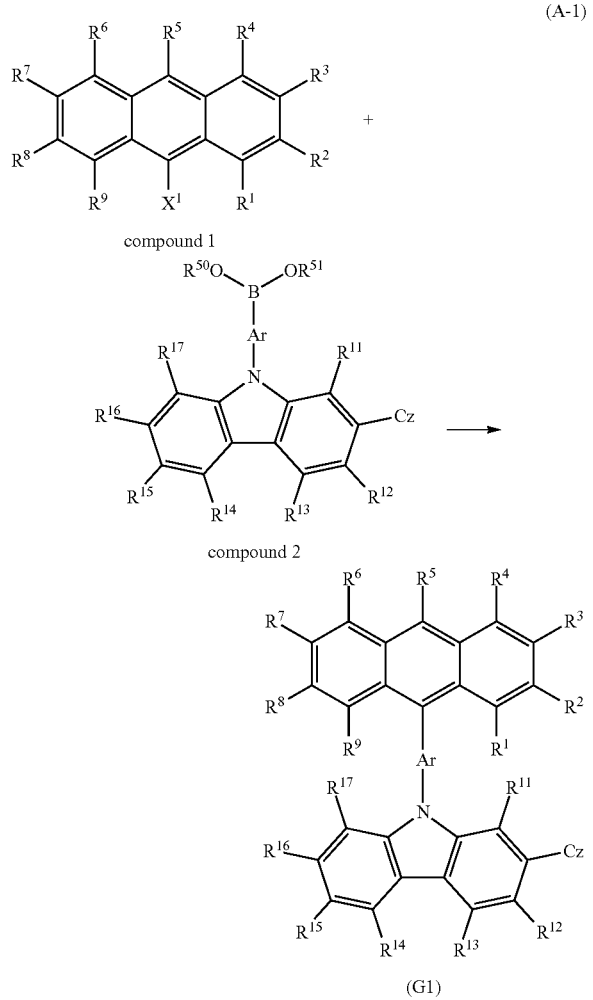

Note that in the above synthesis scheme (A-1), Ar represents a substituted or unsubstituted arylene group having 6 to 13 carbon atoms, and when the arylene group has substituents, the substituents may be bonded to each other to form a ring. Furthermore, Cz represents a substituted or unsubstituted carbazole skeleton. Furthermore, each of $R^1$ to $R^9$ and $R^{11}$ to $R^{17}$ independently represents any of hydrogen, a substituted or unsubstituted alkyl group having 1 to 6 carbon atoms, a substituted or unsubstituted cycloalkyl group having 3 to 6 carbon atoms, and a substituted or unsubstituted aryl group having 6 to 13 carbon atoms. Furthermore, at least one of the following pairs may form a fused ring: $R^{12}$ and $R^{13}$; $R^{14}$ and $R^{15}$; $R^{15}$ and $R^{16}$; or $R^{16}$ and $R^{17}$. Furthermore, $R^{50}$ and $R^{51}$ each represent hydrogen or an alkyl group having 1 to 6 carbon atoms. Note that $R^{50}$ and $R^{51}$ may be bonded to each other to form a ring. Furthermore, $X^1$ represents a halogen or a triflate group.

Examples of a palladium catalyst that can be used in the above synthesis scheme (A-1) include, but are not limited to, palladium(II) acetate, tetrakis(triphenylphosphine)palladium(0), and bis(triphenylphosphine)palladium(II) dichloride. Examples of ligands of the palladium catalyst that can be used in the synthesis scheme (A-1) include tri(ortho-tolyl)phosphine, triphenylphosphine, and tricyclohexylphosphine. The ligand of the palladium catalyst that can be used is not limited to these. Examples of a base that can be used in the synthesis scheme (A-1) include, but are not limited to, organic bases such as sodium tert-butoxide and inorganic bases such as potassium carbonate and sodium carbonate. Examples of a solvent that can be used in the synthesis scheme (A-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of water and an ether such as ethylene glycol dimethyl ether. However, the solvent that can be used is not limited to these. In addition, a mixed solvent of toluene and water, a mixed solvent of toluene, ethanol, and water, or a mixed solvent of water and an ether such as ethylene glycol dimethyl ether is more preferred.

Furthermore, in addition to the organoboron compound or the boronic acid, an organic aluminum compound, an organic zirconium compound, an organic zinc compound, an organic tin compound, or the like may be used as the compound 2 in the above synthesis scheme (A-1).

Alternatively, the coupling reaction shown in a synthesis scheme (A-2) may be used as the coupling reaction other than the reaction shown in the synthesis scheme (A-1). That is, in the coupling reaction shown in the synthesis scheme (A-2), a halide of an anthracene derivative (compound 3) and a carbazole derivative (compound 4) are coupled using a metal catalyst, a metal, or a metal compound in the presence of a base, so that the organic compound represented by the general formula (G1) can be obtained.

[Chemical Formula 14]

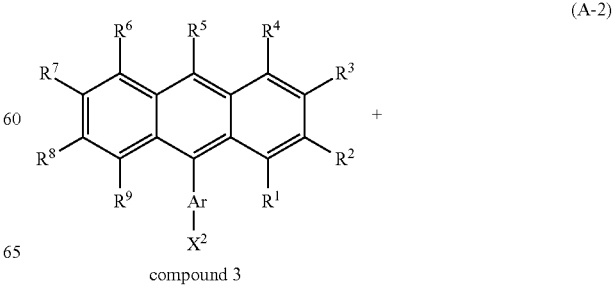

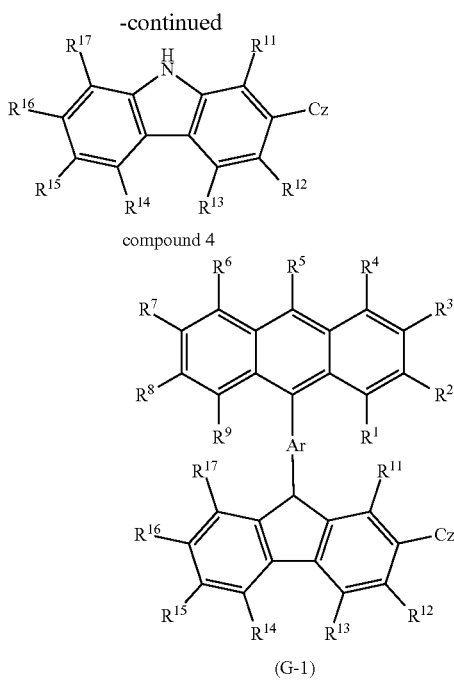

compound 4

(G-1)

In the above synthesis scheme (A-2), Ar represents a substituted or unsubstituted arylene group having 6 to 13 carbon atoms, and when the arylene group has substituents, the substituents may be bonded to each other to form a ring. Furthermore, Cz represents a substituted or unsubstituted carbazole skeleton. Furthermore, each of $R^1$ to $R^9$ and $R^{11}$ to $R^{17}$ independently represents any of hydrogen, a substituted or unsubstituted alkyl group having 1 to 6 carbon atoms, a substituted or unsubstituted cycloalkyl group having 3 to 6 carbon atoms, or a substituted or unsubstituted aryl group having 6 to 13 carbon atoms. Furthermore, at least one of the following pairs may form a fused ring: $R^{12}$ and $R^{13}$; $R^{14}$ and $R^{15}$; $R^{15}$ and $R^{16}$; or $R^{16}$ and $R^{17}$. Furthermore, $X^2$ represents halogen, and the halogen is preferably iodine, bromine, and chlorine.

Examples of a palladium catalyst that can be used in the case where the Hartwig-Buchwald reaction is performed in the above synthesis scheme (A-2) includes bis(dibenzylideneacetone)palladium(0) and palladium(II) acetate. Note that examples of a ligand of the palladium catalyst that can be used in the synthesis scheme (A-2) include tri(tert-butyl)phosphine, tri(n-hexyl)phosphine, and tricyclohexylphosphine. Examples of the base that can be used in the synthesis scheme (A-2) include an organic base such as sodium tert-butoxide and an inorganic base such as potassium carbonate. Examples of the solvent that can be used in the synthesis scheme (A-2) include toluene, xylene, benzene, and tetrahydrofuran. Other than the Hartwig-Buchwald reaction, the Ullmann reaction or the like may be used, but not limited thereto.

Described above are the methods for synthesizing the organic compound which is an embodiment of the present invention and is represented by the general formula (G1); however, the present invention is not limited thereto and the organic compound may be synthesized by another synthesis method.

Note that the above-described organic compound of an embodiment of the present invention has an electron-transport property and a hole-transport property and thus can be used as a host material in a light-emitting layer or can be used in an electron-transport layer or a hole-transport layer. Furthermore, the organic compound is preferably used in combination with a substance that emits phosphorescence (phosphorescent material), as a host material. In addition, the organic compound emits fluorescence and can thus be used as a light-emitting substance of a light-emitting element. Accordingly, light-emitting elements containing these organic compounds are also included as embodiments of the present invention.

With the use of the organic compound of one embodiment of the present invention, a light-emitting element, a light-emitting device, an electronic device, or a lighting device having high emission efficiency can be fabricated. Furthermore, a light-emitting element, a light-emitting device, an electronic device, or a lighting device with low power consumption can be fabricated.

In this embodiment, one embodiment of the present invention has been described. Other embodiments of the present invention will be described in the other embodiments. However, embodiments of the present invention are not limited thereto. In other words, since various embodiments of the invention are described in this embodiment and the other embodiments, one embodiment of the present invention is not limited to a particular embodiment.

The structures described in this embodiment can be used in appropriate combination with any of the structures described in the other embodiments.

Embodiment 2

In this embodiment, a light-emitting element in which the organic compound described in Embodiment 1 is used will be described with reference to FIG. 1.

<<Basic Structure of Light-Emitting Element>>

First, a basic structure of a light-emitting element will be described. FIG. 1(A) illustrates a light-emitting element including, between a pair of electrodes, an EL layer having a light-emitting layer. Specifically, the light-emitting element has a structure in which an EL layer 103 is sandwiched between a first electrode 101 and a second electrode 102.

Figure 1B:
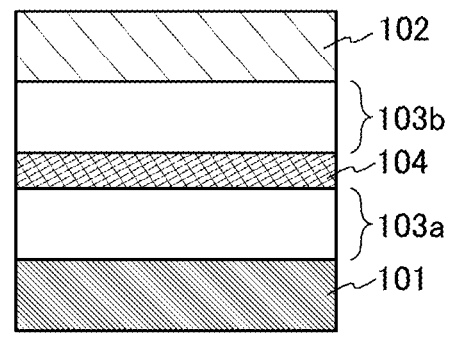

FIG. 1(B) illustrates a light-emitting element with a stacked-layer structure (tandem structure) in which a plurality of (two layers, in FIG. 1(B)) EL layers (103a and 103b) are provided between a pair of electrodes and a charge-generation layer 104 is provided between the EL layers. With a tandem light-emitting element, a light-emitting device that can be driven at low voltage with low power consumption can be obtained.

The charge-generation layer 104 has a function of injecting electrons into one of the EL layers (103a or 103b) and injecting holes into the other of the EL layers (103b or 103a) when voltage is applied to the first electrode 101 and the second electrode 102. Thus, when voltage is applied in FIG. 1(B) such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably has a light-transmitting property with respect to visible light (specifically, the visible light transmittance with respect to the charge-generation layer 104 is 40% or higher). Furthermore, the charge-generation layer 104 functions even when having lower conductivity than the first electrode 101 or the second electrode 102.

Figure 1C:
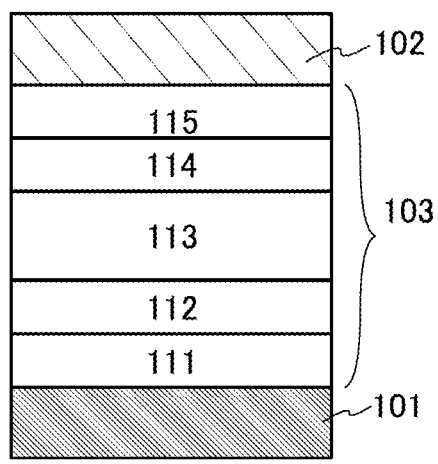

FIG. 1(C) illustrates a stacked-layer structure of the EL layer 103 in the light-emitting element of one embodiment of the present invention. In this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked sequentially over the first electrode 101. Even in the case where a plurality of EL layers are provided as in the tandem structure illustrated in FIG. 1(B), each EL layer has a structure in which layers are sequentially stacked from the anode side as described above. When the first electrode 101 is a cathode and the second electrode 102 is an anode, the stacking order is reversed.

The light-emitting layers 113 included in the EL layers (103, 103*a*, and 103*b*) each contain an appropriate combination of a light-emitting substance and a plurality of substances, so that fluorescence or phosphorescence with a desired emission color can be obtained. Furthermore, the light-emitting layer 113 may have a stacked-layer structure having different emission colors. In that case, different materials may be used for the light-emitting substance and other substances used in each of the light-emitting layers that are stacked. Alternatively, a structure in which different emission colors can be obtained from the plurality of EL layers (103*a* and 103*b*) shown in FIG. 1(B) may be employed. Also in that case, different materials may be used for the light-emitting substance and other substances used in each of the light-emitting layers.

In addition, the light-emitting element of one embodiment of the present invention can have a micro optical resonator (microcavity) structure with the first electrode 101 being a reflective electrode and the second electrode 102 being a semi-transmissive semi-reflective electrode in FIG. 1(C), for example, and light emission obtained from the light-emitting layer 113 in the EL layer 103 can be resonated between the electrodes and light emission obtained through the second electrode 102 can be intensified.

Note that when the first electrode 101 of the light-emitting element is a reflective electrode having a stacked structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is $\lambda$, the distance between the first electrode 101 and the second electrode 102 is preferably adjusted to around $m\lambda/2$ (m is a natural number).

To amplify desired light (wavelength: $\lambda$) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around $(2m'+1)\lambda/4$ (m' is a natural number). Here, the light-emitting region refers to a region where holes and electrons are recombined in the light-emitting layer 113.

By performing such optical adjustment, the spectrum of specific monochromatic light obtained from the light-emitting layer 113 can be narrowed and light emission with high color purity can be obtained.

However, in the above case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained with given positions in the first electrode 101 and the second electrode 102 being supposed to be reflective regions. Furthermore, the optical path length between the first electrode 101 and the light-emitting layer from which the desired light is obtained is, to be exact, the optical path length between the reflective region in the first electrode 101 and the light-emitting region in the light-emitting layer from which the desired light is obtained. However, it is difficult to precisely determine the reflective region in the first electrode 101 and the light-emitting region in the light-emitting layer from which the desired light is obtained; thus, it is assumed that the above effect can be sufficiently obtained with a given position in the first electrode 101 being supposed to be the reflective region and a given position in the light-emitting layer from which the desired light is obtained being supposed to be the light-emitting region.

The light-emitting element in FIG. 1(C) has a microcavity structure, so that light (monochromatic light) with different wavelengths can be extracted even if the same EL layer is included. Thus, separate coloring for obtaining a plurality of emission colors (e.g., R, G, and B) is not necessary. Therefore, high resolution can be easily achieved. Note that a combination with coloring layers (color filters) is also possible. Furthermore, emission intensity of light with a specific wavelength in the front direction can be increased, whereby power consumption can be reduced.

Figure 1D:
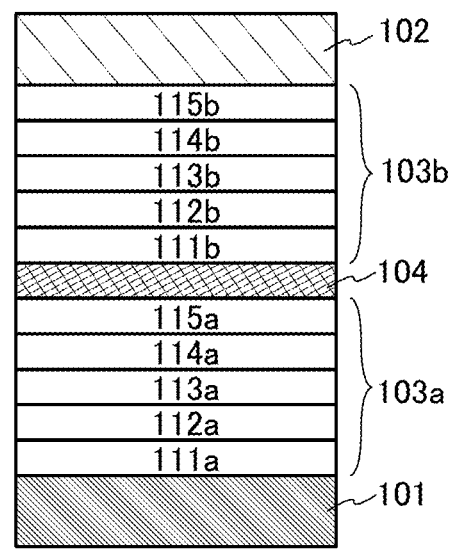
Figure 1E:
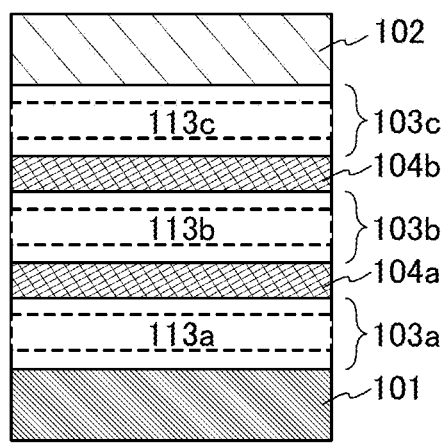

A light-emitting element illustrated in FIG. 1(E) is an example of the light-emitting element with the tandem structure illustrated in FIG. 1(B), and includes three EL layers (103*a*, 103*b*, and 103*c*) stacked with charge-generation layers (104*a* and 104*b*) sandwiched therebetween, as illustrated in the figure. Note that the three EL layers (103*a*, 103*b*, and 103*c*) include respective light-emitting layers (113*a*, 113*b*, and 113*c*) and the emission colors of the respective light-emitting layers can be combined freely. For example, the light-emitting layer 113*a* can be blue, the light-emitting layer 113*b* can be red, green, or yellow, and the light-emitting layer 113*c* can be blue; for another example, the light-emitting layer 113*a* can be red, the light-emitting layer 113*b* can be blue, green, or yellow, and the light-emitting layer 113*c* can be red.

In the above light-emitting element of one embodiment of the present invention, at least one of the first electrode 101 and the second electrode 102 is a light-transmitting electrode (a transparent electrode, a semi-transmissive semi-reflective electrode, or the like). In the case where the light-transmitting electrode is a transparent electrode, the visible light transmittance of the transparent electrode is 40% or higher. In the case where the light-transmitting electrode is a semi-transmissive semi-reflective electrode, the visible light reflectance of the semi-transmissive semi-reflective electrode is higher than or equal to 20% and lower than or equal to 80%, preferably higher than or equal to 40% and lower than or equal to 70%. The resistivity of these electrodes is preferably $1\times10^{-2}$ Ωcm or lower.

Furthermore, when one of the first electrode 101 and the second electrode 102 is a reflective electrode in the above light-emitting element of one embodiment of the present invention, the visible light reflectance of the reflective electrode is higher than or equal to 40% and lower than or equal to 100%, preferably higher than or equal to 70% and lower than or equal to 100%. The resistivity of this electrode is preferably $1\times10^{-2}$ Ωcm or lower.

<<Specific Structure and Fabrication Method of Light-Emitting Element>>

Next, specific structures and fabrication methods of light-emitting elements of embodiments of the present invention will be described with reference to FIG. 1. Here, a light-emitting element having the tandem structure shown in FIG. 1(B) and provided with a microcavity structure will also be described with reference to FIG. 1(D). In the case where the light-emitting element shown in FIG. 1(D) has a microcavity structure, the first electrode 101 is formed as a reflective electrode and the second electrode 102 is formed as a semi-transmissive semi-reflective electrode. Thus, the electrode can be formed, using one or more kinds of desired electrode materials, as a single layer or a stacked layer. Note that the second electrode 102 is formed after formation of the EL layer 103b, with the use of a material selected as described above. For fabrication of these electrodes, a sputtering method or a vacuum evaporation method can be used.

<First Electrode and Second Electrode>

As materials used for the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be used as appropriate. Specifically, an In—Sn oxide (also referred to as ITO), an In-Si-Sn oxide (also referred to as ITSO), an In—Zn oxide, and an In—W—Zn oxide can be given as examples. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use an element belonging to Group 1 or Group 2 in the periodic table, which is not listed above (for example, lithium (Li), cesium (Cs), calcium (Ca), or strontium (Sr)), a rare earth metal such as europium (Eu) or ytterbium (Yb), an alloy containing an appropriate combination of any of these elements, graphene, or the like.

In the light-emitting element shown in FIG. 1(D), when the first electrode 101 is an anode, a hole-injection layer 111a and a hole-transport layer 112a of the EL layer 103a are sequentially formed and stacked over the first electrode 101 by the vacuum evaporation method. After the EL layer 103a and the charge-generation layer 104 are formed, a hole-injection layer 111b and a hole-transport layer 112b of the EL layer 103b are sequentially formed and stacked over the charge-generation layer 104 in a similar manner.

<Hole-Injection Layer and Hole-Transport Layer>

The hole-injection layers (111, 111a, and 111b) are each a layer that injects holes from the first electrode 101 which is an anode and the charge-generation layer (104) to the EL layers (103, 103a, and 103b) and contains a material with a high hole-injection property.

As examples of the material with a high hole-injection property, transition metal oxides such as a molybdenum oxide, a vanadium oxide, a ruthenium oxide, a tungsten oxide, and a manganese oxide can be given. Other than the above, it is possible to use phthalocyanine-based compounds such as phthalocyanine (abbreviation: H$_2$Pc) and copper phthalocyanine (abbreviation: CuPc); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD); macromolecules such as poly(3,4-ethylenedioxythiophene)/poly(styrenesulfonic acid) (abbreviation: PEDOT/PSS); or the like.

Alternatively, as the material with a high hole-injection property, a composite material containing a hole-transport material and an acceptor material (an electron-accepting material) can be used. In that case, the acceptor material extracts electrons from the hole-transport material, so that holes are generated in the hole-injection layers (111, 111a, and 111b) and the holes are injected into the light-emitting layers (113, 113a, and 113b) through the hole-transport layers (112, 112a, and 112b). Note that each of the hole-injection layers (111, 111a, and 111b) may be formed as a single layer formed of a composite material containing a hole-transport material and an acceptor material (electron-accepting material), or may be formed by stacking a layer including a hole-transport material and a layer including an acceptor material (electron-accepting material).

The hole-transport layers (112, 112a, and 112b) transport the holes, which are injected from the first electrode 101 or the charge-generation layer 104 by the hole-injection layers (111, 111a, and 111b), to the light-emitting layers (113, 113a, and 113b). Note that the hole-transport layers (112, 112a, and 112b) each contain a hole-transport material. It is particularly preferable that the HOMO level of the hole-transport material used in the hole-transport layers (112, 112a, and 112b) be the same as or close to the HOMO level of the hole-injection layers (111, 111a, and 111b).

As the acceptor material used in the hole-injection layers (111, 111a, and 111b), an oxide of a metal belonging to any of Groups 4 to 8 of the periodic table can be used. Specific examples include molybdenum oxide, vanadium oxide, niobium oxide, tantalum oxide, chromium oxide, tungsten oxide, manganese oxide, and rhenium oxide. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), and the like can be used. A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferred; specific examples include α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], and α,α∝,α''-1,2,3-cyclopropanetriylidenetris[2,3,4,5,6-pentafluorobenzeneacetonitrile].

The hole-transport materials used for the hole-injection layers (111, 111a, and 111b) and the hole-transport layers (112, 112a, and 112b) are preferably substances with a hole mobility of greater than or equal to $10^{-6}$ cm$^2$/Vs. Note that other substances may be used as long as the substances have a hole-transport property higher than an electron-transport property.

Preferred hole-transport materials are π-electron rich heteroaromatic compounds (e.g., carbazole derivatives and indole derivatives) and aromatic amine compounds, examples of which include compounds having an aromatic amine skeleton, such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 4,4',4"-tris(carbazol-9-yl)triphenylamine (abbreviation: TCTA), 4,4',4"-tris(N,N-diphenylamino)triphenylamine (abbreviation: TDATA), and 4,4',4"-tris[N-(3-methylphenyl)-N-phenylamino]triphenylamine (abbreviation: MTDATA); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA); compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Furthermore, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Note that the hole-transport material is not limited to the above examples and one of or a combination of various known materials can be used as the hole-transport material for the hole-injection layers (111, 111a, and 111b) and the hole-transport layers (112, 112a, and 112b). Note that the hole-transport layers (112, 112a, and 112b) may each be formed of a plurality of layers. That is, a first hole-transport layer and a second hole-transport layer may be stacked, for example.

In the light-emitting element in FIG. 1(D), the light-emitting layer 113a is formed over the hole-transport layer 112a of the EL layer 103a by the vacuum evaporation method. After the EL layer 103a and the charge-generation layer 104 are formed, the light-emitting layer 113b is formed over the hole-transport layer 112b of the EL layer 103b by the vacuum evaporation method.

<Light-Emitting Layer>

The light-emitting layers (113, 113a, 113b, and 113c) each contain a light-emitting substance. Note that as the light-emitting substance, a substance that exhibits emission color of blue, purple, bluish purple, green, yellowish green, yellow, orange, red, or the like is appropriately used. When the light-emitting layers (113a, 113b, and 113c) are formed using different light-emitting substances, different emission colors can be exhibited (for example, complementary emission colors are combined to obtain white light emission). Furthermore, a stacked-layer structure in which one light-emitting layer contains different light-emitting substances may be employed.

The light-emitting layers (113, 113a, 113b, and 113c) may each contain one or more kinds of organic compounds (a host material and an assist material) in addition to a light-emitting substance (guest material). As the one or more kinds of organic compounds, one or both of the hole-transport material and the electron-transport material described in this embodiment can be used.

Note that, as the light-emitting substance that can be used in the light-emitting layers (113, 113a, 113b, and 113c), a light-emitting substance that converts singlet excitation energy into light emission in the visible light range, a light-emitting substance that converts triplet excitation energy into light emission in the visible light range, or the like can be used.

Examples of other light-emitting substances are given below.

As an example of the light-emitting substance that converts singlet excitation energy into light emission, a substance that emits fluorescence (fluorescent material) can be given; examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine](abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As examples of the light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit different emission colors (emission peaks) and thus, any of them is selected and used appropriately according to need.

As a phosphorescent material that emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-$\kappa N^2$]phenyl-$\kappa C$}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)); and the like can be given.

As a phosphorescent material that emits green or yellow light and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-$\kappa N^3$]phenyl-$\kappa C$}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato)(monophenanthroline)terbium(III) (abbreviation: [Tb(acac)$_3$(Phen)]) can be given.

As a phosphorescent material that emits yellow or red light and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato] (dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(d1npm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-$\kappa N$]phenyl-$\kappa C$} (2,6-dimethyl-3,5-heptanedionato-$\kappa^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-$\kappa N$]phenyl-$\kappa C$}(2,2,6,6-tetramethyl-3,5-heptanedionato-$\kappa^2$O,O')iridium(III) (abbreviation: [Ir(dmdppr-dmCP)$_2$(dpm)]), (acetylacetonato)bis[2-methyl-3-phenylquinoxalinato-N,C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]

iridium(III) (abbreviation: [Ir(Fdpq)₂(acac)]); organometallic complexes having a pyridine skeleton, such as tris(1-phenylisoquinolinato-N,C²')iridium(III) (abbreviation: [Ir(piq)₃]) and bis(1-phenylisoquinolinato-N,C²')iridium(III) acetylacetonate (abbreviation: [Ir(piq)₂(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1, 3-propanedionato) (monophenanthroline)europium(III) (abbreviation: [Eu(DBM)₃(Phen)]) and tris[1-(2-thenoyl)-3,3, 3-trifluoroacetonato] (monophenanthroline)europium(III) (abbreviation: [Eu(TTA)₃(Phen)]) can be given.

As the organic compounds (the host material and the assist material) used in the light-emitting layers (113, 113a, 113b, and 113c), one or more kinds of substances having a larger energy gap than the light-emitting substance (the guest material) are selected to be used.

In the case where the light-emitting substance is a fluorescent material, it is preferable to use, as the host material, an organic compound that has a high energy level in a singlet excited state and has a low energy level in a triplet excited state. For example, an anthracene derivative or a tetracene derivative is preferably used. Specifically, 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene, and the like can be given.

In the case where the light-emitting substance is a phosphorescent material, an organic compound having triplet excitation energy (energy difference between a ground state and a triplet excited state) which is higher than the triplet excitation energy of the light-emitting substance is preferably selected as the host material. In that case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, and the like.

More specifically, any of the following hole-transport materials and electron-transport materials can be used as the host material, for example.

Examples of the host material having a high hole-transport property include aromatic amine compounds such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-di amine (abbreviation: DNTPD), and 1,3,5-tris[N-(4-diphenylaminophenyl)-N-phenylamino]benzene (abbreviation: DPA3B).

Carbazole derivatives such as 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1) are also given. In addition, as the carbazole derivative, 4,4'-di(N-carbazolyl)biphenyl (abbreviation: CBP), 1,3,5-tris[4-(N-carbazolyl)phenyl]benzene (abbreviation: TCPB), and 1,4-bis[4-(N-carbazolyl)phenyl]-2,3,5,6-tetraphenylbenzene can also be used.

Examples of the host material having a high hole-transport property include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris (carbazol-9-yl)triphenylamine (abbreviation: TCTA), 4,4',4''-tris[N-(1-naphthyl)-N-phenylamino]triphenylamine (abbreviation: 1'-TNATA), 4,4',4''-tris(N,N-diphenylamino)triphenylamine (abbreviation: TDATA), 4,4', 4''-tris[N-(3-methylphenyl)-N-phenylamino]triphenylamine (abbreviation: m-MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N''-triphenyl-N,N',N''-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-di amine (abbreviation: YGA2F). Furthermore, carbazole compounds, thiophene compounds, furan compounds, fluorene compounds, triphenylene compounds, phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 4-{3-[3-(9-phenyl-9H-fluoren-9-yl)phenyl]phenyl}dibenzofuran (abbreviation: mmDBFFLBi-II), 4,4',4''-(benzene-1,3,5-triyl)tri(dibenzofuran) (abbreviation: DBF3P-II), 1,3,5-tri(dibenzothiophen-4-yl)-benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II) can also be used.

Examples of the host material having a high electron-transport property include a metal complex having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), or bis (8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ), or the like can also be used. Other than metal complexes, any of the following can be used: oxadiazole derivatives such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), and 9-[4-(5-phenyl-1,3,4-oxadiazol-2-yl)phenyl]-9H-carbazole (abbreviation: CO11); a triazole derivative such as 3-(4-biphenylyl)-4-phenyl-5-(4-tert-butylphenyl)-1,2,4-triazole (abbreviation: TAZ); a compound having an imidazole skeleton (in particular, a benzimidazole derivative) such as 2,2',2''-(1,3,5-benzenetriyl)tris(1-phenyl-1H-benzimidazole) (abbreviation: TPBI) or 2-[3-(dibenzothiophen-4-yl)phenyl]-1-phenyl-1H-benzimidazole (abbreviation: mDBTBIm-II); a compound having an oxazole skeleton (in particular, a benzoxazole derivative) such as 4,4'-bis(5-methylbenzoxazol-2-yl)stilbene (abbreviation: BzOs); a phenanthroline derivative such as bathophenanthroline (abbreviation: Bphen), bathocuproine (abbreviation: BCP), and 2,9-bis(naphthalen-2-yl)-4,7-diphenyl-1,10-phenanthroline (abbreviation: NBphen); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl] dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having a pyridine skeleton such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used.

Examples of the host material include condensed polycyclic aromatic compounds such as anthracene derivatives, phenanthrene derivatives, pyrene derivatives, chrysene derivatives, and dibenzo[g,p]chrysene derivatives; specifically, 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), 2PCAPA, 6,12-dimethoxy-5,11-diphenylchrysene, DBC 1, 9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), and the like can be used.

In the case where a plurality of organic compounds are used in the light-emitting layers (113, 113*a*, 113*b*, and 113*c*), two kinds of compounds that form an exciplex (a first compound and a second compound) and an organometallic complex may be mixed and used. In that case, various organic compounds can be combined appropriately to be used; to form an exciplex efficiently, it is particularly preferable to combine a compound that easily accepts holes (hole-transport material) and a compound that easily accepts electrons (electron-transport material). Note that, as specific examples of the hole-transport material and the electron-transport material, the materials described in this embodiment can be used. With the above structure, high efficiency, low voltage, and a long lifetime can be achieved at the same time.

The TADF material refers to a material that can up-convert a triplet excited state into a singlet excited state (i.e., reverse intersystem crossing is possible) using a little thermal energy and efficiently emit light (fluorescence) from the singlet excited state. As the condition under which the thermally activated delayed fluorescence is efficiently obtained, energy difference between the triplet excited level and the singlet excited level being greater than or equal to 0 eV and less than or equal to 0.2 eV, preferably greater than or equal to 0 eV and less than or equal to 0.1 eV can be given. Note that "delayed fluorescence" exhibited by the TADF material refers to light emission having a spectrum similar to that of normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. In addition, a metal-containing porphyrin containing magnesium (Mg), zinc (Zn), cadmium (Cd), tin (Sn), platinum (Pt), indium (In), palladium (Pd), or the like is also given. Examples of the metal-containing porphyrin include a protoporphyrin-tin fluoride complex (abbreviation: SnF$_2$ (Proto IX)), a mesoporphyrin-tin fluoride complex (abbreviation: SnF$_2$(Meso IX)), a hematoporphyrin-tin fluoride complex (abbreviation: SnF$_2$(Hemato IX)), a coproporphyrin tetramethyl ester-tin fluoride complex (abbreviation: SnF$_2$(Copro III-4Me)), an octaethylporphyrin-tin fluoride complex (abbreviation: SnF$_2$(OEP)), an etioporphyrin-tin fluoride complex (abbreviation: SnF$_2$(Etio I)), and an octaethylporphyrin-platinum chloride complex (abbreviation: PtCl$_2$OEP).

Other than these, a heterocyclic compound having a π-electron rich heteroaromatic ring and a π-electron deficient heteroaromatic ring, such as 2-(biphenyl-4-yl)-4,6-bis(12-phenylindolo[2,3-α]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that in the case where a TADF material is used, the TADF material can be used in combination with another organic compound.

In the light-emitting element illustrated in FIG. 1(D), an electron-transport layer 114a is formed over the light-emitting layer 113a of the EL layer 103a by the vacuum evaporation method. After the EL layer 103a and the charge-generation layer 104 are formed, an electron-transport layer 114b is formed over the light-emitting layer 113b of the EL layer 103b by the vacuum evaporation method.

<Electron-Transport Layer>

The electron-transport layers (114, 114a, and 114b) are each a layer that transports the electrons, which are injected from the second electrode 102 and the charge-generation layer 104 by the electron-injection layers (115, 115a, and 115b), to the light-emitting layers (113, 113a, and 113b). Note that the electron-transport layers (114, 114a, and 114b) are each a layer containing an electron-transport material. It is preferable that the electron-transport materials used in the electron-transport layers (114, 114a, and 114b) be substances with an electron mobility of higher than or equal to $1 \times 10^{-6}$ cm$^2$/Vs. Note that other substances may also be used as long as the substances have an electron-transport property higher than a hole-transport property.

Examples of the electron-transport material include a metal complex having a quinoline ligand, a benzoquinoline ligand, an oxazole ligand, or a thiazole ligand; an oxadiazole derivative; a triazole derivative; a phenanthroline derivative; a pyridine derivative; and a bipyridine derivative. In addition, a π-electron deficient heteroaromatic compound such as a nitrogen-containing heteroaromatic compound can also be used.

Specifically, it is possible to use metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, bis[2-(2-hydroxyphenyl)benzoxazolato]zinc(II) (abbreviation: Zn(BOX)$_2$), and bis[2-(2-hydroxyphenyl)benzothiazolato]zinc(II) (abbreviation: Zn(BTZ)$_2$), heteroaromatic compounds such as 2-(4-biphenylyl)-5-(4-tert-butylphenyl)-1,3,4-oxadiazole (abbreviation: PBD), OXD-7, 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), and 4,4'-bis(5-methylbenzoxazol-2-yl)stilbene (abbreviation: BzOs), and quinoxaline derivatives and dibenzoquinoxaline derivatives such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used.

Each of the electron-transport layers (114, 114a, and 114b) is not limited to a single layer, and may be a stack of two or more layers each made of any of the above substances.

In the light-emitting element illustrated in FIG. 1(D), the electron-injection layer 115a is formed over the electron-transport layer 114a of the EL layer 103a by the vacuum evaporation method. After that, the EL layer 103a and the charge-generation layer 104 are formed, the components up to the electron-transport layer 114b of the EL layer 103b are formed, and then the electron-injection layer 115b is formed thereover by the vacuum evaporation method.

<Electron-Injection Layer>

The electron-injection layers (115, 115a, and 115b) are each a layer containing a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride (CaF$_2$), or lithium oxide (LiO$_x$). A rare earth metal compound such as erbium fluoride (ErF$_3$) may also be used. Electride may also be used for the electron-injection layers (115, 115a, and 115b). Examples of the electride include a substance in which electrons are added at high concentration to a mixed oxide of calcium and aluminum. Note that any of the substances used in the electron-transport layers (114, 114a, and 114b), which are given above, may also be used.

A composite material in which an organic compound and an electron donor (donor) are mixed may also be used in the electron-injection layers (115, 115a, and 115b). Such a composite material is excellent in an electron-injection property and an electron-transport property because electrons are generated in the organic compound by the electron donor. In this case, the organic compound is preferably a material excellent in transporting the generated electrons; specifically, for example, the above-mentioned electron-transport materials (metal complexes, heteroaromatic compounds, and the like) used in the electron-transport layers (114, 114a, and 114b) can be used. Any substance showing an electron-donating property with respect to the organic compound can serve as an electron donor. Specifically, an alkali metal, an alkaline earth metal, and a rare earth metal are preferable, and lithium, cesium, magnesium, calcium, erbium, ytterbium, and the like are given as examples. In addition, an alkali metal oxide and an alkaline earth metal oxide are preferable, and lithium oxide, calcium oxide, barium oxide, and the like are given as examples. A Lewis base such as magnesium oxide can also be used. An organic compound such as tetrathiafulvalene (abbreviation: TTF) can also be used.

Note that in the case where light obtained from the light-emitting layer 113b is amplified, for example, the optical path length between the second electrode 102 and the light-emitting layer 113b is preferably less than one fourth of the wavelength X of light emitted from the light-emitting layer 113b. In that case, the optical path length can be adjusted by changing the thickness of the electron-transport layer 114b or the electron-injection layer 115b.

<Charge-Generation Layer>

The charge-generation layer 104 has a function of injecting electrons into the EL layer 103a and injecting holes into the EL layer 103b when voltage is applied across the first electrode (anode) 101 and the second electrode (cathode) 102. Note that the charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 with the use of any of the above materials can suppress an increase in drive voltage caused by the stack of the EL layers.

In the case where the charge-generation layer 104 has a structure in which an electron acceptor is added to a hole-transport material, any of the materials described in this embodiment can be used as the hole-transport material. As the electron acceptor, 7,7,8,8-tetracyano-2,3,5,6-tetrafluoro-quinodimethane (abbreviation: $F_4$-TCNQ), chloranil, and the like can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, rhenium oxide, and the like can be given.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or a carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that the EL layer 103c in FIG. 1(E) has a structure similar to those of the above-described EL layers (103, 103a, and 103b). In addition, the charge-generation layers 104a and 104b each have a structure similar to that of the above-described charge-generation layer 104.

<Substrate>

The light-emitting element described in this embodiment can be formed over any of a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, a laminate film, paper including a fibrous material, and a base material film.

Note that examples of the glass substrate include barium borosilicate glass, aluminoborosilicate glass, and soda lime glass. Examples of the flexible substrate, the laminate film, and the base material film include plastics typified by polyethylene terephthalate (PET), polyethylene naphthalate (PEN), and polyether sulfone (PES); a synthetic resin such as acrylic; polypropylene; polyester; polyvinyl fluoride; polyvinyl chloride; polyamide; polyimide; aramid; epoxy; an inorganic vapor deposition film; and paper.

Note that for fabrication of the light-emitting element described in this embodiment, a vacuum process such as an evaporation method or a solution process such as a spin coating method or an ink-jet method can be used. In the case where an evaporation method is used, a physical vapor deposition method (PVD method) such as a sputtering method, an ion plating method, an ion beam evaporation method, a molecular beam evaporation method, or a vacuum evaporation method; a chemical vapor deposition method (CVD method); or the like can be used. Specifically, the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), the electron-injection layers (115, 115a, and 115b)) included in the EL layers and the charge-generation layers (104, 104a, and 104b) of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

Note that materials that can be used for the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) that are included in the EL layers (103, 103a, and 103b) and the charge-generation layers (104, 104a, and 104b) of the light-emitting element described in this embodiment are not limited to the above materials, and other materials can also be used in combination as long as the functions of the layers are fulfilled. For example, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) can be used. Note that as the quantum dot material, a colloidal quantum dot material, an alloyed quantum dot material, a core-shell quantum dot material, a core quantum dot material, or the like can be used.

Note that the structure described in this embodiment can be used in an appropriate combination with any of the structures described in the other embodiments.

Embodiment 3

Figure 2A:
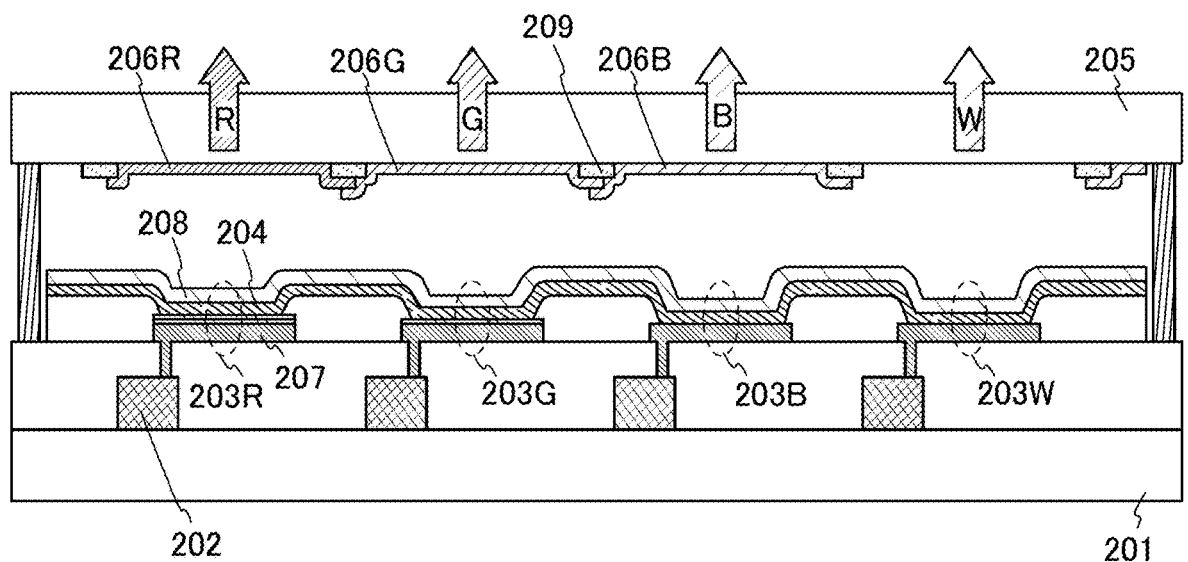
FIGS. 2A-2C Drawings illustrating light-emitting devices.

In this embodiment, a light-emitting device of one embodiment of the present invention will be described. Note that a light-emitting device illustrated in FIG. 2(A) is an active-matrix light-emitting device in which transistors (FETs) 202 over a first substrate 201 are electrically connected to light-emitting elements (203R, 203G, 203B, and 203W); the light-emitting elements (203R, 203G, 203B, and 203W) include a common EL layer 204 and each have a microcavity structure in which the optical path length between electrodes is adjusted according to the emission color of the light-emitting element. In addition, the light-emitting device is a top-emission light-emitting device in which light is emitted from the EL layer 204 through color filters (206R, 206G, and 206B) formed on a second substrate 205.

In the light-emitting device illustrated in FIG. 2(A), the first electrode 207 is formed so as to function as a reflective electrode. The second electrode 208 is formed so as to function as a semi-transmissive and semi-reflective electrode. Note that description in any of the other embodiments can be referred to as appropriate for electrode materials forming the first electrode 207 and the second electrode 208.

Figure 2B:
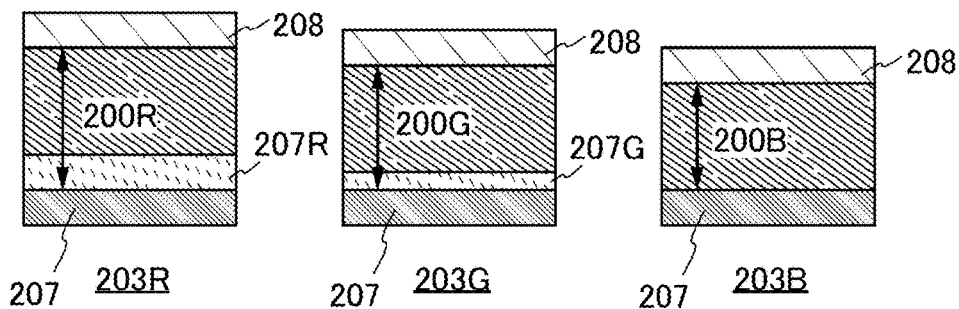

In the case where the light-emitting element 203R is a red light-emitting element, the light-emitting element 203G is a green light-emitting element, the light-emitting element 203B is a blue light-emitting element, and the light-emitting element 203W is a white light-emitting element in FIG. 2(A), for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2(B). Note that optical adjustment can be performed in such a manner that a conductive layer 207R is stacked over the first electrode 207 in the light-emitting element 203R and a conductive layer 207G is stacked over the first electrode 207 in the light-emitting element 203G as illustrated in FIG. 2(B).

The color filters (206R, 206G, and 206B) are formed on the second substrate 205. Note that the color filters each transmit visible light in a specific wavelength range and blocks visible light in a specific wavelength range. Thus, as illustrated in FIG. 2(A), the color filter 206R that transmits only light in the red wavelength range is provided in a position overlapping with the light-emitting element 203R, whereby red light emission can be obtained from the light-emitting element 203R. Similarly, the color filter 206G that transmits only light in the green wavelength range is provided in a position overlapping with the light-emitting element 203G, whereby green light emission can be obtained from the light-emitting element 203G. Similarly, the color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of each color filter. The color filters (206R, 206G, and 206B) and the black layer 209 may be covered with an overcoat layer using a transparent material.

Figure 2C:
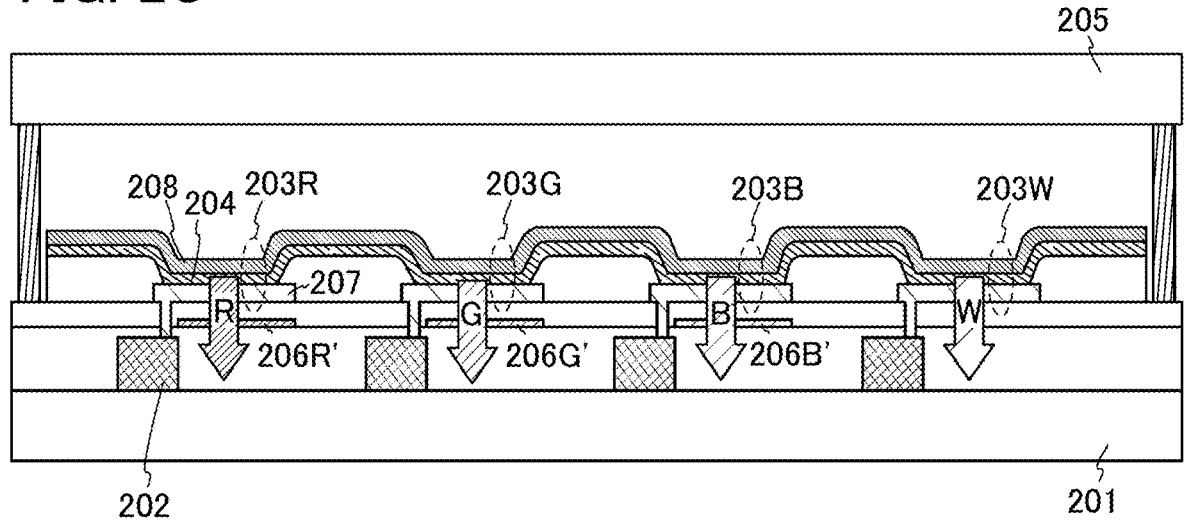

Although the light-emitting device illustrated in FIG. 2(A) has a structure in which light is extracted from the second substrate 205 side (top emission structure), the light-emitting device may have a structure in which light is extracted from the first substrate 201 side where the FETs 202 are formed (bottom emission structure) as illustrated in FIG. 2(C). For a bottom-emission light-emitting device, the first electrode 207 is formed so as to function as a semi-transmissive and semi-reflective electrode and the second electrode 208 is formed so as to function as a reflective electrode. As the first substrate 201, a substrate having at least a light-transmitting property is used. As illustrated in FIG. 2(C), color filters (206W, 206G', and 206W) are provided closer to the first substrate 201 than the light-emitting elements (203R, 203G, and 203B) are.

In FIG. 2(A), the light-emitting elements are the red light-emitting element, the green light-emitting element, the blue light-emitting element, and the white light-emitting element; however, the light-emitting elements of one embodiment of the present invention are not limited to the above, and a yellow light-emitting element or an orange light-emitting element may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting elements. In that case, a color filter needs to be appropriately selected according to the emission color of the light-emitting element.

With the above structure, a light-emitting device including light-emitting elements that exhibit a plurality of emission colors can be obtained.

Note that the structures described in this embodiment can be used in an appropriate combination with any of the structures described in the other embodiments.

Embodiment 4

In this embodiment, a light-emitting device of one embodiment of the present invention will be described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is included in one embodiment of the present invention. Note that any of the light-emitting elements described in the other embodiments can be used in the light-emitting device described in this embodiment.

In this embodiment, an active-matrix light-emitting device will be described with reference to FIG. 3.

Figure 3A:
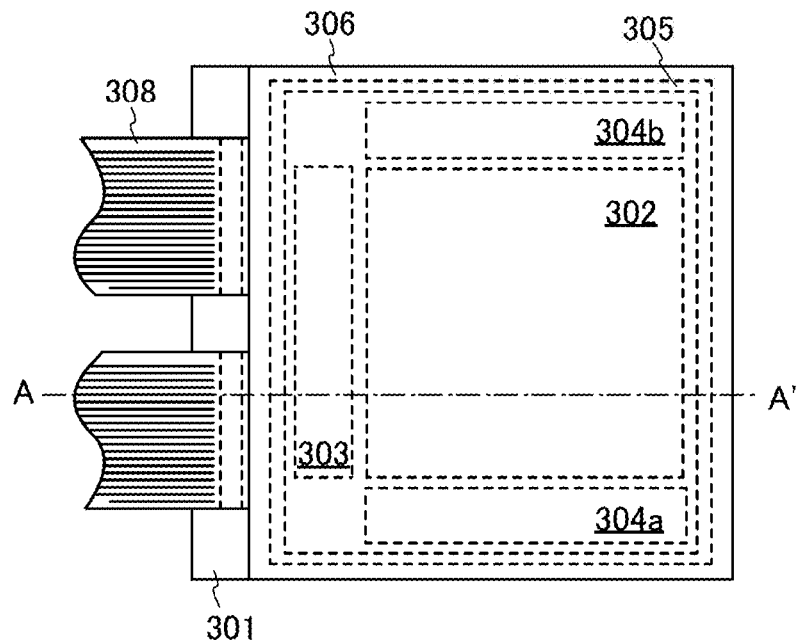
FIGS. 3A and 3B Drawings illustrating a light-emitting device.
Figure 3B:
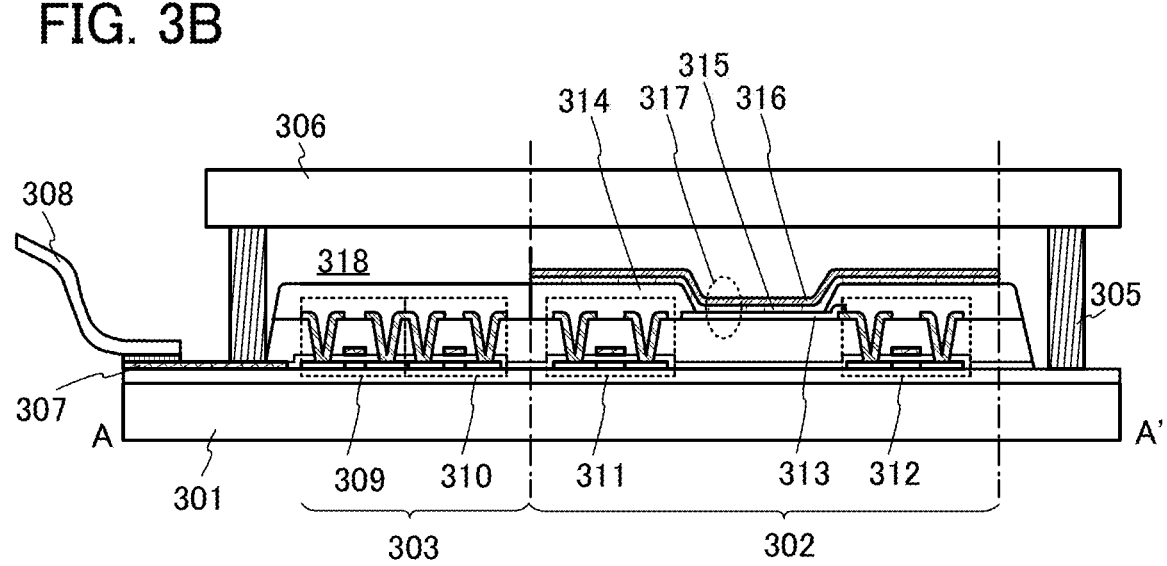

FIG. 3(A) is a top view illustrating the light-emitting device, and FIG. 3(B) is a cross-sectional view cut along a chain line A-A' in FIG. 3(A). The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is connected to an FPC 308 which is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

Next, FIG. 3(B) illustrates the cross-sectional structure.

The pixel portion 302 is made up of a plurality of pixels each of which includes an FET (switching FET) 311, an FET (current control FET) 312, and a first electrode 313 electrically connected to the FET 312. Note that the number of FETs included in each pixel is not particularly limited and can be set appropriately as needed.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

For these semiconductors, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a structure including a driver circuit outside may be employed.

An end portion of the first electrode 313 is covered with an insulator 314. For the insulator 314, an organic compound such as a negative photosensitive resin or a positive photosensitive resin (acrylic resin), or an inorganic compound such as silicon oxide, silicon oxynitride, or silicon nitride can be used. An upper end portion or a lower end portion of the insulator 314 preferably has a curved surface with curvature. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the structure of a light-emitting element 317 described in this embodiment. Although not illustrated here, the second electrode 316 is electrically connected to the FPC 308 which is an external input terminal.

Although the cross-sectional view in FIG. 3(B) illustrates only one light-emitting element 317, a plurality of light-emitting elements are arranged in a matrix in the pixel portion 302. Light-emitting elements from which light of three kinds of colors (R, G, and B) are obtained are selectively formed in the pixel portion 302, whereby a light-emitting device capable of full-color display can be formed. In addition to the light-emitting elements from which light of three kinds of colors (R, G, and B) are obtained, for example, light-emitting elements from which light of white (W), yellow (Y), magenta (M), cyan (C), and the like are obtained may be formed. For example, the light-emitting elements from which light of some of the above colors are obtained are added to the light-emitting elements from which light of three kinds of colors (R, G, and B) are obtained, whereby effects such as an improvement in color purity and a reduction in power consumption can be obtained. Alternatively, a light-emitting device that is capable of full-color display may be fabricated by a combination with color filters. As the colors of color filters, red (R), green (G), blue (B), cyan (C), magenta (M), yellow (Y), and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy-based resin, glass frit, or the like can be used for the sealant 305. It is preferable to use a material that is permeable to as little moisture and oxygen as possible for the sealant 305. As the second substrate 306, a material that can be used as the first substrate 301 can be similarly used. Thus, any of the various substrates described in the other embodiments can be appropriately used. As the substrate, a glass substrate, a quartz substrate, or a plastic substrate made of FRP (fiber-reinforced plastic), PVF (polyvinyl fluoride), polyester, acrylic, or the like can be used. In the case where glass frit is used for the sealant, the first substrate 301 and the second substrate 306 are preferably glass substrates in terms of adhesion.

In the above manner, the active-matrix light-emitting device can be obtained.

In the case where the active-matrix light-emitting device is formed over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, an increase in durability, an increase in heat resistance, a reduction in weight, and a reduction in thickness can be achieved.

Note that the structures described in this embodiment can be used in an appropriate combination with any of the structures described in the other embodiments.

Embodiment 5

In this embodiment, examples of a variety of electronic devices and an automobile completed using the light-emitting device of one embodiment of the present invention or a display device including the light-emitting element of one embodiment of the present invention are described.

Electronic devices illustrated in FIG. 4(A) to FIG. 4(E) can include a housing 7000, a display portion 7001, a speaker 7003, an LED lamp 7004, operation keys 7005 (including a power switch or an operation switch), a connection terminal 7006, a sensor 7007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), microphones 7008 and 7019, and the like.

Figure 4A:
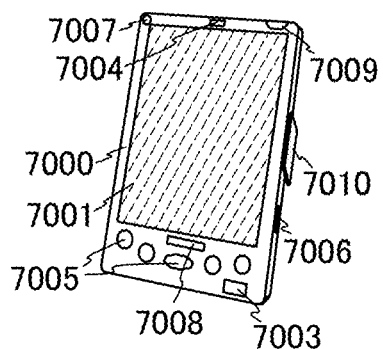
FIGS. 4A-4G Drawings illustrating electronic devices.

FIG. 4(A) is a mobile computer which can include a switch 7009, an infrared port 7010, and the like in addition to the above components.

Figure 4B:
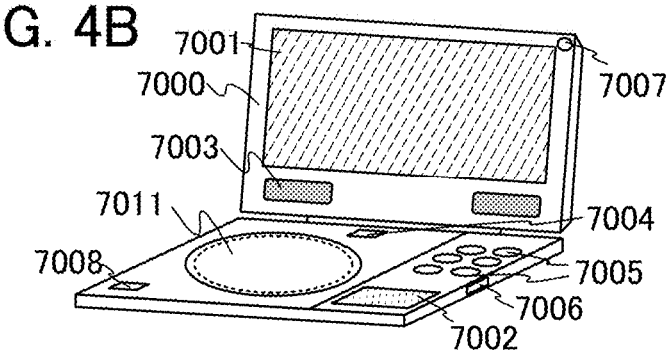

FIG. 4(B) is a portable image reproducing device (e.g., a DVD player) which is provided with a recording medium and can include a second display portion 7002, a recording medium reading portion 7011, and the like in addition to the above components.

Figure 4C:
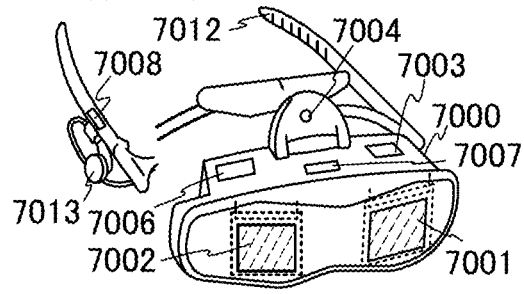

FIG. 4(C) is a goggle-type display which can include the second display portion 7002, a support portion 7012, an earphone 7013, and the like in addition to the above components.

Figure 4D:
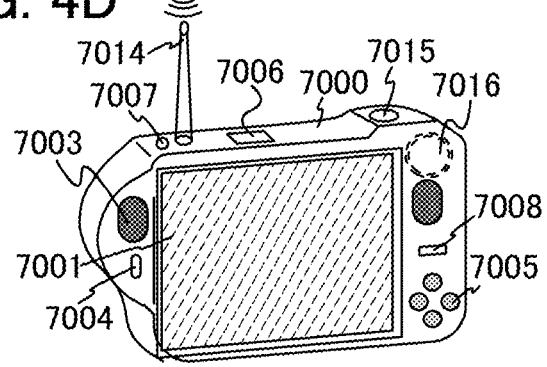

FIG. 4(D) is a digital camera with a television reception function, which can include an antenna 7014, a shutter button 7015, an image receiving portion 7016, and the like in addition to the above components.

Figure 4E:
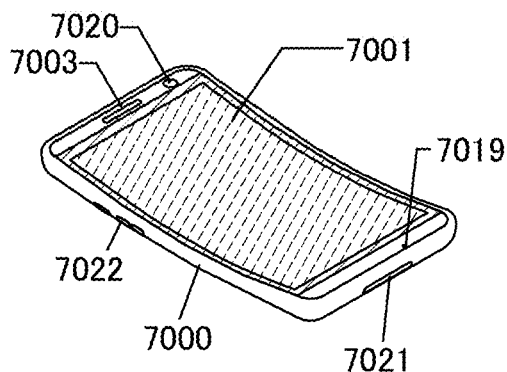

FIG. 4(E) is a cellular phone (including a smartphone) which can include the display portion 7001, the microphone 7019, the speaker 7003, a camera 7020, an external connection portion 7021, an operation button 7022, and the like in the housing 7000.

Figure 4F:
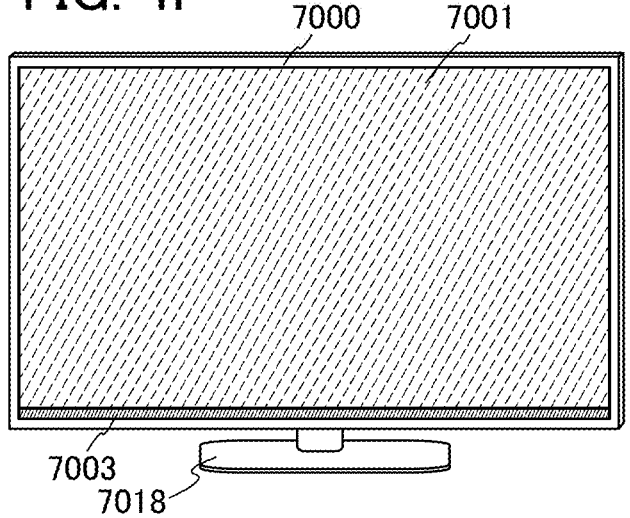

FIG. 4(F) is a large-size television set (also referred to as TV or a television receiver), which can include the housing 7000, the display portion 7001, the speaker 7003, and the like. In addition, shown here is a structure where the housing 7000 is supported by a stand 7018.

The electronic devices illustrated in FIG. 4(A) to FIG. 4(F) can have a variety of functions. For example, they can have a function of displaying a variety of data (e.g., a still image, a moving image, and a text image) on the display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion. Furthermore, the electronic device including a plurality of display portions can have a function of displaying image data mainly on one display portion while displaying text data mainly on the other display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that the electronic devices illustrated in FIG. 4(A) to FIG. 4(F) can have are not limited to those described above, and the electronic devices can have a variety of functions.

Figure 4G:
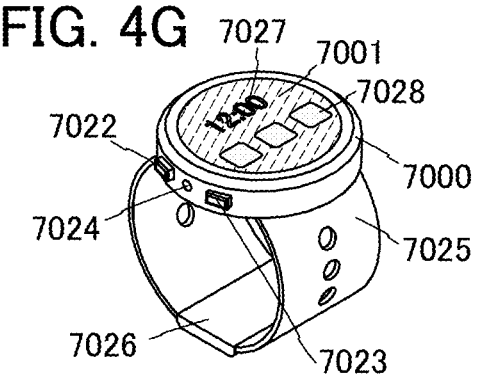

FIG. 4(G) is a smart watch, which includes the housing 7000, the display portion 7001, operation buttons 7022 and 7023, a connection terminal 7024, a band 7025, a clasp 7026, and the like.

The display portion 7001 mounted in the housing 7000 also serving as a bezel includes a non-rectangular display region. The display portion 7001 can display an icon 7027 indicating time, another icon 7028, and the like. The display portion 7001 may be a touch panel (input/output device) including a touch sensor (input device).

Note that the smart watch illustrated in FIG. 4(G) can have a variety of functions. For example, the smart watch can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion.

Moreover, a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like can be included inside the housing 7000.

Note that the light-emitting device of one embodiment of the present invention and the display device including the light-emitting element of one embodiment of the present invention can be used in the display portion of each electronic device described in this embodiment, enabling display with high color purity.

Figure 5A:
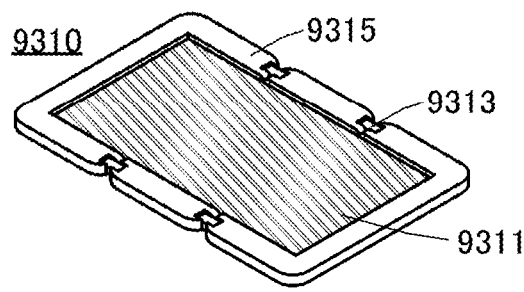
FIGS. 5A-5C Drawings illustrating an electronic device.
Figure 5B:
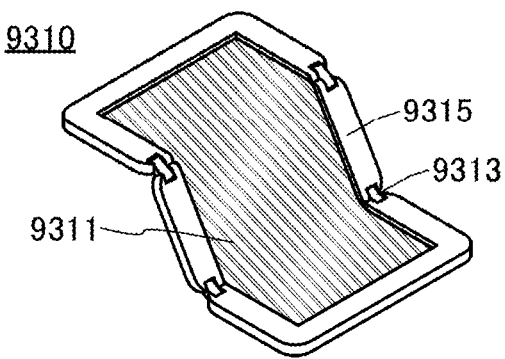
Figure 5C:
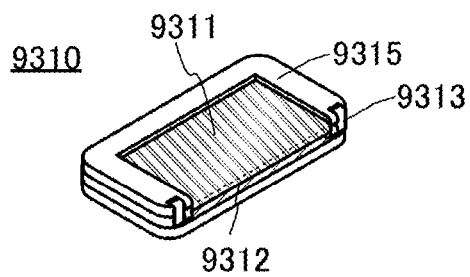

Another electronic device including the light-emitting device is a foldable portable information terminal illustrated in FIGS. 5(A) to (C). FIG. 5(A) illustrates a portable information terminal 9310 which is opened. FIG. 5(B) illustrates the portable information terminal 9310 which is being opened or being folded. FIG. 5(C) illustrates the portable information terminal 9310 which is folded. The portable information terminal 9310 is highly portable when folded, and is highly browsable when opened because of the seamless large display region.

A display portion 9311 is supported by three housings 9315 joined together by hinges 9313. Note that the display portion 9311 may be a touch panel (input/output device) including a touch sensor (input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. In addition, display with high color purity can be performed. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and the starting of application and the like can be smoothly performed.

Figure 6A:
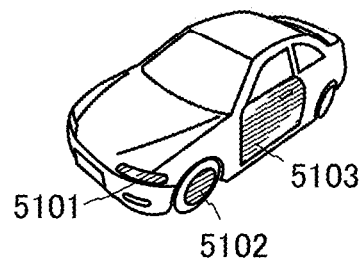
FIGS. 6A and 6B Drawings illustrating an automobile.
Figure 6B:
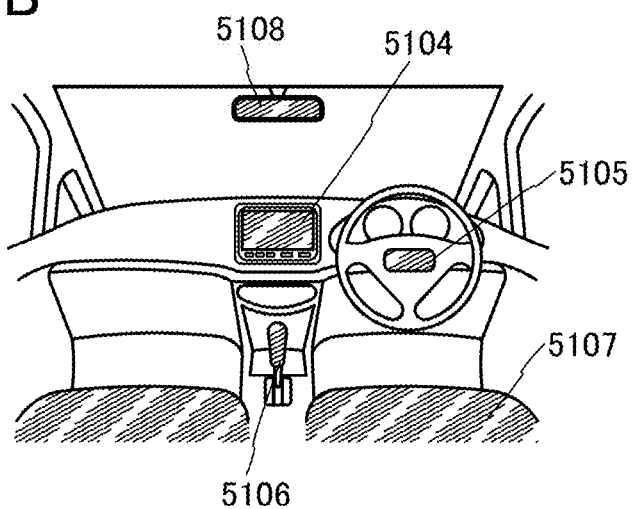

FIGS. 6(A) and (B) illustrate an automobile including the light-emitting device. In other words, the light-emitting device can be integrated into an automobile. Specifically, the light-emitting device can be included in lights 5101 (including lights of the rear part of the car), a wheel cover 5102, a part or the whole of door 5103, or the like on the outer side of the automobile which is illustrated in FIG. 6(A). The light-emitting device can also be included in a display portion 5104, a steering wheel 5105, a shifter 5106, a seat 5107, an inner rearview mirror 5108, or the like on the inner side of the automobile which is illustrated in FIG. 6(B). Apart from that, the light-emitting device may be used for a part of the glass window.

In the above manner, the electronic devices and automobiles in which the light-emitting device or the display device of one embodiment of the present invention is used can be obtained. In that case, display with high color purity can be performed. Note that the light-emitting device or the display device can be used for electronic devices and automobiles in a variety of fields without being limited to those described in this embodiment.

Note that the structures described in this embodiment can be used in an appropriate combination with any of the structures described in the other embodiments.

Embodiment 6

In this embodiment, the structure of a lighting device fabricated using the light-emitting device of one embodiment of the present invention or the light-emitting element which is part of the light-emitting device will be described with reference to FIG. 7.

Figure 7A:
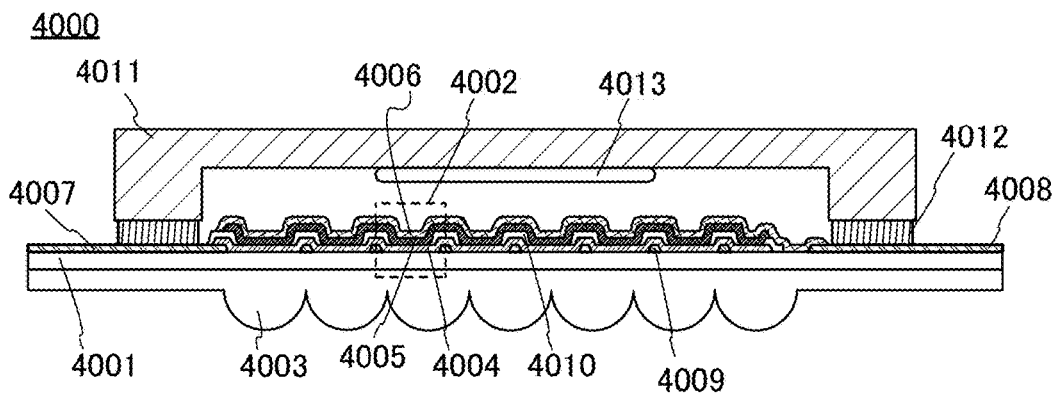
FIGS. 7A-7D Drawings illustrating lighting devices.

FIGS. 7(A), (B), (C), and (D) are examples of cross-sectional views of lighting devices. FIGS. 7(A) and (B) are bottom-emission lighting devices in which light is extracted from the substrate side, and FIGS. 7(C) and (D) are top-emission lighting devices in which light is extracted from the sealing substrate side.

A lighting device 4000 illustrated in FIG. 7(A) includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7(A), whereby the extraction efficiency of light generated in the light-emitting element 4002 can be increased.

Figure 7B:
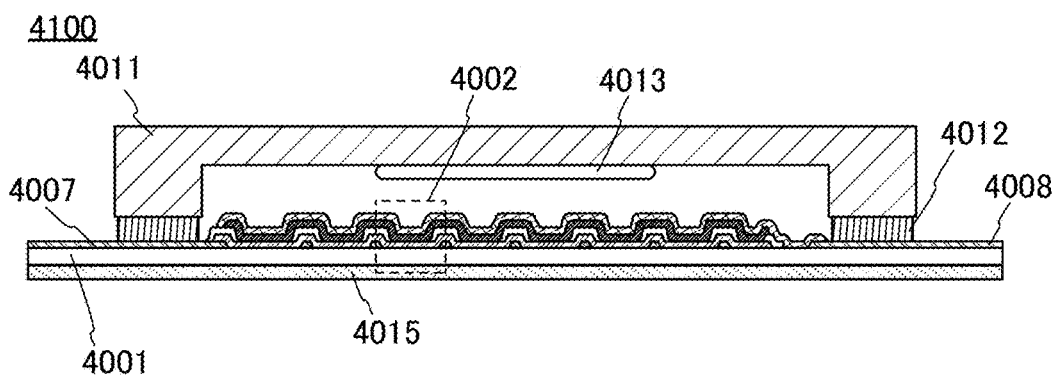

In place of the substrate 4003, a diffusion plate 4015 may be provided on the outside of the substrate 4001 as in a lighting device 4100 illustrated in FIG. 7(B).

Figure 7C:
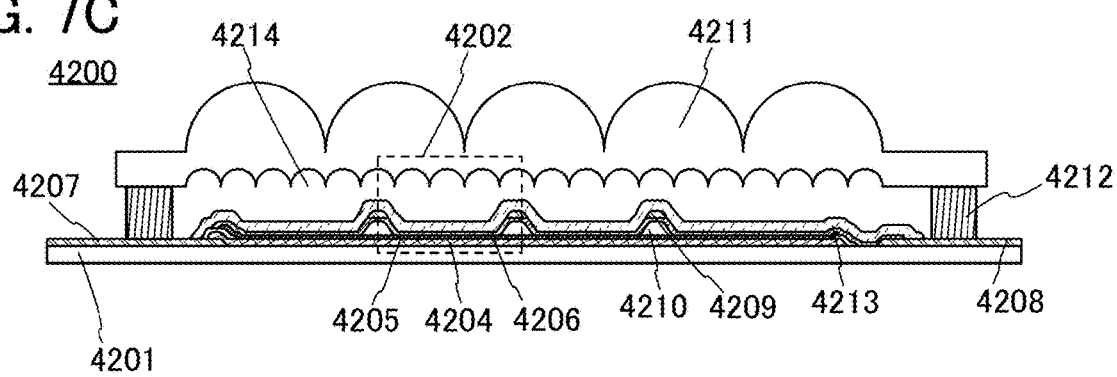

A lighting device 4200 illustrated in FIG. 7(C) includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may also be provided. In addition, an insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7(C), whereby the extraction efficiency of light emitted from the light-emitting element 4202 can be increased.

Figure 7D:
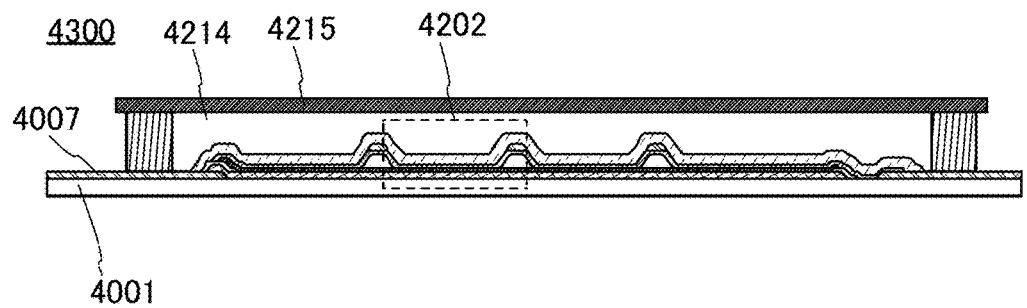

In place of the sealing substrate 4211, a diffusion plate 4215 may be provided over the light-emitting element 4202 as in a lighting device 4300 illustrated in FIG. 7(D).

Note that with the use of the light-emitting device of one embodiment of the present invention or the light-emitting element which is part of the light-emitting device as described in this embodiment, a lighting device having desired chromaticity can be provided.

Note that the structures described in this embodiment can be used in an appropriate combination with any of the structures described in the other embodiments.

Embodiment 7

Figure 8:
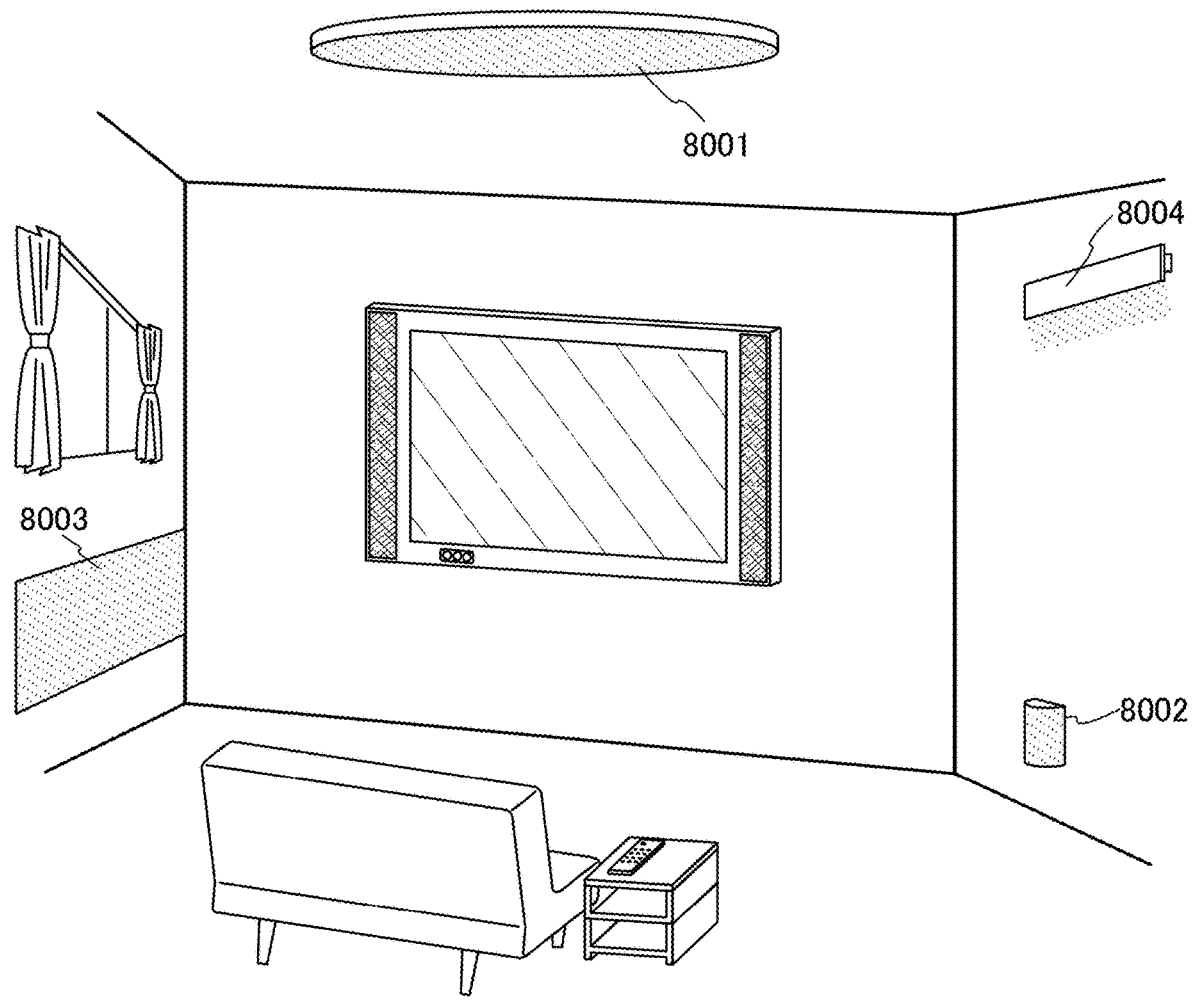
FIG. 8 A drawing illustrating lighting devices.

In this embodiment, application examples of lighting devices fabricated using the light-emitting device of one embodiment of the present invention or the light-emitting element which is part of the light-emitting device will be described with reference to FIG. 8.

A ceiling light 8001 can be used as an indoor lighting device. Examples of the ceiling light 8001 include a direct-mount light and an embedded light. Such lighting devices are fabricated using the light-emitting device and a housing or a cover in combination. Other than that, application to a cord pendant light (light that is suspended from the ceiling by a cord) is also possible.

A foot light 8002 lights the floor so that safety on the floor can be improved. It can be effectively used in a bedroom, on a staircase, or in a passage, for example. In that case, the size or shape of the foot light can be changed in accordance with the area or structure of a room. The foot light can be a stationary lighting device made from the combination of the light-emitting device and a support.

A sheet-like lighting 8003 is a thin sheet-like lighting device. The sheet-like lighting, which is attached to a wall when used, is space-saving and thus can be used for a wide variety of applications. Furthermore, the area of the sheet-like lighting can be easily increased. The sheet-like lighting can also be used on a wall or housing having a curved surface.

In addition, a lighting device 8004 in which the light from a light source is controlled to be only in a desired direction can be used.

In addition to the above examples, when the light-emitting device of one embodiment of the present invention or the light-emitting element which is part of the light-emitting device is used as a part of furniture in a room, a lighting device with functions of furniture can be obtained.

As described above, a variety of lighting devices that include the light-emitting device can be obtained. Note that these lighting devices are also embodiments of the present invention.

The structures described in this embodiment can be used in an appropriate combination with any of the structures described in the other embodiments.

Example 1

Synthesis Example 1

In this example, a synthesis method of 9'-phenyl-9'-[4-(10-phenyl-9-anthryl)phenyl]-2,3'-bi-9H-carbazole (abbreviation: PCCPA-02), which is an organic compound of one embodiment of the present invention represented by the structural formula (200) of Embodiment 1, will be described. The structure of PCCPA-02 is shown below.

[Chemical Formula 15]

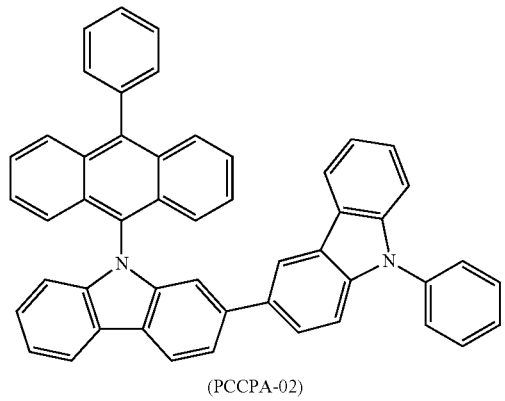

(PCCPA-02) (200)

Into a 200 mL three-neck flask were put 1.2 g (3.0 mmol) of 9-(4-bromophenyl)-10-phenylanthracene, 1.2 g (3.0 mmol) of 9'-phenyl-2,3'-bi-9H-carbazole, and 0.60 g (6.2 mmol) of sodium tert-butoxide, and the air in the flask was replaced with nitrogen. To this mixture was added 30 mL of xylene, and the mixture was degassed by being stirred under reduced pressure. To this mixture were added 0.4 mL of tri(tert-butyl)phosphine, and 48 mg (83 µmol) of bis(dibenzylideneacetone)palladium(0), and the mixture was refluxed at 150° C. for six hours.

After the stirring, water was added to this mixture, and an aqueous layer was subjected to extraction with toluene. The obtained organic layer was washed with a saturated aqueous solution of sodium hydrogen carbonate and saturated saline, and the organic layer was dried with magnesium sulfate. The obtained mixture was gravity-filtered, and the filtrate was concentrated, whereby a solid was obtained. The obtained oily substance was suction-filtered through Celite and alumina, and the filtrate was concentrated, whereby a solid was obtained. The obtained solid was recrystallized with toluene, and 1.1 g of a pale yellow solid, which was the target substance, was obtained in a yield of 49%. The synthesis scheme of the above synthesis method is shown in the following formula (a).

[Chemical Formula 16]

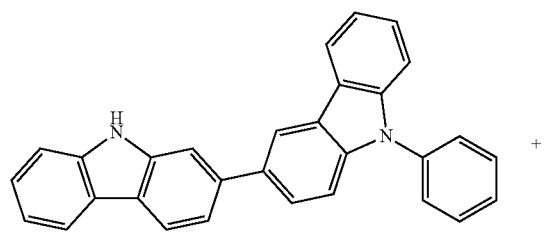

+

-continued

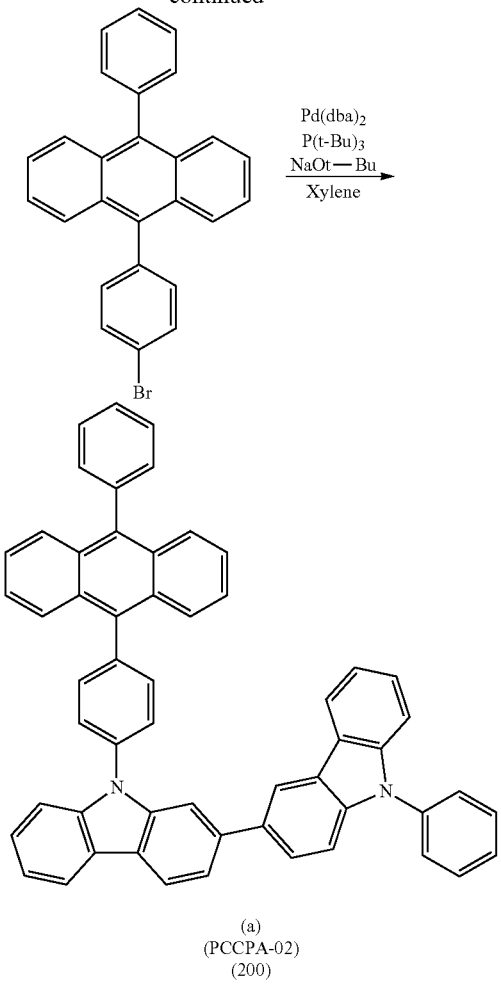

(a)
(PCCPA-02)
(200)

By the train sublimation method, 1.1 g of the obtained pale yellow solid was sublimated and purified. The sublimation purification was performed under the conditions of the pressure being 3.1 Pa and the argon flow rate being 5.0 mL/min, by heating 9'-phenyl-9-[4-(10-phenyl-9-anthryl)phenyl]-2,3'-bi-9H-carbazole at 335° C. After the sublimation purification, 1.0 g of a pale yellow solid was obtained at a collection rate of 92%.

Figure 9A:
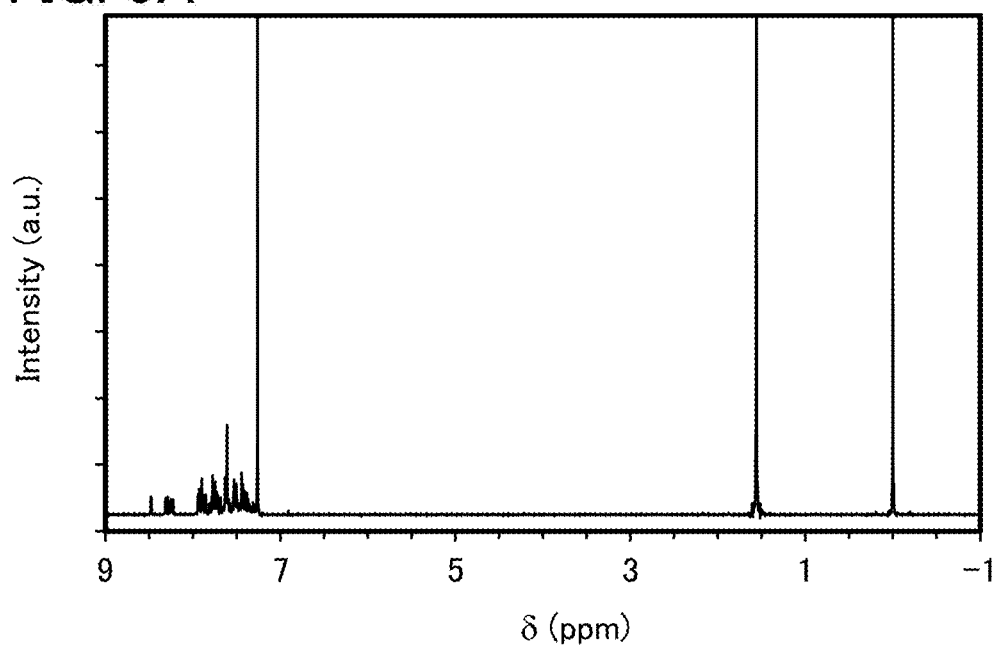
FIGS. 9A and 9B $^1$H-NMR charts of the organic compound represented by the structural formula (200).
Figure 9B:
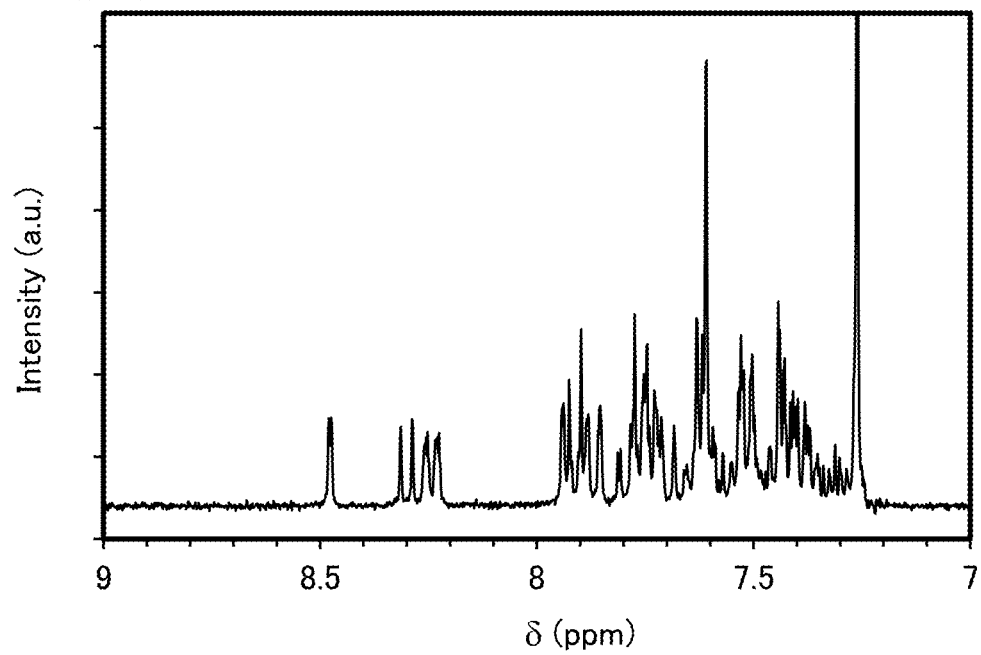

Analysis results the obtained yellow solid by nuclear magnetic resonance ($^1$H-NMR) spectroscopy of are shown below. In addition, $^1$H-NMR charts are shown in FIGS. 9(A) and (B). Note that FIG. 9(B) is a chart showing an enlarged view of the range of 7.0 ppm to 9.0 ppm in FIG. 9(A). These results revealed that PCCPA-02, which is the organic compound of one embodiment of the present invention represented by the above structural formula (200), was obtained in this example.

$^1$H NMR (CDCl$_3$, 300 MHz): δ=7.29-7.81 (m, 27H), 7.85-7.94 (m, 5H), 8.24 (d, J=7.8 Hz, 2H), 8.30 (d, J=7.8 Hz, 1H), 8.48 (d, J=1.2 Hz, 1H).

Next, the ultraviolet-visible absorption spectra (hereinafter, simply referred to as "absorption spectra") and emission spectra of a toluene solution and a solid thin film of PCCPA-02 were measured. The solid thin film was fabricated over a quartz substrate by the vacuum evaporation method. For the measurement of the absorption spectra, UV-visible spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance ($-\log_{10}$ [% T/(100−% R)]) obtained from a transmittance and a reflectance of the substrate and the thin film. Note that % T represents transmittance and % R represents reflectance. For the measurement of the emission spectrum, a fluorescence spectrophotometer (FS920 manufactured by Hamamatsu Photonics K.K.) was used.

Figure 10A:
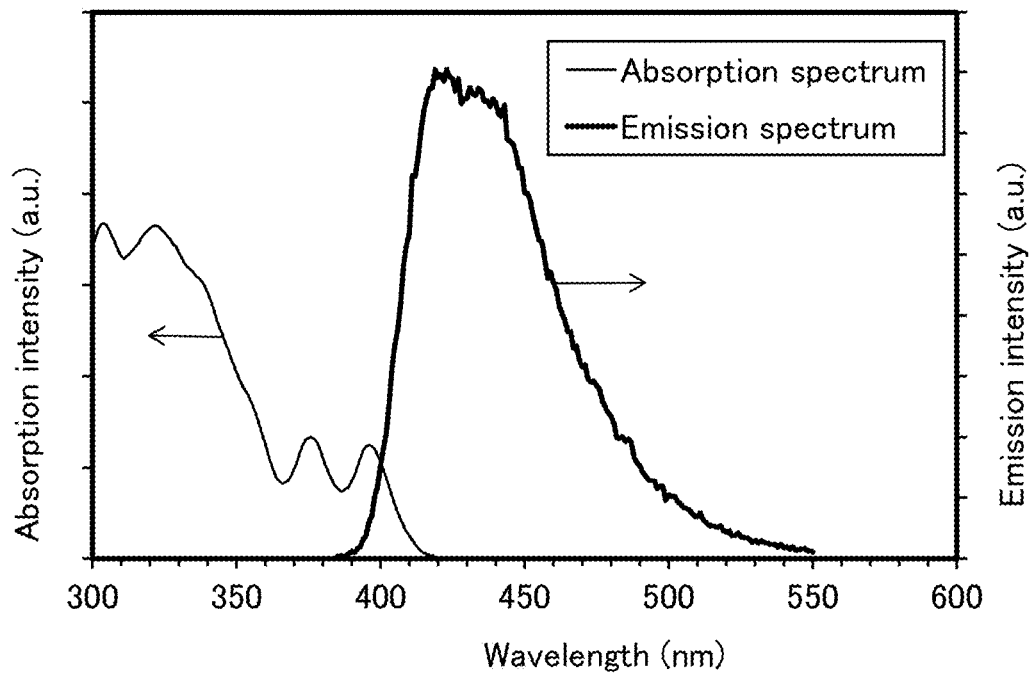
FIGS. 10A and 10B Ultraviolet-visible absorption spectra and emission spectra of the organic compound represented by the structural formula (200).
Figure 10B:
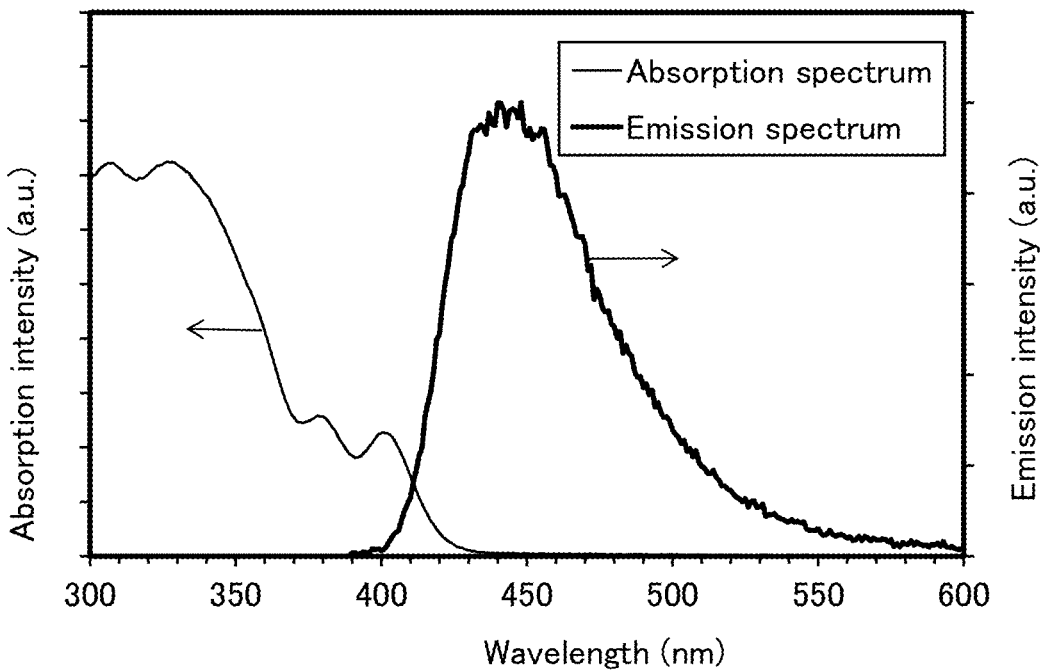

FIG. 10(A) shows the obtained measurement results of the absorption spectrum and the emission spectrum of the toluene solution. The horizontal axis represents wavelength and the vertical axes represent absorption intensity and emission intensity. FIG. 10(B) shows the measurement results of the absorption spectrum and the emission spectrum of the solid thin film. The horizontal axis represents wavelength and the vertical axes represent absorption intensity and emission intensity.

From the results in FIG. 10(A), for the toluene solution of PCCPA-02, absorption peaks were observed at around 396 nm, 376 nm, 322 nm, and 304 nm, and emission wavelength peaks were observed at 422 nm and 433 nm (excitation wavelength: 377 nm). From the results in FIG. 10(B), for the solid thin film of PCCPA-02, absorption peaks were observed at around 399 nm, 377 nm, 353 nm, 325 nm, and 304 nm, and an emission wavelength peak was observed at around 445 nm (excitation wavelength: 380 nm).

Note that PCCPA-02 was confirmed to emit blue light. The organic compound of one embodiment of the present invention, PCCPA-02, can be used as a host for a light-emitting substance or a substance that emits fluorescence in the visible region. Furthermore, the thin film of PCCPA-02 was found to have a good film quality, hardly being aggregated even under air.

The HOMO level and the LUMO level of PCCPA-02 were calculated based on a cyclic voltammetry (CV) measurement. The calculation method is shown below.

An electrochemical analyzer (ALS model 600A or 600C, manufactured by BAS Inc.) was used as a measurement apparatus. To prepare a solution for the CV measurement, dehydrated dimethylformamide (DMF; produced by Sigma-Aldrich Inc., 99.8%, catalog No. 22705-6) was used as a solvent, tetra-n-butylammonium perchlorate (n-Bu$_4$NClO$_4$; produced by Tokyo Chemical Industry Co., Ltd., catalog No. T0836) as a supporting electrolyte was dissolved at a concentration of 100 mmol/L, and the object to be measured was also dissolved at a concentration of 2 mmol/L.

A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag+electrode (RE7 reference electrode for nonaqueous solvent, manufactured by BAS Inc.) was used as a reference electrode. Note that the measurement was performed at room temperature (higher than or equal to 20° C. and lower than or equal to 25° C.).

In addition, the scan speed in the CV measurement was fixed to 0.1 V/sec, and an oxidation potential Ea [V] and a reduction potential Ec [V] with respect to the reference electrode were measured. Ea is an intermediate potential of an oxidation-reduction wave, and Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea, and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the HOMO level was found to be −5.69 eV in the measurement of the oxidation potential Ea[V] of PCCPA-02. In contrast, the LUMO level was found to be −2.72 eV in the measurement of the reduction potential Ec[V]. In addition, when the oxidation-reduction wave was repeatedly measured and the waveform of the first cycle was compared with that in the hundredth cycle, 83% of the peak intensity was maintained in the Ea measurement, and 87% of the peak intensity was maintained in the Ec measurement; thus, resistance to oxidation and reduction of PCCPA-02 was found to be extremely high.

Example 2

Synthesis Example 2

In this example, a synthesis method of 9-phenyl-9'-[4-(10-phenyl-9-anthryl)phenyl]-2,2'-bi-9H-carbazole (abbreviation: PCCPA-03), which is an organic compound of one embodiment of the present invention represented by the structural formula (221) of Embodiment 1, will be described. The structure of PCCPA-03 is shown below.

[Chemical Formula 17]

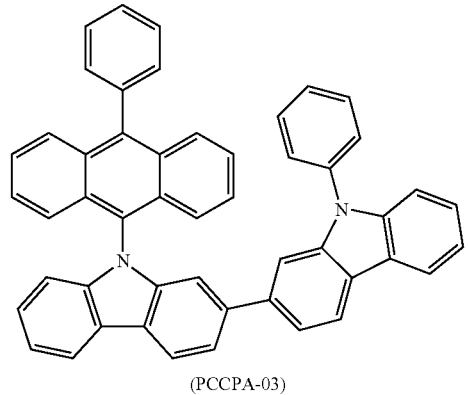

(221)

(PCCPA-03)

Into a 100 mL three-neck flask were put 1.2 g (3.0 mmol) of 9-(4-bromophenyl)-10-phenylanthracene, 1.3 g (3.1 mmol) of 9-phenyl-2,2'-bi-9H-carbazole, and 0.59 g (6.1 mmol) of sodium tert-butoxide, and the air in the flask was replaced with nitrogen. To this mixture was added 30 mL of xylene, and the mixture was degassed by being stirred under reduced pressure. To this mixture were added 0.4 mL of a 10 wt % hexane solution of tri(tert-butyl)phosphine and 85 mg (0.15 mmol) of bis(dibenzylideneacetone)palladium(0), and the mixture was refluxed at 140° C. for six hours.

After the stirring, the obtained mixture was washed with water, a saturated aqueous solution of sodium hydrogen carbonate, and saturated brine, and the organic layer was dried with magnesium sulfate. This mixture was gravity-filtered, and the filtrate was concentrated. The obtained oily substance was purified by silica gel column chromatography (toluene: hexane=1:2), and then was recrystallized with toluene, whereby 1.6 g of a pale yellow solid, which was the target substance, was obtained in a yield of 71%. The synthesis scheme of the above synthesis method is shown in the following formula (b).

[Chemical Formula 18]

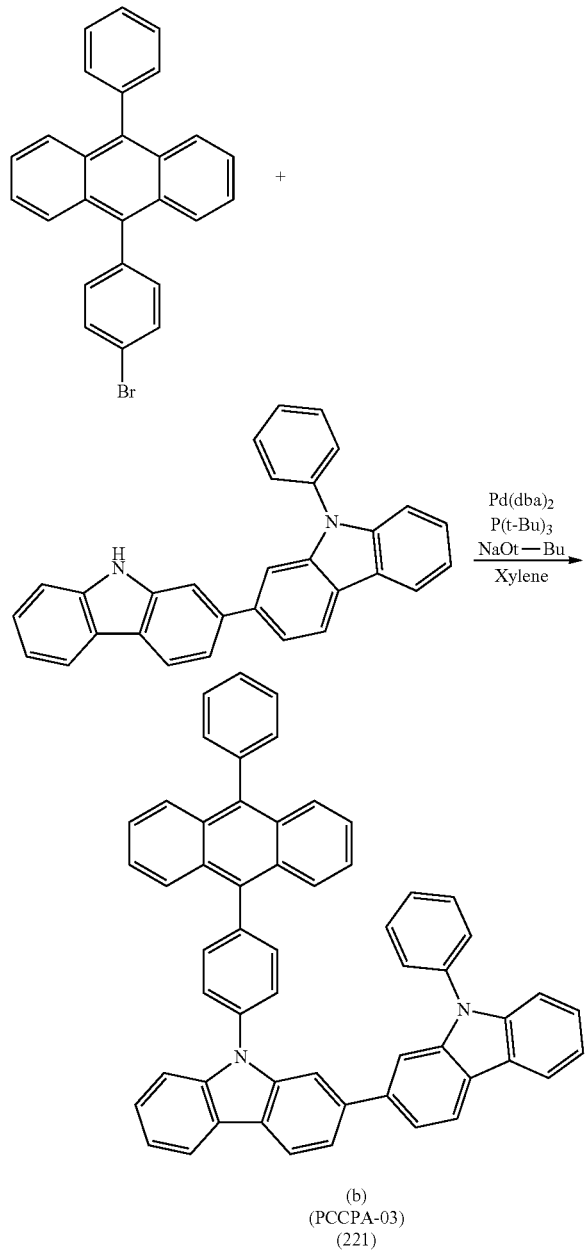

(b)
(PCCPA-03)
(221)

By the train sublimation method, 1.6 g of the obtained pale yellow solid was sublimated and purified. The sublimation purification was performed under the conditions of the pressure being 3.2 Pa and the argon flow rate being 5.0 mL/min, by heating at 320° C. for 18 hours. After the sublimation purification, 1.4 g of a pale yellow solid was obtained at a collection rate of 93%.

Figure 11A:
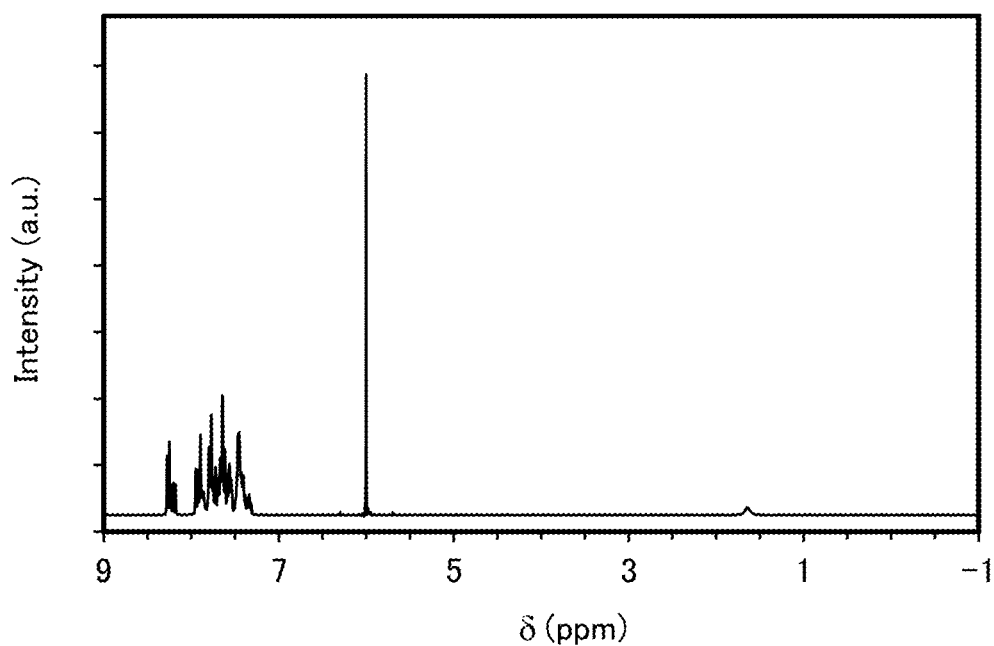
FIGS. 11A and 11B charts of the organic compound represented by the structural formula (221).
Figure 11B:
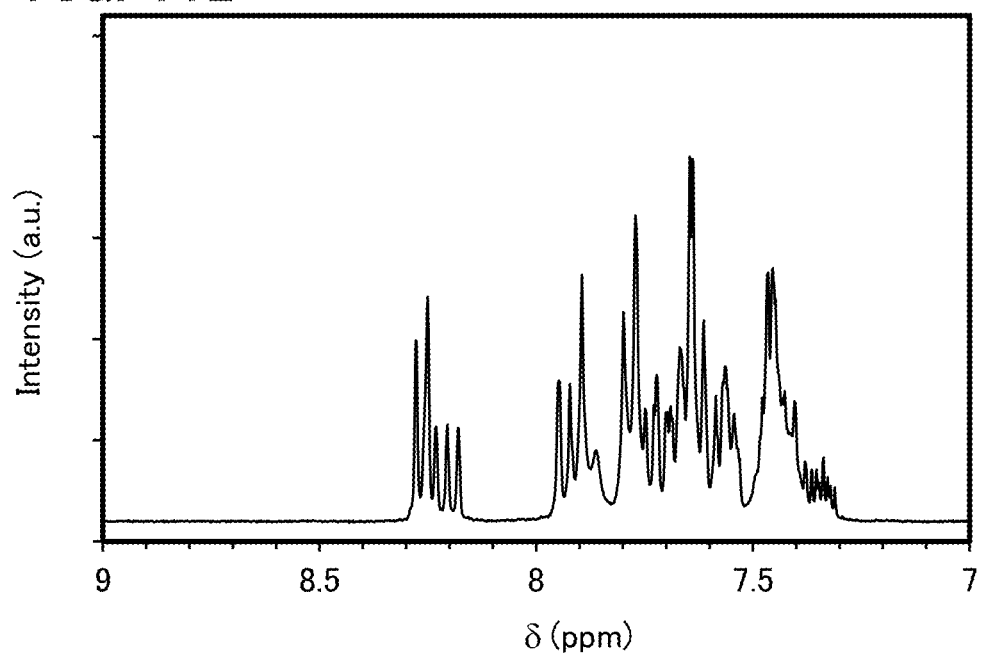

Analysis results of the obtained pale yellow solid by nuclear magnetic resonance ($^1$H-NMR) spectroscopy are shown below. In addition, $^1$H-NMR charts are shown in FIGS. 11(A) and (B). Note that FIG. 11(B) is a chart showing an enlarged view of the range of 7.0 ppm to 8.5 ppm in FIG. 11(A). These results revealed that PCCPA-03, which is the organic compound of one embodiment of the present invention represented by the above structural formula (221), was obtained in this example.

$^1$H NMR (1,1,2,2-tetrachloroethane-d2, 300 MHz): δ=7.31-7.95 (m, 32H), 8.19 (d, J=7.5 Hz, 1H), 8.23-8.28 (m, 3H)

Next, the ultraviolet-visible absorption spectra (hereinafter, simply referred to as "absorption spectra") and emission spectra of a toluene solution and a solid thin film of PCCPA-03 were measured. The solid thin film was fabricated over a quartz substrate by the vacuum evaporation method. For the measurement of the absorption spectra, UV-visible spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance ($-\log_{10}$ [% T/(100–% R)]) obtained from a transmittance and a reflectance of the substrate and the thin film. Note that % T represents transmittance and % R represents reflectance. For the measurement of the emission spectrum, a fluorescence spectrophotometer (FS920 manufactured by Hamamatsu Photonics K.K.) was used.

Figure 12A:
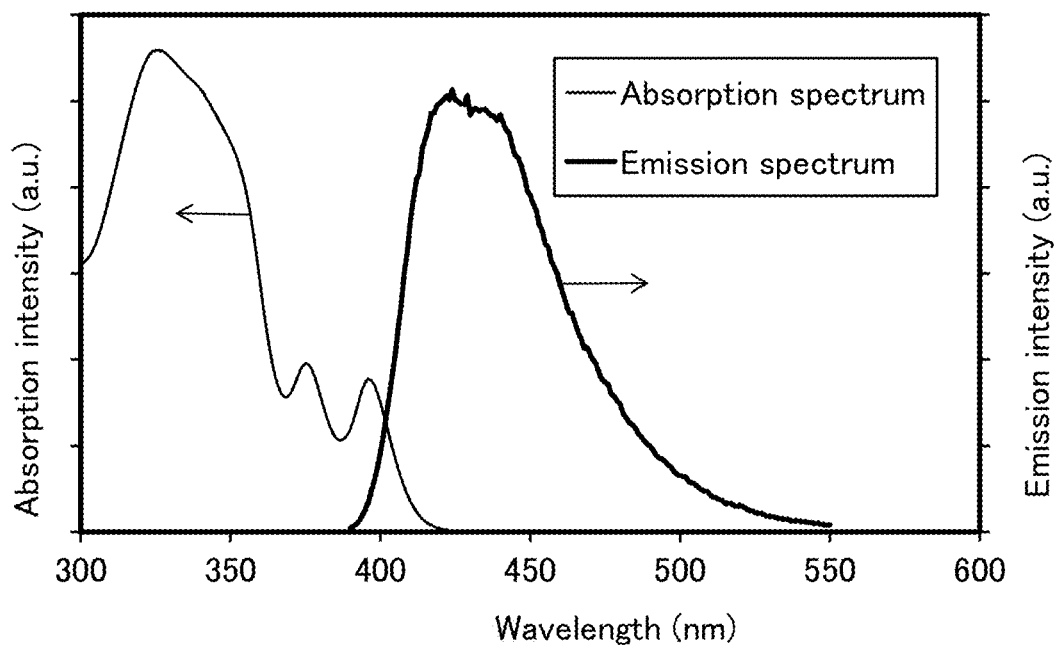
FIGS. 12A and 12B Ultraviolet-visible absorption spectra and emission spectra of the organic compound represented by the structural formula (221).
Figure 12B:
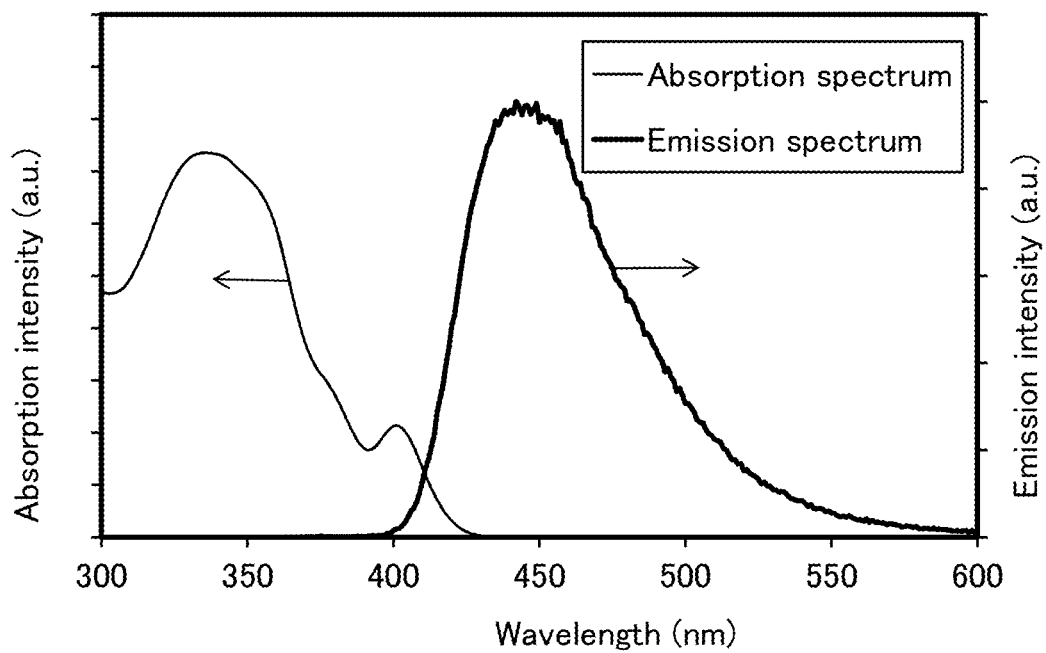

FIG. 12(A) shows the obtained measurement results of the absorption spectrum and the emission spectrum of the toluene solution. The horizontal axis represents wavelength and the vertical axes represent absorption intensity and emission intensity. FIG. 12(B) shows the measurement results of the absorption spectrum and the emission spectrum of the solid thin film. The horizontal axis represents wavelength and the vertical axes represent absorption intensity and emission intensity.

From the results in FIG. 12(A), for the toluene solution of PCCPA-03, absorption peaks were observed at around 396 nm, 375 nm, and 326 nm, and an emission wavelength peak was observed at 423 nm (excitation wavelength: 376 nm). From the results in FIG. 12(B), for the solid thin film of PCCPA-03, absorption peaks were observed at around 401 nm, 380 nm, 356 nm, and 335 nm, and an emission wavelength peak was observed at around 446 nm (excitation wavelength: 360 nm).

Note that PCCPA-03 was confirmed to emit blue light. The compound of one embodiment of the present invention can be used as a host for a light-emitting substance or a substance that emits fluorescence in the visible region. Furthermore, the thin film of PCCPA-03 was found to have a good film quality, hardly being aggregated even under air.

Example 3

Figure 13:
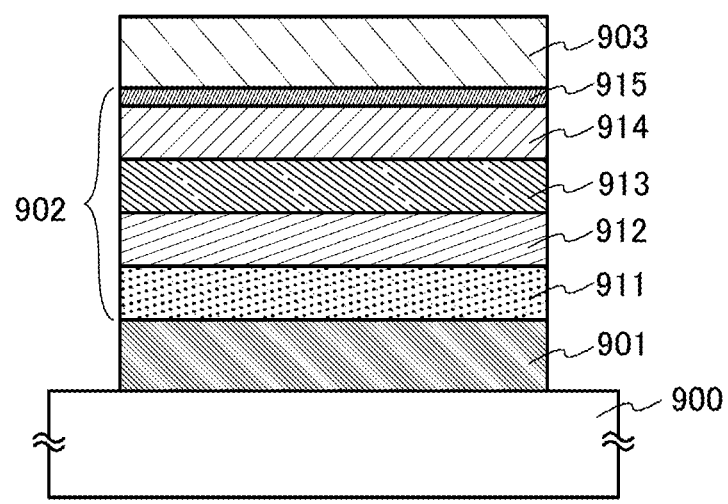
FIG. 13 A drawing illustrating the structure of a light-emitting element.
Figure 14:
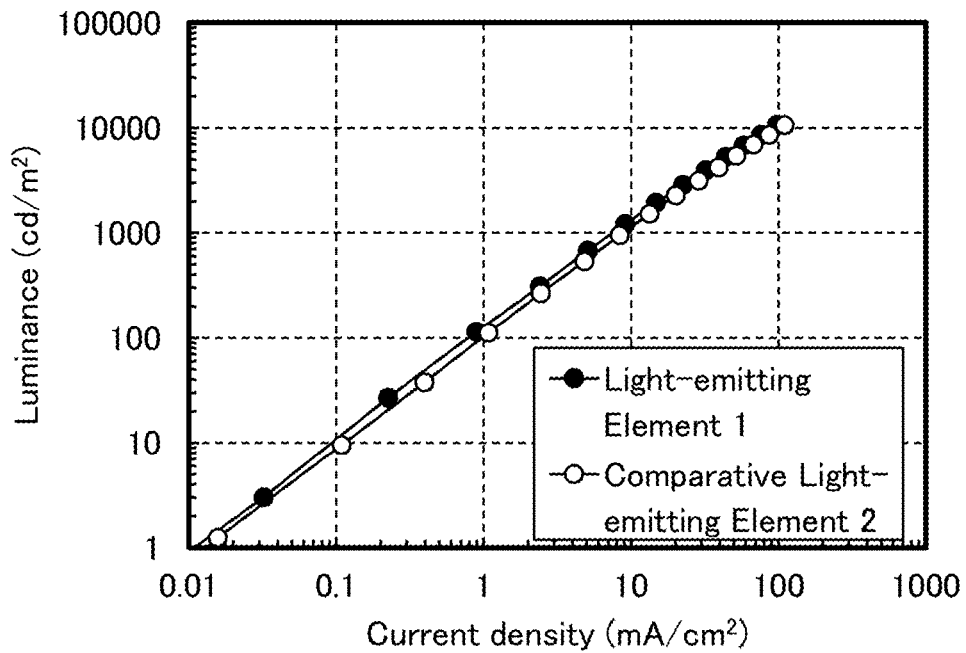
FIG. 14 A graph showing the current density-luminance characteristics of Light-emitting Element 1 and Comparative Light-emitting Element 2.
Figure 15:
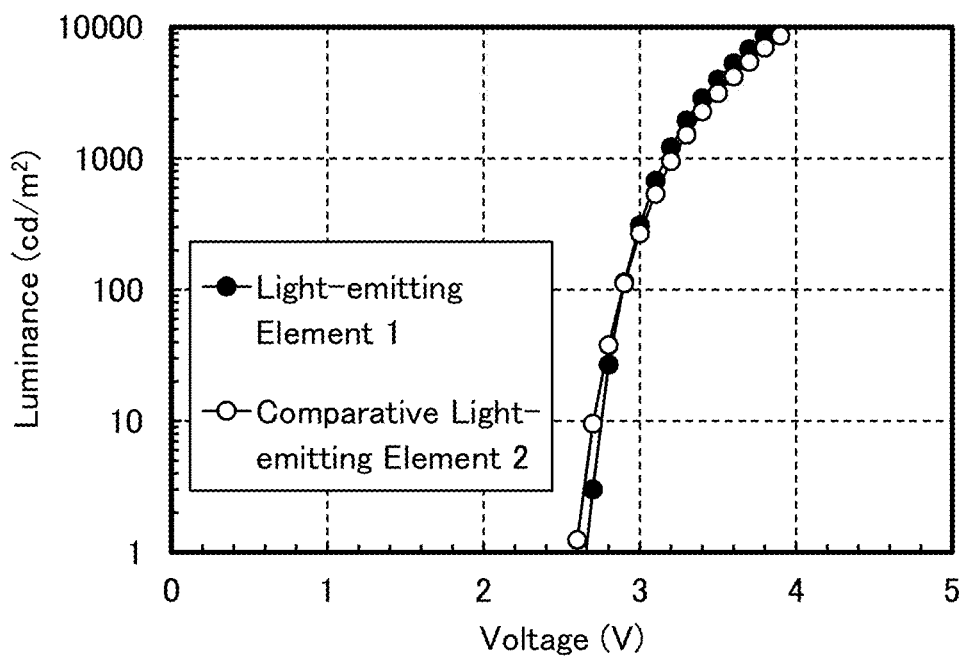
FIG. 15 A graph showing the voltage-luminance characteristics of Light-emitting Element 1 and Comparative Light-emitting Element 2.
Figure 16:
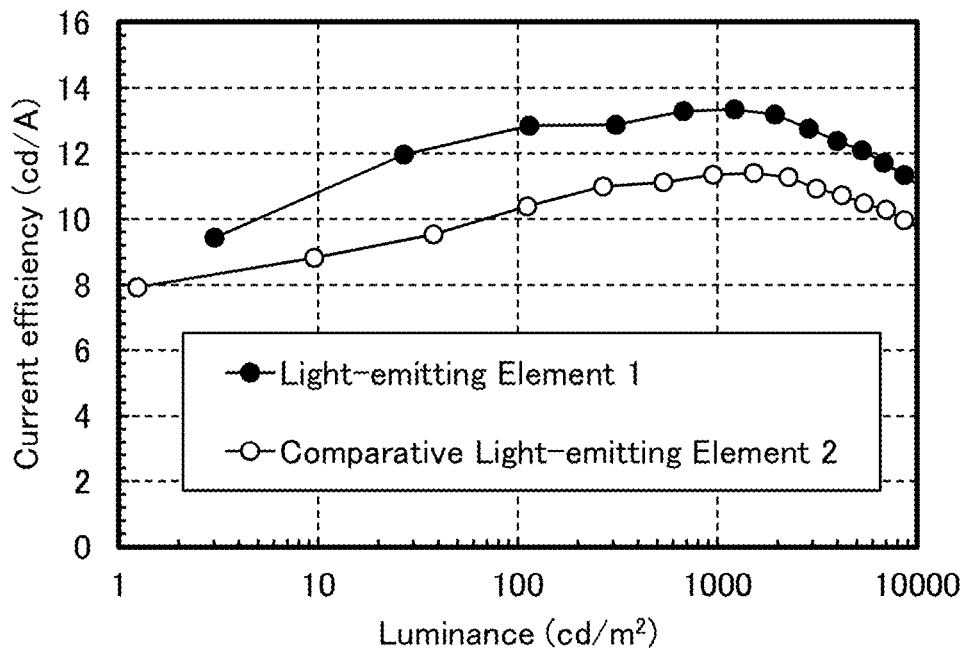
FIG. 16 A graph showing the luminance-current efficiency characteristics of Light-emitting Element 1 and Comparative Light-emitting Element 2.
Figure 17:
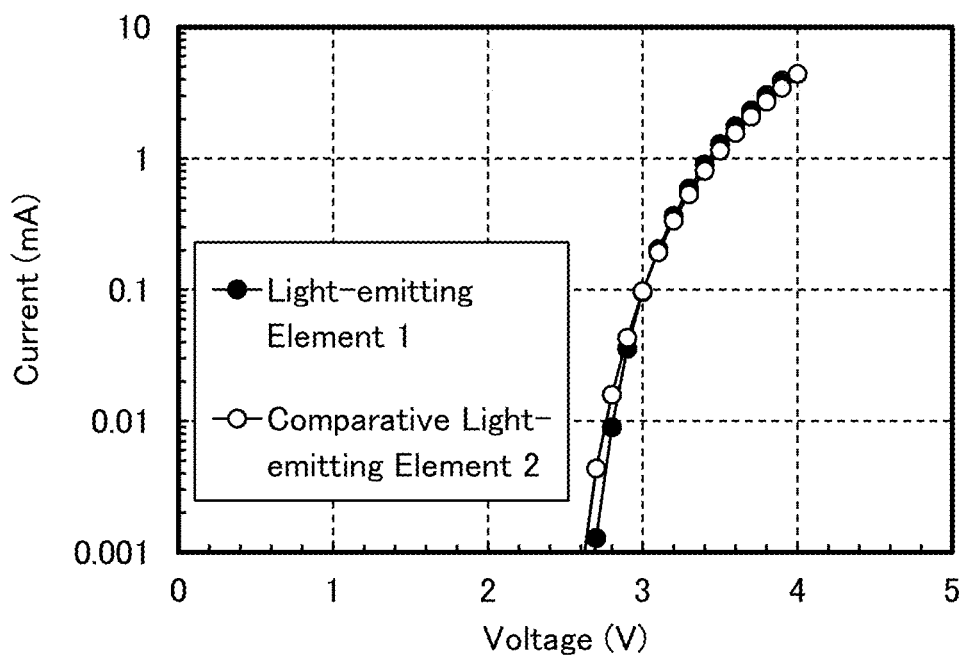
FIG. 17 A graph showing the voltage-current characteristics of Light-emitting Element 1 and Comparative Light-emitting Element 2.

In this example, the element structures, fabrication methods, and characteristics of a light-emitting element 1, which is the light-emitting element of one embodiment of the present invention, and a comparative light-emitting element 2 will be described. The light-emitting element 1 includes PCCPA-02 (structural formula (200)), which is described in Example 1, used for the light-emitting layer, and the comparative light-emitting element 2 includes PCCPA (structural formula (300)), which is a comparative organic compound, used for the light-emitting layer. Note that FIG. 13 illustrates the element structure of the light-emitting elements used in this example, and Table 1 shows specific structures. The chemical formulae of materials used in this example are shown below.

TABLE 1

| | First electrode | Hole-injection layer | Hole-transport layer | Light-emitting layer | Electron-transport layer | Electron-injection layer | Second electrode |
|---|---|---|---|---|---|---|---|
| Light-emitting element 1 | ITSO (70 nm) | PCPPn:MoOx (4:2, 10 nm) | PCPPn (30 nm) | * | PCCPA-02 (10 nm) | Bphen (15 nm) | LiF (1 nm) | Al (200 nm) |
| Comparative light-emitting element 2 | ITSO (70 nm) | PCPPn:MoOx (4:2, 10 nm) | PCPPn (30 nm) | ** | PCCPA (10 nm) | Bphen (15 nm) | LiF (1 nm) | Al (200 nm) |

* PCCPA-02: 1,6mMemFLPAPm (1:0.03, 25 nm)
** PCCPA: 1,6mMemFLPAPm (1:0.03, 25 nm)

[Chemical Formulae 19]

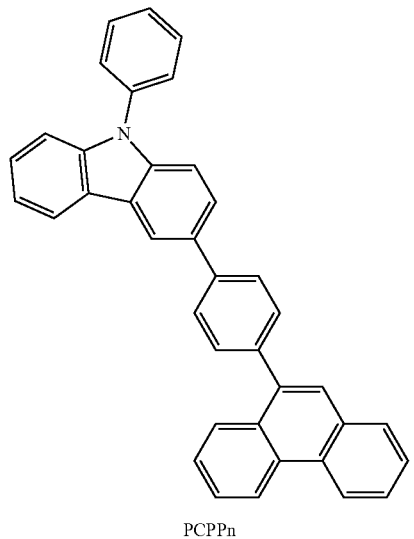

PCPPn

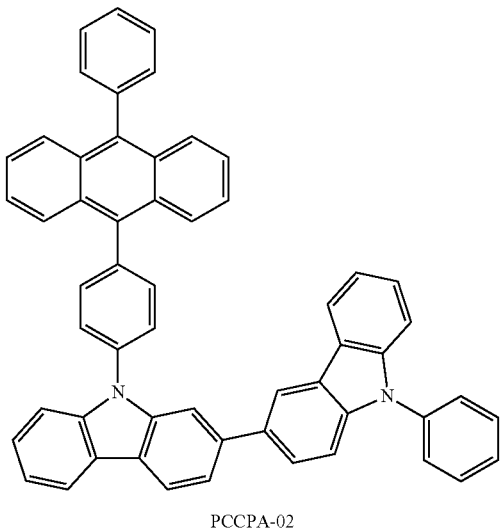

PCCPA-02

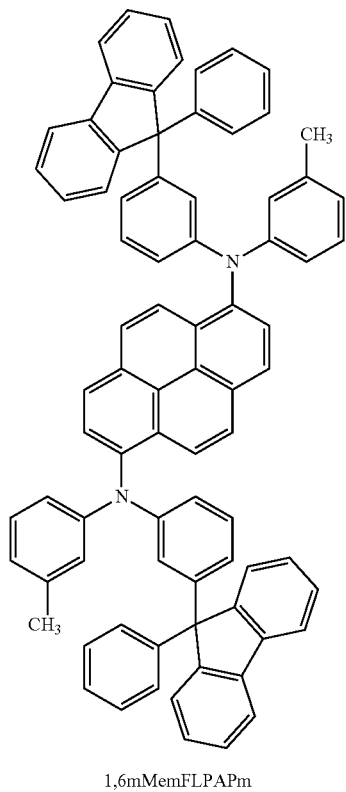

1,6mMemFLPAPm

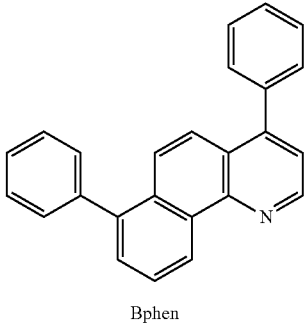

Bphen (200)

-continued

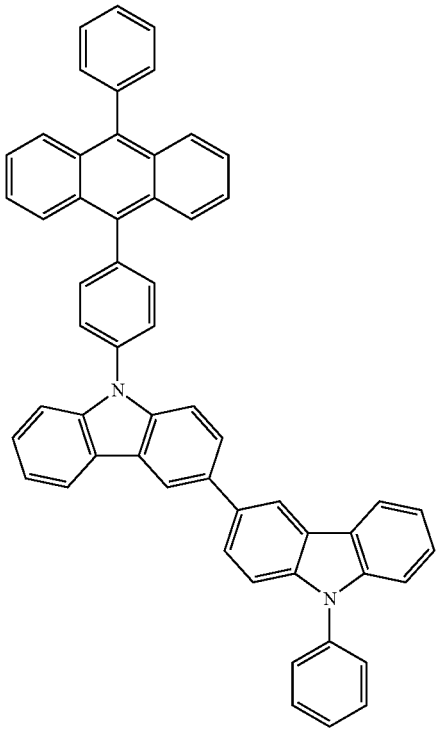

(300)

PCCPA

<<Fabrication of Light-Emitting Elements>>

In each of the light-emitting elements described in this example, as illustrated in FIG. 13, a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm² (2 mm×2 mm). A glass substrate was used as the substrate 900. The first electrode 901 was formed to a thickness of 70 nm using indium tin oxide containing silicon oxide (ITSO) by the sputtering method.

As a pretreatment, the surface of the substrate was washed with water, baking was performed at 200° C. for one hour, and then UV ozone treatment was performed for 370 seconds. After that, the substrate was transferred into a vacuum evaporation apparatus where the pressure had been reduced to approximately $10^{-4}$ Pa, and was subjected to vacuum baking at 170° C. for 60 minutes in a heating chamber of the vacuum evaporation apparatus, and then the substrate was cooled down for approximately 30 minutes.

Next, the hole-injection layer 911 was formed over the first electrode 901. After the pressure in the vacuum evaporation apparatus was reduced to $10^{-4}$ Pa, the hole-injection layer 911 was formed by co-evaporating 3-[4-(9-phenanthryl)-phenyl]-9-phenyl-9H-carbazole (abbreviation: PCPPn) and molybdenum oxide, with a mass ratio of PCPPn: molybdenum oxide being 4:2, to a thickness of 10 nm.

Then, the hole-transport layer 912 was formed over the hole-injection layer 911. The hole-transport layer 912 was formed to a thickness of 30 nm by the evaporation of PCPPn.

Next, the light-emitting layer 913 was formed over the hole-transport layer 912.

In the light-emitting element 1, the light-emitting layer 913 was formed by co-evaporation using PCCPA-02 as a host material, and N,N'-bis(3-methylphenyl)-N,N'-bis[3-(9-phenyl-9H-fluoren-9-yl)phenyl]pyrene-1,6-diamine (abbreviation: 1,6mMemFLPAPrn) as a guest material, in a way that the weight ratio of PCCPA-02: 1,6mMemFLPAPrn would be 1:0.03. The thickness was set to 25 nm.

In the comparative light-emitting element 2, the light-emitting layer 913 was formed by co-evaporation using PCCPA as a host material, and 1,6 mMemFLPAPrn as a guest material in a way that the weight ratio of PCCPA:1,6 mMemFLPAPrn would be 1:0.03. The thickness was set to 25 nm.

Next, the electron-transport layer 914 was formed over the light-emitting layer 913. In the light-emitting element 1, the electron-transport layer 914 was formed sequentially depositing PCCPA-02 and bathophenanthroline (abbreviation: Bphen) by evaporation to thicknesses of 10 nm and 15 nm, respectively. In the comparative light-emitting element 2, the electron-transport layer 914 was formed by sequentially depositing PCCPA and bathophenanthroline (abbreviation: Bphen) by evaporation to thicknesses of 10 nm and 15 nm, respectively.

Then, the electron-injection layer 915 was formed over the electron-transport layer 914. The electron-injection layer 915 was formed by depositing lithium fluoride (LiF) by evaporation to a thickness of 1 nm.

Then, the second electrode 903 was formed over the electron-injection layer 915. The second electrode 903 was formed to a thickness of 200 nm by the evaporation of aluminum. In this example, the second electrode 903 functions as a cathode.

Through the above steps, the light-emitting elements each including an EL layer between a pair of electrodes were formed over the substrate 900. The hole-injection layer 911, the hole-transport layer 912, the light-emitting layer 913, the electron-transport layer 914, and the electron-injection layer 915 described in the above steps are functional layers forming the EL layer of one embodiment of the present invention. Furthermore, in all the evaporation steps in the above fabrication method, evaporation was performed by a resistance-heating method.

Each of the light-emitting elements fabricated as described above was sealed using another substrate (not illustrated). Note that the sealing using another substrate (not illustrated) was performed in the following manner: another substrate (not illustrated) was fixed to the substrate 900 with the use of a sealant; a sealant was applied to the periphery of the light-emitting element formed over the substrate 900; and the sealant was irradiated with 365-nm ultraviolet light at 6 J/cm² and heated at 80° C. for one hour when sealing.

<<Operation Characteristics of Light-Emitting Elements>>

Operation characteristics of the fabricated light-emitting elements were measured. Note that the measurement was performed at room temperature. The results are shown in FIGS. 14 to 17.

The initial values of the main characteristics of the light-emitting elements at around 1000 cd/m² are shown below in Table 2.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.2 | 0.37 | 9.1 | (0.14, 0.16) | 1200 | 13 | 13 | 12 |
| Comparative light-emitting element 2 | 3.2 | 0.34 | 8.4 | (0.15, 0.18) | 950 | 11 | 11 | 8.7 |

The above results show that the light-emitting element 1 fabricated in this example has high current efficiency and high external quantum efficiency. From these results, it is found that changing the bonding position between the first carbazole skeleton bonded to an anthracene skeleton and the second carbazole skeleton bonded to the first carbazole skeleton enables smooth energy transfer to the light-emitting material, whereby favorable element characteristics can be obtained.

Figure 18:
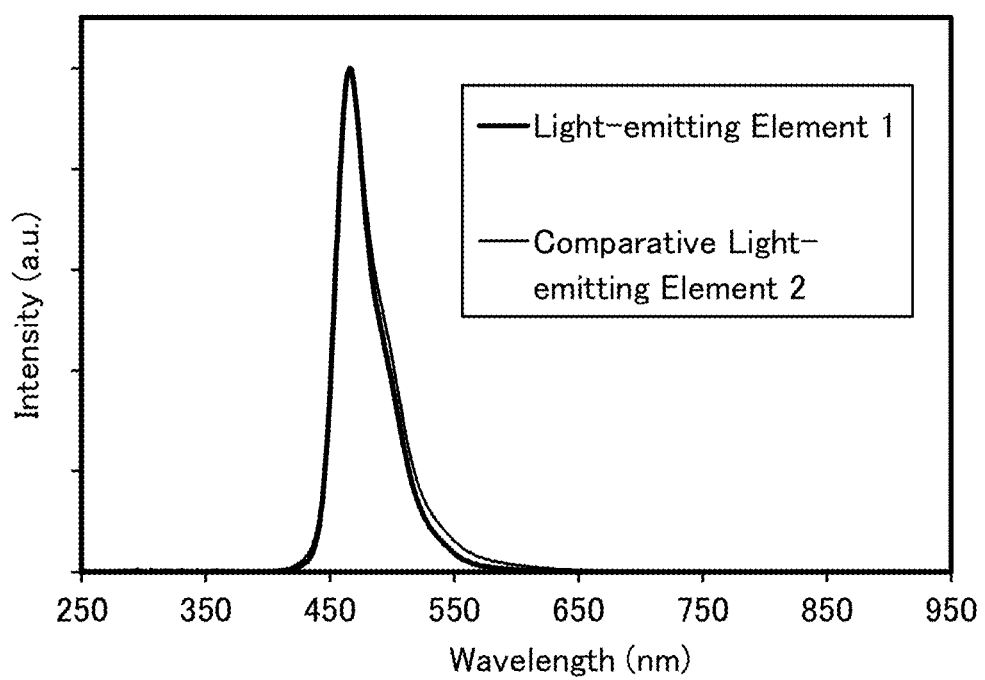
FIG. 18 A graph showing the emission spectra of Light-emitting Element 1 and Comparative Light-emitting Element 2.

FIG. 18 shows emission spectra in the case where current at a current density of 12.5 mA/cm$^2$ was supplied to the light-emitting element 1 and the comparative light-emitting element 2. As shown in FIG. 18, the emission spectra of the light-emitting element 1 and the comparative light-emitting element 2 each have a peak at around 466 nm, which indicates that the peak is derived from light emission of 1,6 mMemFLPAPrn contained in the light-emitting layer 913.

Figure 19:
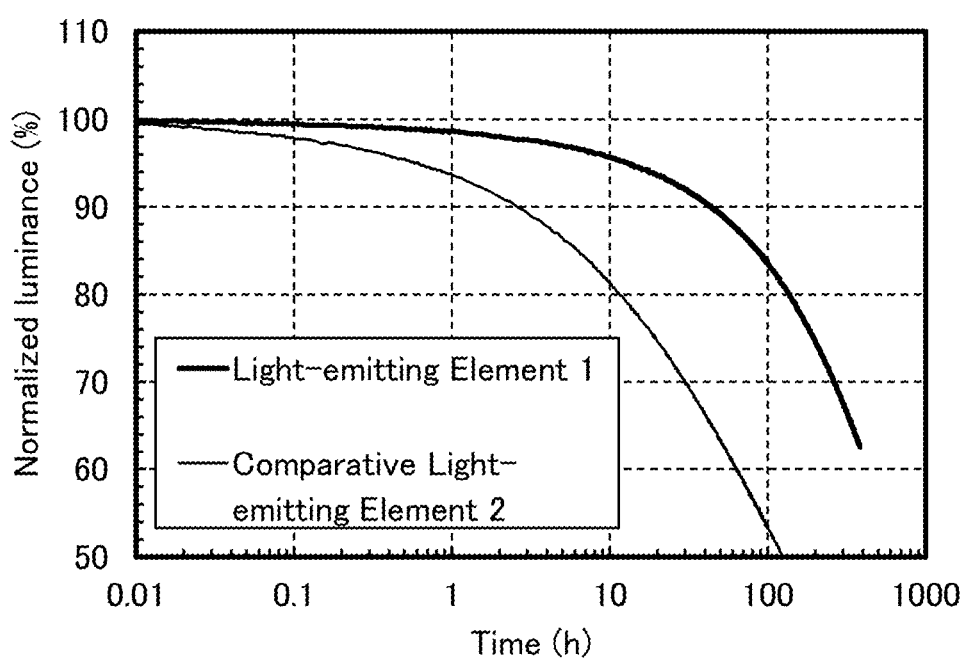
FIG. 19 A graph showing the reliability of Light-emitting Element 1 and Comparative Light-emitting Element 2.

Next, reliability tests were performed on the light-emitting element 1 and the comparative light-emitting element 2. Results of the reliability test are shown in FIG. 19. In FIG. 19, the vertical axis represents normalized luminance (%) with an initial luminance of 100%, and the horizontal axis represents driving time (h) of the element. Note that for the reliability tests, driving tests at a constant current of 2 mA were performed.

These results reveal that the light-emitting element of one embodiment of the present invention (the light-emitting element 1) exhibits characteristics superior to those of the comparative light-emitting element 2 as the comparative element in current efficiency and external quantum efficiency, and that the light-emitting element of one embodiment of the present invention (the light-emitting element 1) is superior in reliability as well.

Example 4

Synthesis Example 3

In this example, a synthesis method of 7-[4-(10-phenyl-9-anthryl)phenyl]-9-(9-phenyl-9H-carbazol-3-yl)-7H-benzo[c]carbazole (abbreviation: PCcBCzPA), which is an organic compound of one embodiment of the present invention represented by the structural formula (252) of Embodiment 1, will be described. The structure of PCcBCzPA is shown below.

[Chemical Formula 20]

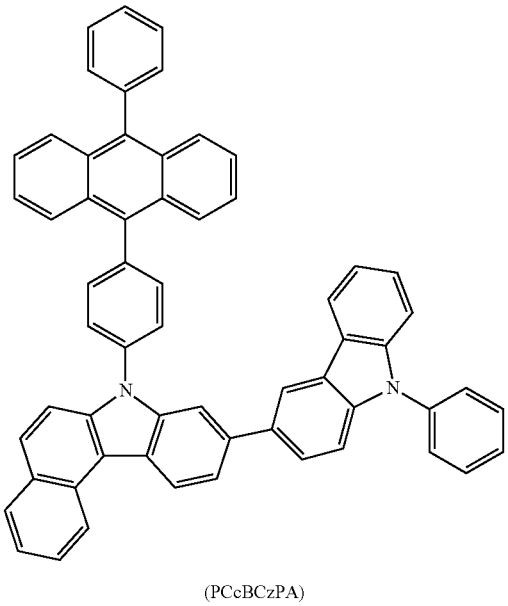

(252)

(PCcBCzPA)

Into a 100 mL three-neck flask were put 1.8 g (4.4 mmol) of 9-(4-bromophenyl)-10-phenylanthracene, 2.0 g (4.4 mmol) of 9-(9-phenyl-9H-carbazol-3-yl)-7H-benzo[c]carbazole, and 0.85 g (8.8 mmol) of sodium tert-butoxide, and the air in the flask was replaced with nitrogen. To this mixture were added 22 mL of xylene and 0.9 mL of a 10 wt % hexane solution of tri(tert-butyl)phosphine, and the mixture was degassed by being stirred under reduced pressure. To this mixture was added 0.13 g (0.22 mmol) of bis(dibenzylideneacetone)palladium(0), and the mixture was refluxed at 160° C. for six hours under a nitrogen stream.

After the stirring, water was added to this mixture, and the solid was filtered. A toluene solution of the obtained solid was suction-filtered through Celite, alumina, and florisil, and the filtrate was concentrated, whereby a solid was obtained. The obtained solid was purified by silica gel column chromatography (toluene), and then was recrystallized with toluene, whereby 2.2 g of a pale yellow solid, which was the target substance, was obtained in a yield of 63%. The synthesis scheme of the above synthesis method is shown in the following formula (c).

[Chemical Formula 21]

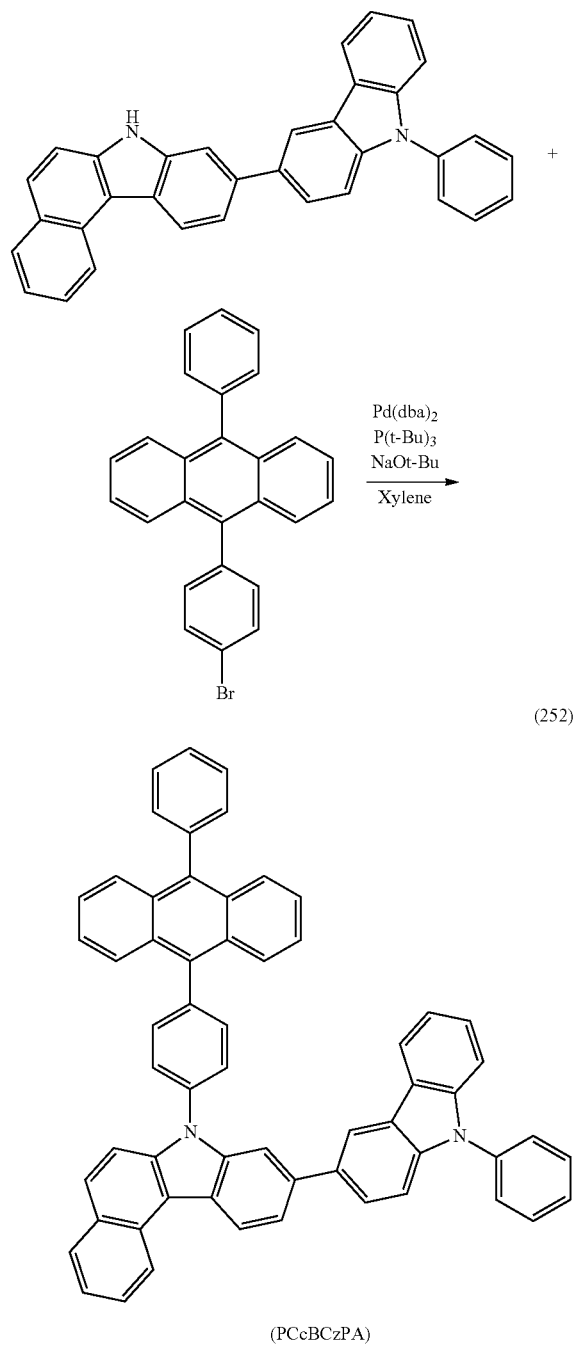

(PCcBCzPA)

By the train sublimation method, 0.95 g of the obtained pale yellow solid was sublimated and purified. The sublimation purification was performed under the condition of the pressure being 1.3×10⁻² Pa, by heating the pale yellow solid at 300° C. After the sublimation purification, 0.74 g of a pale yellow solid was obtained at a collection rate of 78%.

Figure 20A:
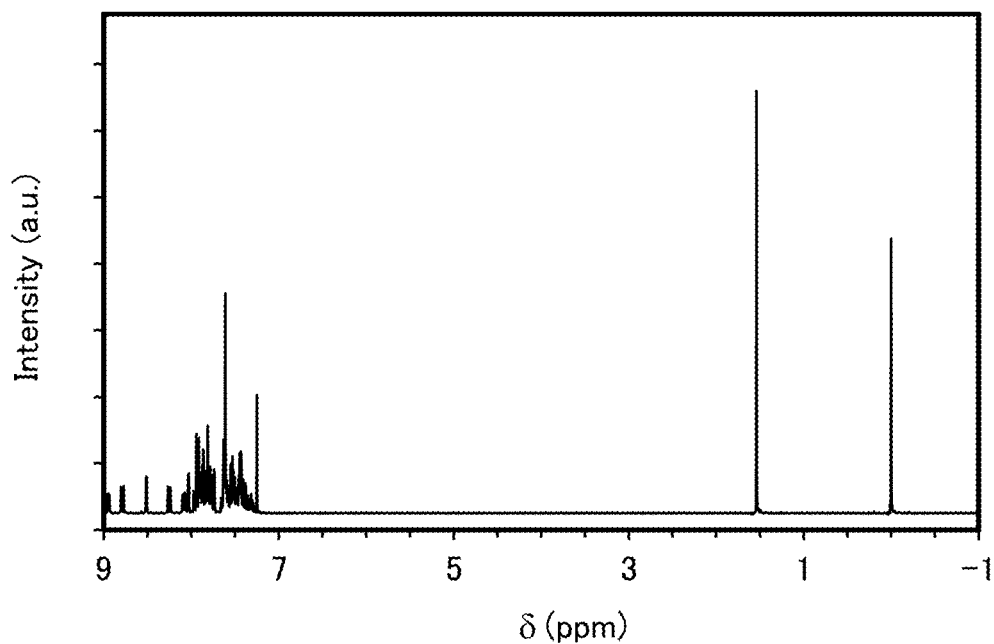
FIGS. 20A and 20B $^1$H-NMR charts of the organic compound represented by the structural formula (252).
Figure 20B:
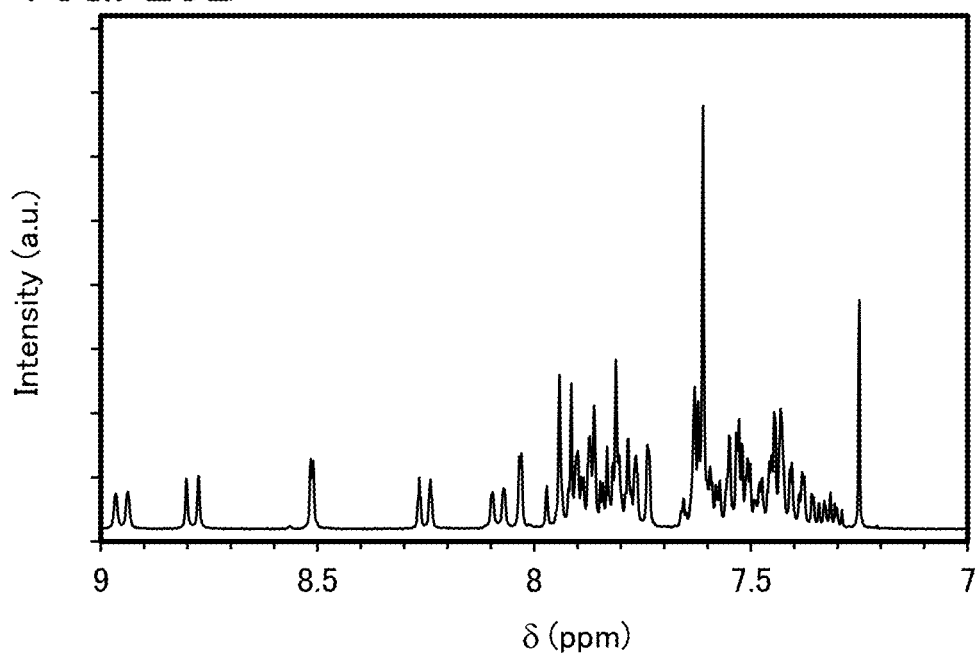

Analysis results of the obtained pale yellow solid by nuclear magnetic resonance (¹H-NMR) spectroscopy are shown below. In addition, ¹H-NMR charts are shown in FIGS. 20(A) and (B). Note that FIG. 20(B) is a chart showing an enlarged view of the range of 7.0 ppm to 9.0 ppm in FIG. 20(A). These results revealed that PCcBCzPA, which is the organic compound of one embodiment of the present invention represented by the above structural formula (252), was obtained in this example.

¹H NMR (CDCl₃, 300 MHz): δ=7.29-7.97 (m, 32H), 8.03(d, J=1.5 Hz, 1H), 8.08 (d, J=7.8 Hz, 1H), 8.25 (d, J=7.8 Hz, 1H), 8.51 (d, J=1.5 Hz, 1H), 8.79 (d, J=8.4 Hz, 1H), 8.95 (d, J=8.1 Hz, 1H)

Next, the ultraviolet-visible absorption spectra (hereinafter, simply referred to as "absorption spectra") and emission spectra of a toluene solution and a solid thin film of PCcBCzPA were measured. The solid thin film was fabricated over a quartz substrate by the vacuum evaporation method. For the measurement of the absorption spectra, UV-visible spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance (−log₁₀ [% T/(100−% R)]) obtained from a transmittance and a reflectance of the substrate and the thin film. Note that % T represents transmittance and % R represents reflectance. For the measurement of the emission spectrum, a fluorescence spectrophotometer (FS920 manufactured by Hamamatsu Photonics K.K.) was used.

Figure 21A:
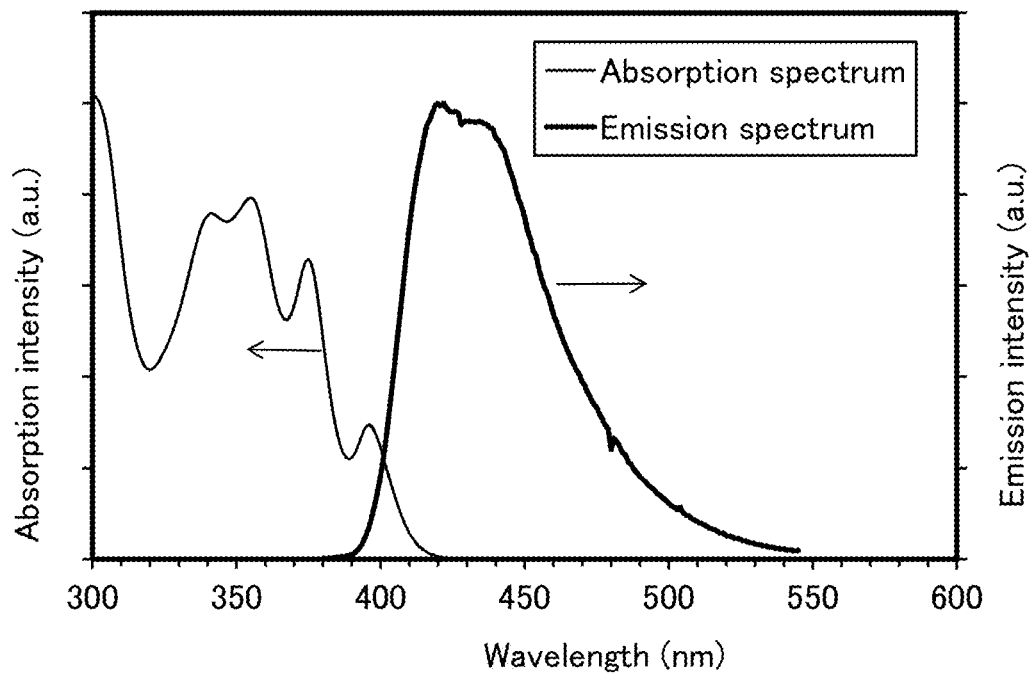
FIGS. 21A and 21B Ultraviolet-visible absorption spectra and emission spectra of the organic compound represented by the structural formula (252).
Figure 21B:
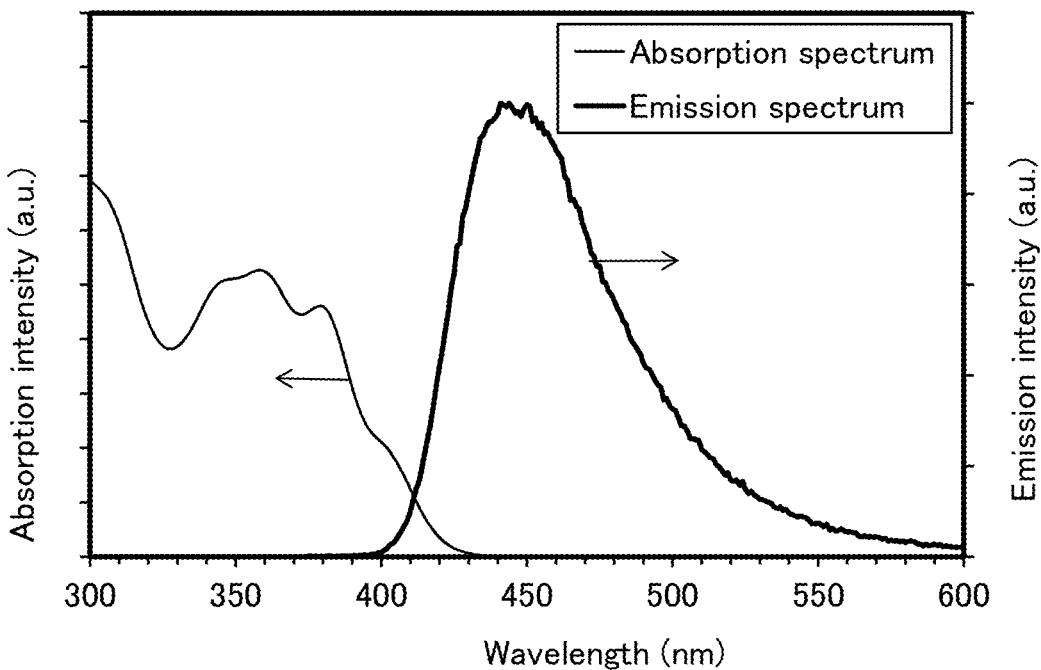

FIG. 21(A) shows the obtained measurement results of the absorption spectrum and the emission spectrum of the toluene solution. The horizontal axis represents wavelength and the vertical axes represent absorption intensity and emission intensity. FIG. 21(B) shows the measurement results of the absorption spectrum and the emission spectrum of the solid thin film. The horizontal axis represents wavelength and the vertical axes represent absorption intensity and emission intensity.

From the results in FIG. 21(A), for the toluene solution of PCcBCzPA, absorption peaks were observed at around 396 nm, 375 nm, 355 nm, and 341 nm, and emission wavelength peaks were observed at 422 nm and 434 nm (excitation wavelength: 375 nm). From the results in FIG. 21(B), for the solid thin film of PCcBCzPA, absorption peaks were observed at around 402 nm, 380 nm, 359 nm, 345 nm, and 305 nm, and an emission wavelength peak was observed at around 446 nm (excitation wavelength: 370 nm).

Note that PCcBCzPA was confirmed to emit blue light. The organic compound of one embodiment of the present invention, PCcBCzPA, can be used as a host for a light-emitting substance or a substance that emits fluorescence in the visible region. Furthermore, the thin film of PCcBCzPA was found to have a good film quality with little change in shape, hardly being aggregated even under air.

The HOMO level and the LUMO level of PCcBCzPA were calculated based on a cyclic voltammetry (CV) measurement. The calculation method is shown below.

An electrochemical analyzer (ALS model 600A or 600C, manufactured by BAS Inc.) was used as a measurement apparatus. To prepare a solution for the CV measurement, dehydrated dimethylformamide (DMF; produced by Sigma-Aldrich Inc., 99.8%, catalog No. 22705-6) was used as a solvent, tetra-n-butylammonium perchlorate (n-Bu$_4$NClO$_4$; produced by Tokyo Chemical Industry Co., Ltd., catalog No. T0836) as a supporting electrolyte was dissolved at a concentration of 100 mmol/L, and the object to be measured was also dissolved at a concentration of 2 mmol/L.

A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at room temperature (higher than or equal to 20° C. and lower than or equal to 25° C.).

In addition, the scan speed in the CV measurement was fixed to 0.1 V/sec, and an oxidation potential Ea [V] and a reduction potential Ec [V] with respect to the reference electrode were measured. Ea is an intermediate potential of an oxidation-reduction wave, and Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea, and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the HOMO level was found to be −5.64 eV in the measurement of the oxidation potential Ea[V] of PCcBCzPA. In contrast, the LUMO level was found to be −2.73 eV in the measurement of the reduction potential Ec[V]. In addition, when the oxidation-reduction wave was repeatedly measured and the waveform of the first cycle was compared with that in the hundredth cycle, 85% of the peak intensity was maintained in the Ea measurement, and 71% of the peak intensity was maintained in the Ec measurement; thus, resistance to oxidation and reduction of PCcBCzPA was found to be extremely high.

Example 5

Synthesis Example 4

In this example, a synthesis method of 7-[4-(10-phenyl-9-anthryl)phenyl]-9-(9-phenyl-9H-carbazol-2-yl)-7H-benzo[c]carbazole (abbreviation: PCcBCzPA-02), which is an organic compound of one embodiment of the present invention represented by the structural formula (253) of Embodiment 1, will be described. The structure of PCcBCzPA-02 is shown below.

[Chemical Formula 22]

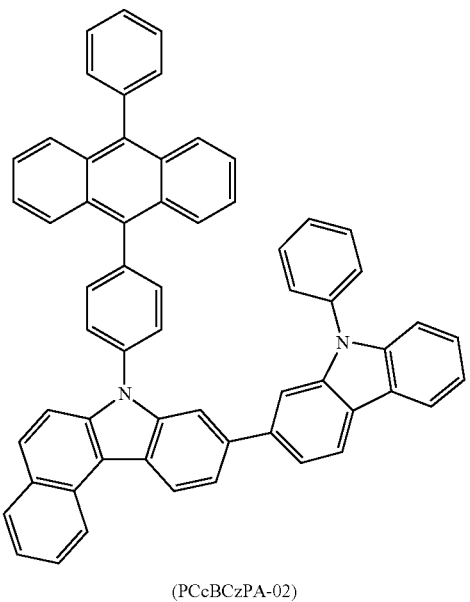

(253)

(PCcBCzPA-02)

Into a 100 mL three-neck flask were put 0.8 g (2.0 mmol) of 9-(4-bromophenyl)-10-phenylanthracene, 0.9 g (2.0 mmol) of 9-(9-phenyl-9H-carbazol-2-yl)-7H-benzo[c]carbazole, and 0.38 g (4.0 mmol) of sodium tert-butoxide, and the air in the flask was replaced with nitrogen. To this mixture were added 10 mL of xylene and 0.4 mL of a 10 wt % hexane solution of tri(tert-butyl)phosphine, and the mixture was degassed by being stirred under reduced pressure. To this mixture was added 58 mg (0.10 mmol) of bis(dibenzylideneacetone)palladium(0), and the mixture was refluxed at 150° C. for six hours under a nitrogen stream.

After the stirring, this mixture was filtered, and a solid was washed with water. The filtrate was washed with saturated saline, and the organic layer was dried with magnesium sulfate. This mixture was gravity-filtered, and the filtrate was concentrated. The obtained oily substance and solid were purified together by a silica gel column chromatography (toluene:hexane=1:2) and then were recrystallized with toluene/hexane, whereby 0.70 g of a white solid, which was the target substance, was obtained in a yield of 59%. The synthesis scheme of the above synthesis method is shown in the following formula (d).

[Chemical Formula 23]

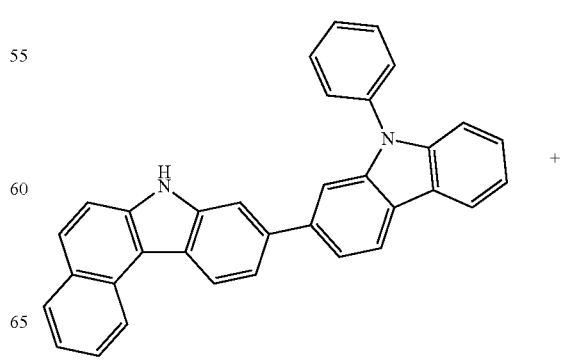

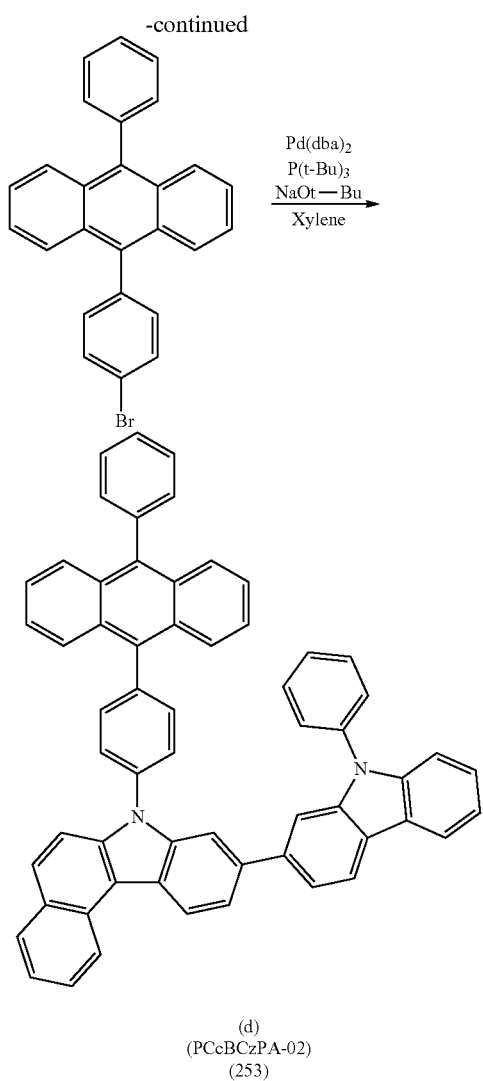

(d)
(PCcBCzPA-02)
(253)

By the train sublimation method, 0.50 g of the obtained white solid was sublimated and purified. The sublimation purification was performed under the condition of the pressure being 3.2×10⁻² Pa, by heating at 300° C. After the sublimation purification, 0.40 g of a yellow solid was obtained at a collection rate of 80%.

Figure 22A:
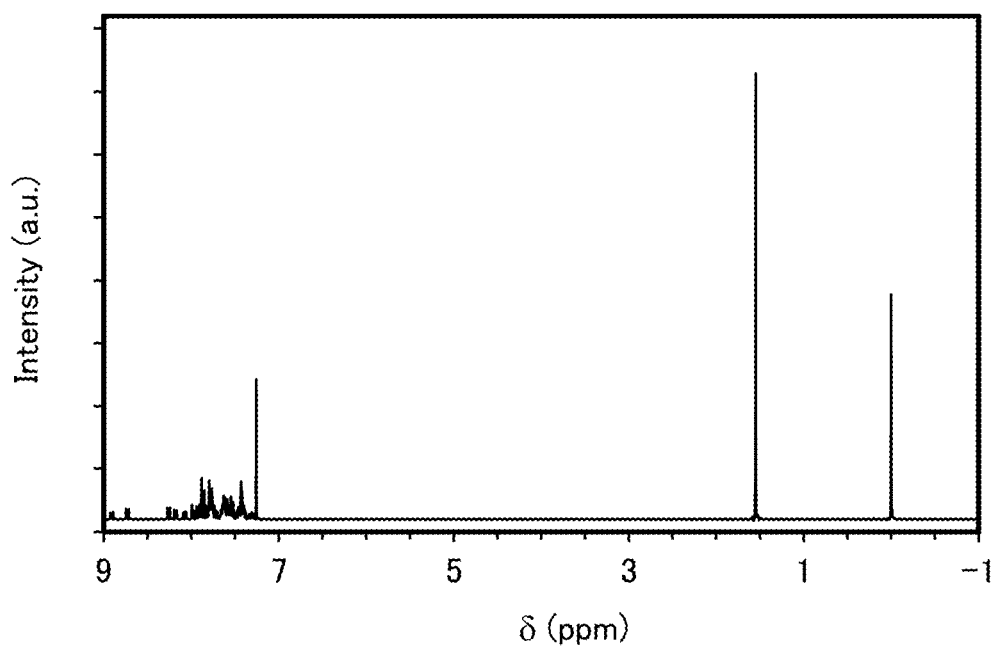
FIGS. 22A and 22B $^1$H-NMR charts of the organic compound represented by the structural formula (253).
Figure 22B:
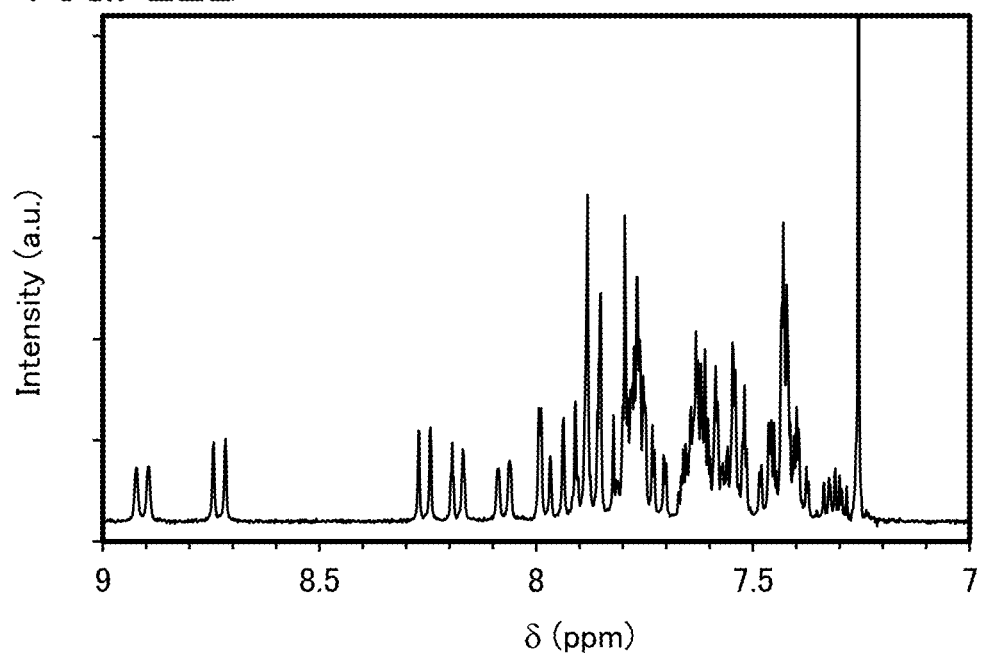

Analysis results of the obtained yellow solid by nuclear magnetic resonance (¹H-NMR) spectroscopy are shown below. In addition, ¹H-NMR charts are shown in FIGS. 22(A) and (B). Note that FIG. 22(B) is a chart showing an enlarged view of the range of 7.0 ppm to 9.0 ppm in FIG. 22(A). These results revealed that PCcBCzPA-02, which is the organic compound of one embodiment of the present invention represented by the above structural formula (253), was obtained in this example.

¹H NMR (CDCl₃, 300 MHz): δ=7.28-7.91 (m, 31H), 7.95 (d, J=9.3 Hz, 1H), 7.99 (d, J=1.5 Hz, 1H), 8.08 (d, J=7.8 Hz, 1H), 8.18 (d, J=7.5 Hz, 1H), 8.26 (d, J=7.8 Hz, 1H), 8.73 (d, J=8.1 Hz, 1H), 8.91 (d, J=8.7 Hz, 1H)

Next, the ultraviolet-visible absorption spectra (hereinafter, simply referred to as "absorption spectra") and emission spectra of a toluene solution and a solid thin film of PCcBCzPA-02 were measured. The solid thin film was fabricated over a quartz substrate by the vacuum evaporation method. For the measurement of the absorption spectra, spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance ($-\log_{10}$ [% T/(100−% R)]) obtained from a transmittance and a reflectance of the substrate and the thin film. Note that % T represents transmittance and % R represents reflectance. For the measurement of the emission spectrum, a fluorescence spectrophotometer (FS920 manufactured by Hamamatsu Photonics K.K.) was used.

Figure 23A:
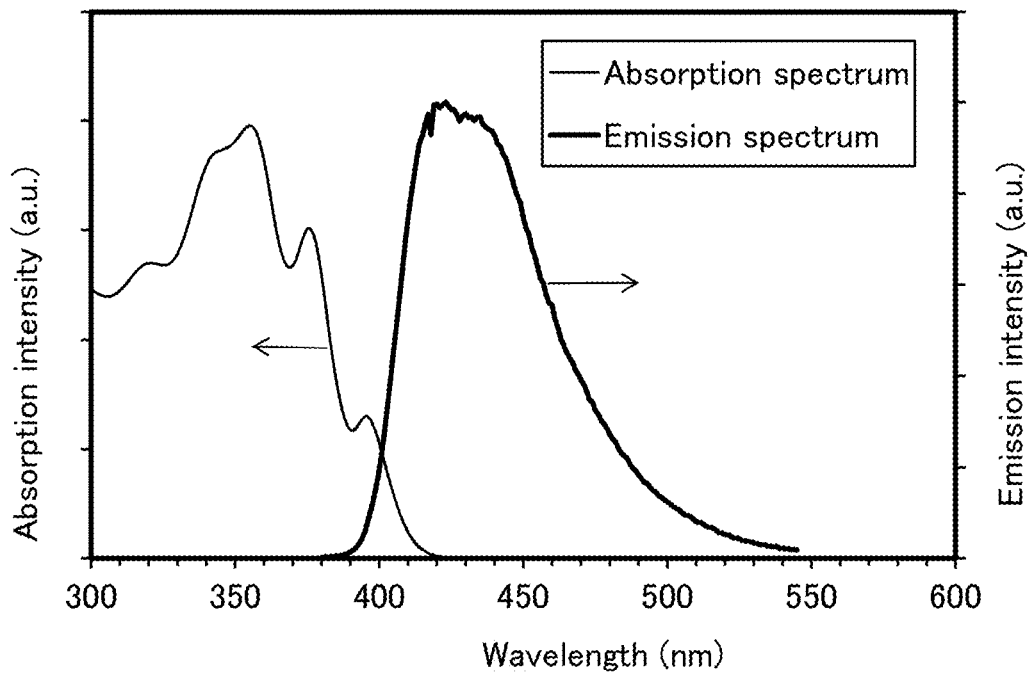
FIGS. 23A and 23B Ultraviolet-visible absorption spectra and emission spectra of the organic compound represented by the structural formula (253).
Figure 23B:
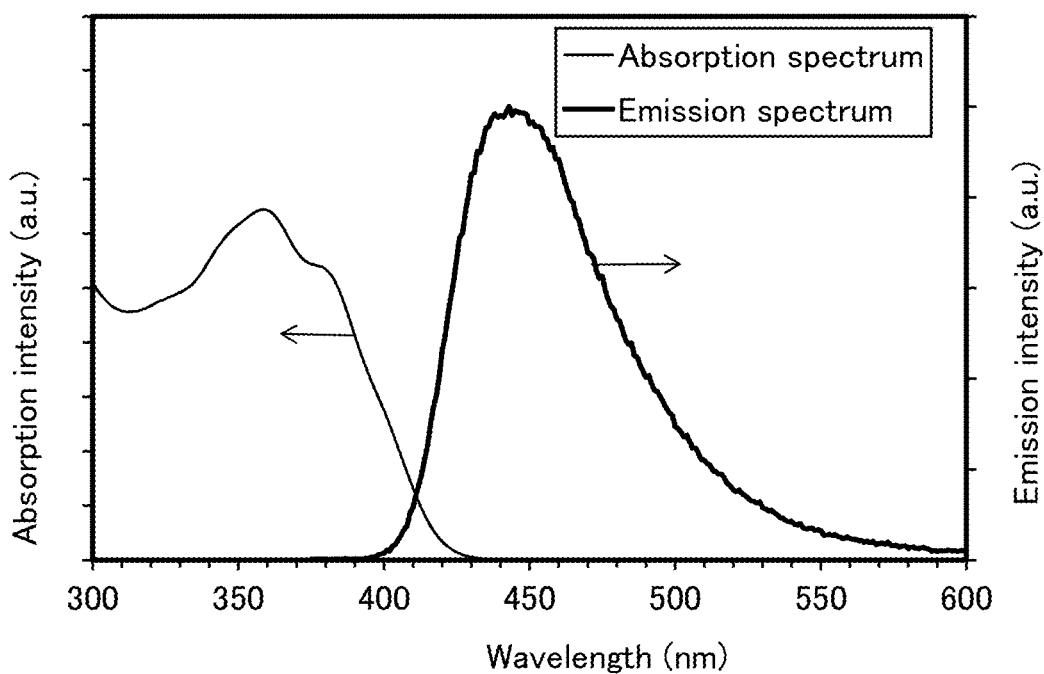

FIG. 23(A) shows the obtained measurement results of the absorption spectrum and the emission spectrum of the toluene solution. The horizontal axis represents wavelength and the vertical axes represent absorption intensity and emission intensity. FIG. 23(B) shows the measurement results of the absorption spectrum and the emission spectrum of the solid thin film. The horizontal axis represents wavelength and the vertical axes represent absorption intensity and emission intensity.

From the results in FIG. 23(A), for the toluene solution of PCcBCzPA-02, absorption peaks were observed at around 396 nm, 376 nm, 355 nm, 343 nm, and 320 nm, and emission wavelength peaks were observed at 422 nm (excitation wavelength: 376 nm). From the results in FIG. 23(B), for the solid thin film of PCcBCzPA-02, absorption peaks were observed at around 401 nm, 381 nm, 358 nm, 343 nm, and 323 nm, and an emission wavelength peak was observed at around 445 nm (excitation wavelength: 370 nm).

Note that PCcBCzPA-02 was confirmed to emit blue light. The compound of one embodiment of the present invention can be used as a host for a light-emitting substance or a substance that emits fluorescence in the visible region. Furthermore, the thin film of PCcBCzPA-02 was found to have a good film quality, hardly being aggregated even under air.

The HOMO level and the LUMO level of PCcBCzPA-02 were calculated based on a cyclic voltammetry (CV) measurement. The calculation method is shown below.

An electrochemical analyzer (ALS model 600A or 600C, manufactured by BAS Inc.) was used as a measurement apparatus. To prepare a solution for the CV measurement, dehydrated dimethylformamide (DMF; produced by Sigma-Aldrich Inc., 99.8%, catalog No. 22705-6) was used as a solvent, tetra-n-butylammonium perchlorate (n-Bu₄NClO₄; produced by Tokyo Chemical Industry Co., Ltd., catalog No. T0836) as a supporting electrolyte was dissolved at a concentration of 100 mmol/L, and the object to be measured was also dissolved at a concentration of 2 mmol/L.

A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag⁺ electrode (RE7 reference electrode for nonaqueous solvent, manufactured by BAS Inc.) was used as a reference electrode. Note that the measurement was performed at room temperature (higher than or equal to 20° C. and lower than or equal to 25° C.).

In addition, the scan speed in the CV measurement was fixed to 0.1 V/sec, and an oxidation potential Ea [V] and a reduction potential Ec [V] with respect to the reference electrode were measured. Ea is an intermediate potential of an oxidation-reduction wave, and Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea, and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the HOMO level was found to be −5.73 eV in the measurement of the oxidation potential Ea[V] of PCcBCzPA-02. In contrast, the LUMO level was found to be −2.74 eV in the measurement of the reduction potential Ec[V]. In addition, when the oxidation-reduction wave was repeatedly measured and the waveform of the first cycle was compared with that in the hundredth cycle, 78% of the peak intensity was maintained in the Ea measurement; thus, resistance to oxidation of PCcBCzPA-02 was found to be extremely high.

Example 6

Synthesis Example 5

In this example, a synthesis method of 9-[4-(10-phenyl-9-anthryl)phenyl]-2,9′-bi-9H-carbazole (abbreviation: CzCzPA-02), which is an organic compound of one embodiment of the present invention represented by the structural formula (220) of Embodiment 1, will be described. The structure of CzCzPA-02 is shown below.

[Chemical Formula 24]

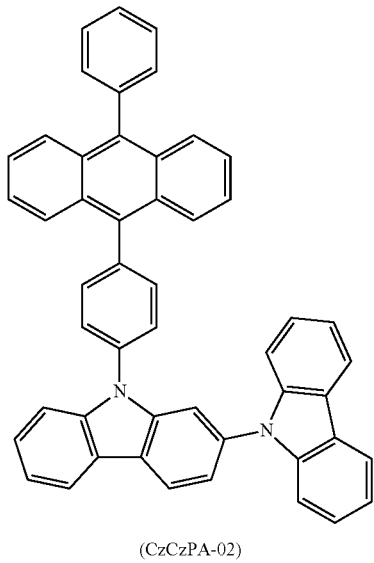

(CzCzPA-02) (220)

Into a 100 mL three-neck flask were put 0.65 g (1.6 mmol) of 9-(4-bromophenyl)-10-phenylanthracene, 0.54 g (1.6 mmol) of 2,9′-bi-9H-carbazole, and 0.32 g (3.3 mmol) of sodium tert-butoxide, and the air in the flask was replaced with nitrogen. To this mixture was added 10 mL of xylene, and the mixture was degassed by being stirred under reduced pressure. To this mixture, 0.4 mL of a 10 w % hexane solution of tri(tert-butyl)phosphine and 34 mg (59 μmol) of bis(dibenzylideneacetone)palladium(0) were added, and the mixture was stirred at 120° C. for six hours under a nitrogen stream.

After the stirring, the obtained mixture was washed with water and saturated saline, and the organic layer was dried with magnesium sulfate. This mixture was gravity-filtered, and the filtrate was concentrated. The obtained oily substance was purified by a silica gel column chromatography (toluene:hexane=1:2) and high performance liquid chromatography (developing solvent: chloroform), and then was recrystallized with toluene, whereby 0.66 g of a white solid, which was the target substance, was obtained in a yield of 63%. The synthesis scheme of the above synthesis method is shown in the following formula (e).

[Chemical Formula 25]

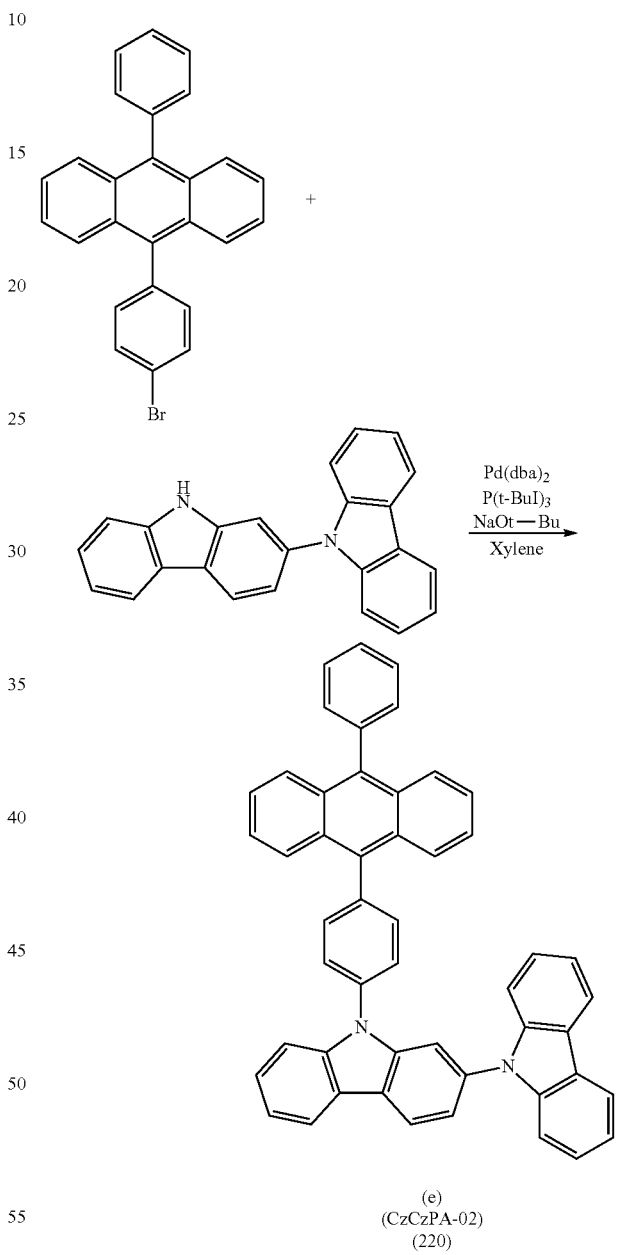

(e)
(CzCzPA-02)
(220)

By the train sublimation method, 0.69 g of the obtained white solid was sublimated and purified. The sublimation purification was performed under the conditions of the pressure being 3.4 Pa and the argon flow rate being 5.0 mL/min, by heating at 300° C. for 22 hours. After the sublimation purification, 0.61 g of a pale yellow solid was obtained at a collection rate of 88%.

Figure 24A:
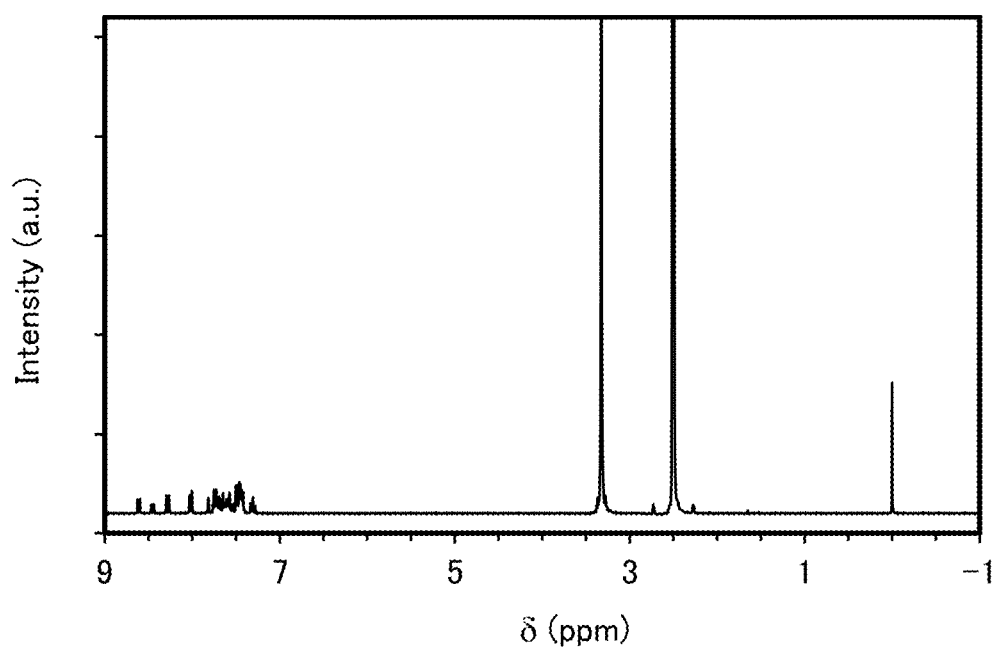
FIGS. 24A and 24B $^1$H-NMR charts of an organic compound represented by the structural formula (220).
Figure 24B:
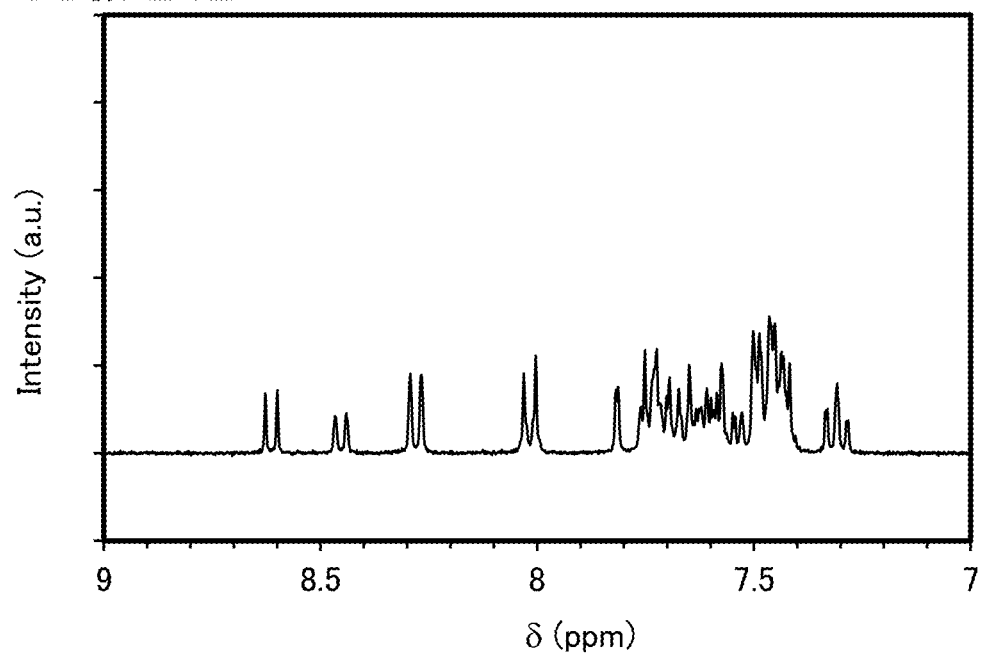

Analysis results of the obtained pale yellow solid by nuclear magnetic resonance ($^1$H-NMR) spectroscopy are shown below. In addition, $^1$H-NMR charts are shown in FIGS. 24(A) and (B). Note that FIG. 24(B) is a chart showing an enlarged view of the range of 7.0 ppm to 9.0 ppm in FIG. 24(A). These results revealed that CzCzPA-02, which is the organic compound of one embodiment of the present invention represented by the above structural formula (220), was obtained in this example.

$^1$H NMR (DMSO-d$_6$, 300 MHz): δ=7.31 (dt, J=0.9 Hz, 7.8 Hz, 2H), 7.40-7.76 (m, 23H), 7.82 (d, J=1.5 Hz, 1H), 8.02 (d, J=8.4 Hz, 2H), 8.28 (d, J=7.8 Hz, 2H), 8.45 (d, J=7.5 Hz, 1H), 8.61 (d, J=8.1 Hz, 1H)

Next, the ultraviolet-visible absorption spectra (absorption spectra) and emission spectra of a toluene solution and a solid thin film of CzCzPA-02 were measured. The solid thin film was fabricated over a quartz substrate by the vacuum evaporation method. For the measurement of the absorption spectra, spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance (–log$_{10}$ [% T/(100–% R)]) obtained from a transmittance and a reflectance of the substrate and the thin film. Note that % T represents transmittance and % R represents reflectance. For the measurement of the emission spectrum, a fluorescence spectrophotometer (FS920 manufactured by Hamamatsu Photonics K.K.) was used.

Figure 25A:
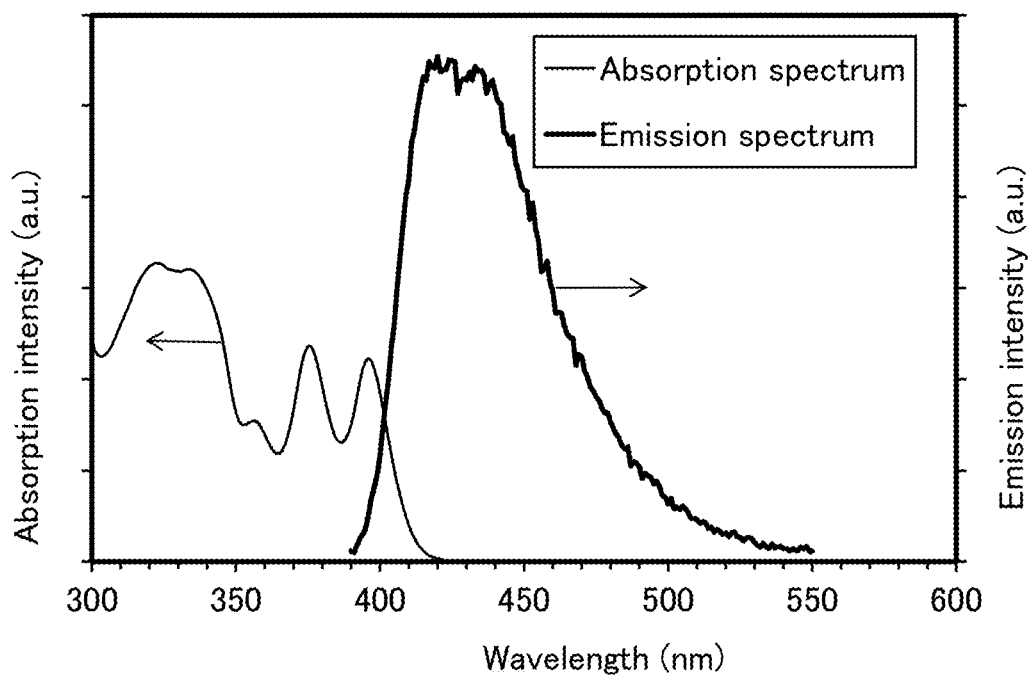
FIGS. 25A and 25B Ultraviolet-visible absorption spectra and emission spectra of the organic compound represented by the structural formula (220).
Figure 25B:
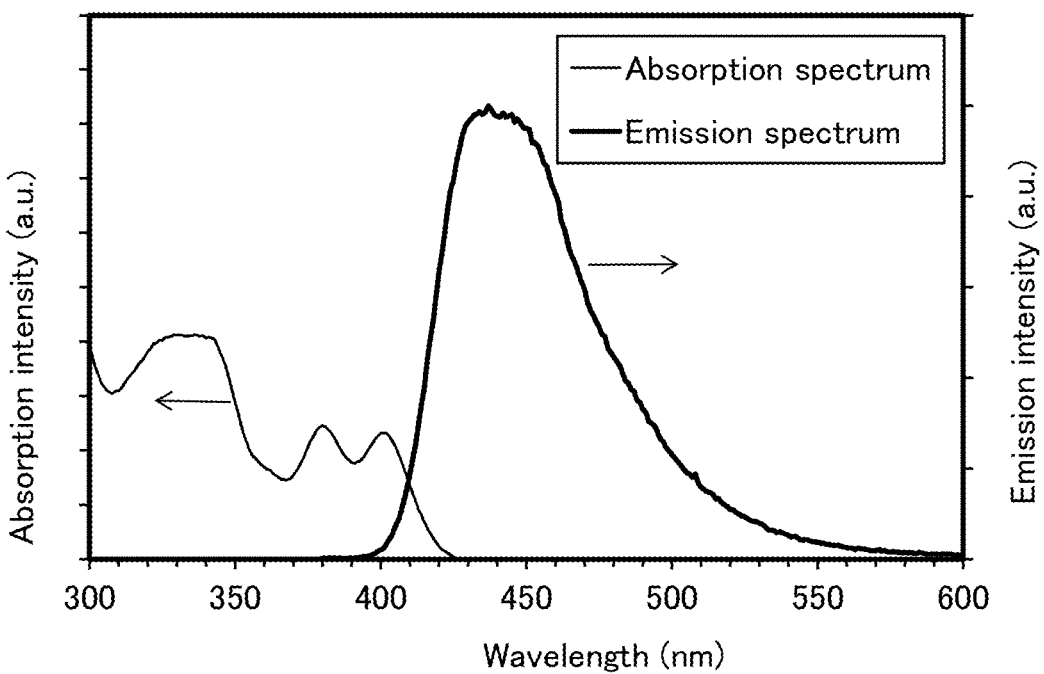
Figure 26:
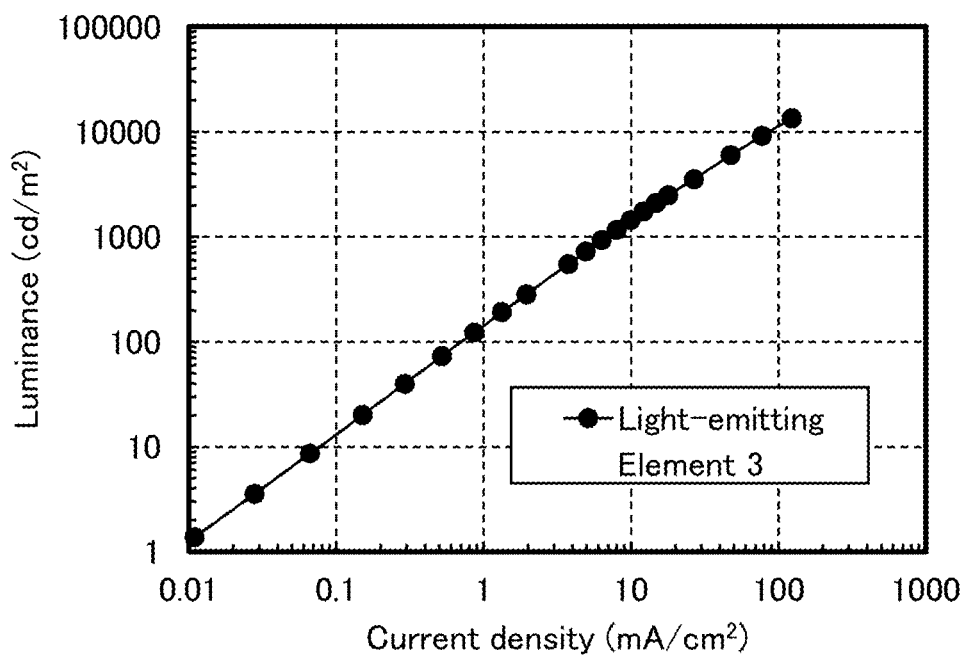
FIG. 26 A graph showing the current density-luminance characteristics of Light-emitting Element 3.
Figure 27:
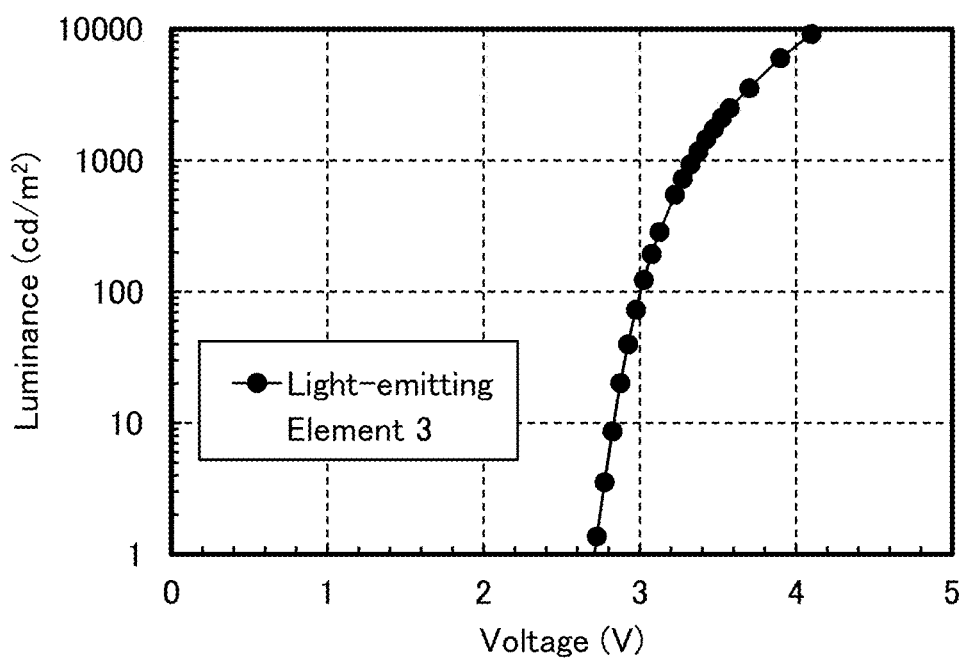
FIG. 27 A graph showing the voltage-luminance characteristics of Light-emitting Element 3.
Figure 28:
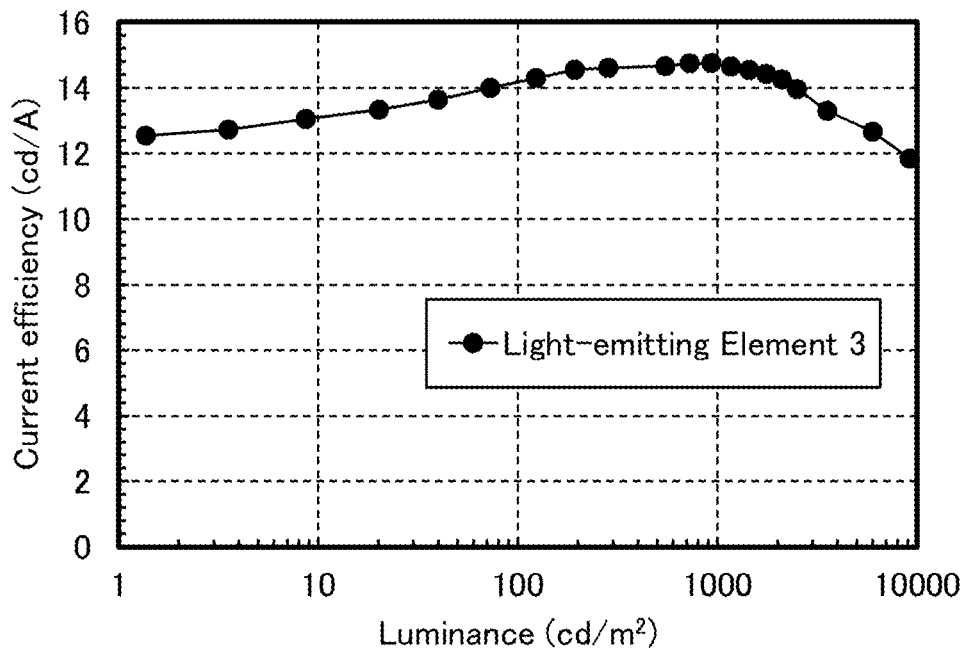
FIG. 28 A graph showing the luminance-current efficiency characteristics of Light-emitting Element 3.
Figure 29:
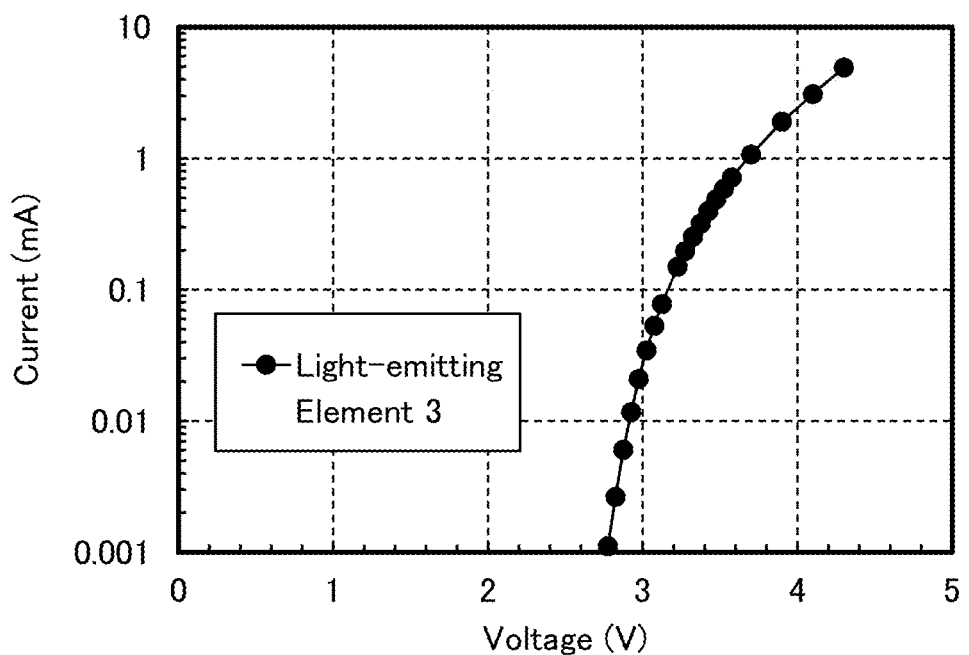
FIG. 29 A graph showing the voltage-current characteristics of Light-emitting Element 3.

FIG. 25(A) shows the obtained measurement results of the absorption spectrum and the emission spectrum of the toluene solution. The horizontal axis represents wavelength and the vertical axes represent absorption intensity and emission intensity. FIG. 25(B) shows the measurement results of the absorption spectrum and the emission spectrum of the solid thin film. The horizontal axis represents wavelength and the vertical axes represent absorption intensity and emission intensity.

From the results in FIG. 25(A), for the toluene solution of CzCzPA-02, absorption peaks were observed at around 396 nm, 376 nm, 356 nm, 334 nm, and 322 nm, and emission wavelength peaks were observed at 419 nm and 434 nm (excitation wavelength: 376 nm). From the results in FIG. 25(B), for the solid thin film of CzCzPA-02, absorption peaks were observed at around 402 nm, 380 nm, and 335 nm, and an emission wavelength peak was observed at around 440 nm (excitation wavelength: 345 nm).

Note that CzCzPA-02 was confirmed to emit blue light. The compound of one embodiment of the present invention can be used as a host for a light-emitting substance or a substance that emits fluorescence in the visible region. Furthermore, the thin film of CzCzPA-02 was found to have a good film quality, hardly being aggregated even under air.

Example 7

In this example, a light-emitting element 3 in which CzCzPA-02 (structure formula (220)) described in Example 6 was used for a light-emitting layer was fabricated as the light-emitting element of one embodiment of the present invention, and the results of the measurement of its characteristics are shown.

The element structure of the light-emitting element used in this example is similar to that in FIG. 13 mentioned in Example 3, and specific compositions of layers that constitute the element structure are as shown in Table 3. The chemical formulae of materials used in this example are shown below.

TABLE 3

| | First electrode | Hole-injection layer | Hole-transport layer | Light-emitting layer | Electron-transport layer | Electron-injection layer | Second electrode |
| --- | --- | --- | --- | --- | --- | --- | --- |
| Light-emitting element 3 | ITSO (70 nm) | PCPPn:MoOx (4:2, 10 nm) | PCPPn (30 nm) | * | CzCzPA-02 (15 nm) | NBphen (10 nm) | LiF (1 nm) | Al (200 nm) |

* CzCzPA-02: 1,6mMemFLPAPrn (1:0.03, 25 nm)

[Chemical Formulae 26]

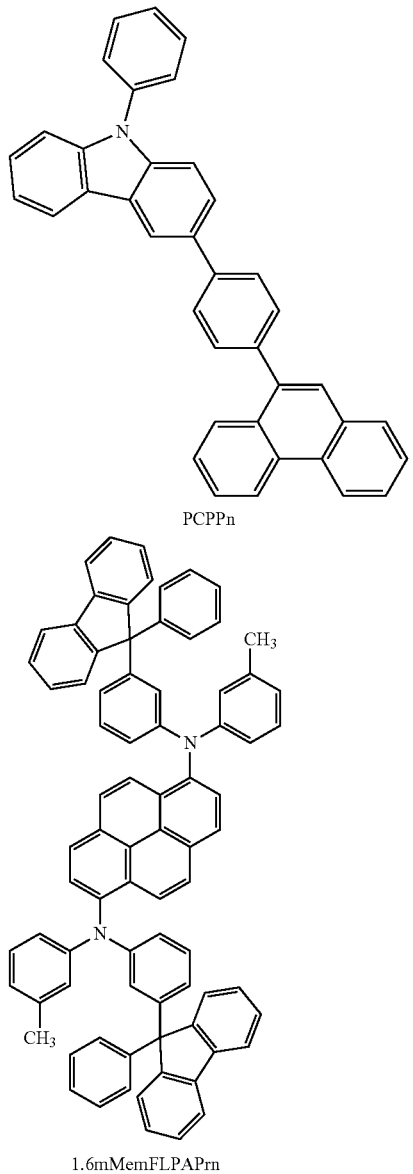

PCPPn 1,6mMemFLPAPrn

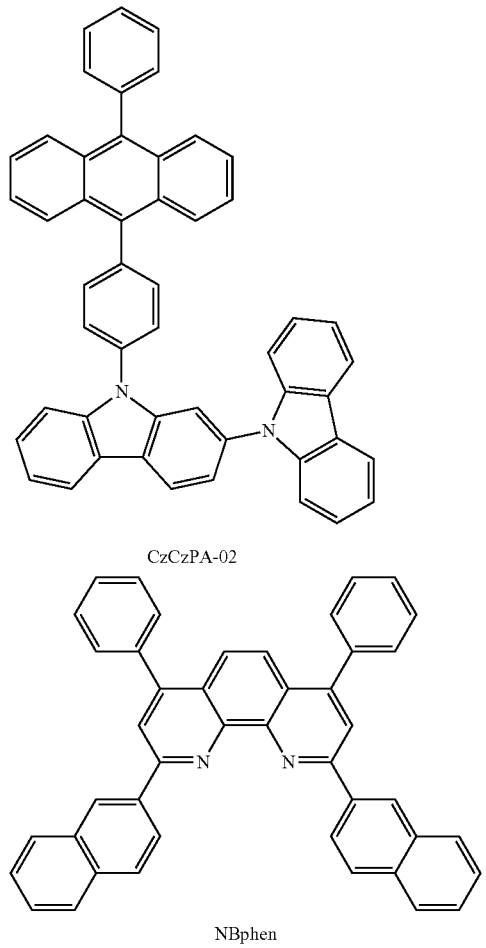

CzCzPA-02 (220)

NBphen

<<Operation Characteristics of Light-Emitting Element>>

Operation characteristics of the fabricated light-emitting element 3 were measured. Note that the measurement was performed at room temperature. The results are shown in FIG. 26 to FIG. 29.

The initial values of main characteristics of the light-emitting elements at around 1000 cd/m² are shown below in Table 4.

TABLE 4

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 3 | 3.3 | 0.25 | 6.3 | (0.14, 0.16) | 930 | 15 | 14 | 13 |

The above results show that the light-emitting element 3 fabricated in this example is driven at a low voltage, exhibits blue color with favorable chromaticity, and has high efficiency.

Figure 30:
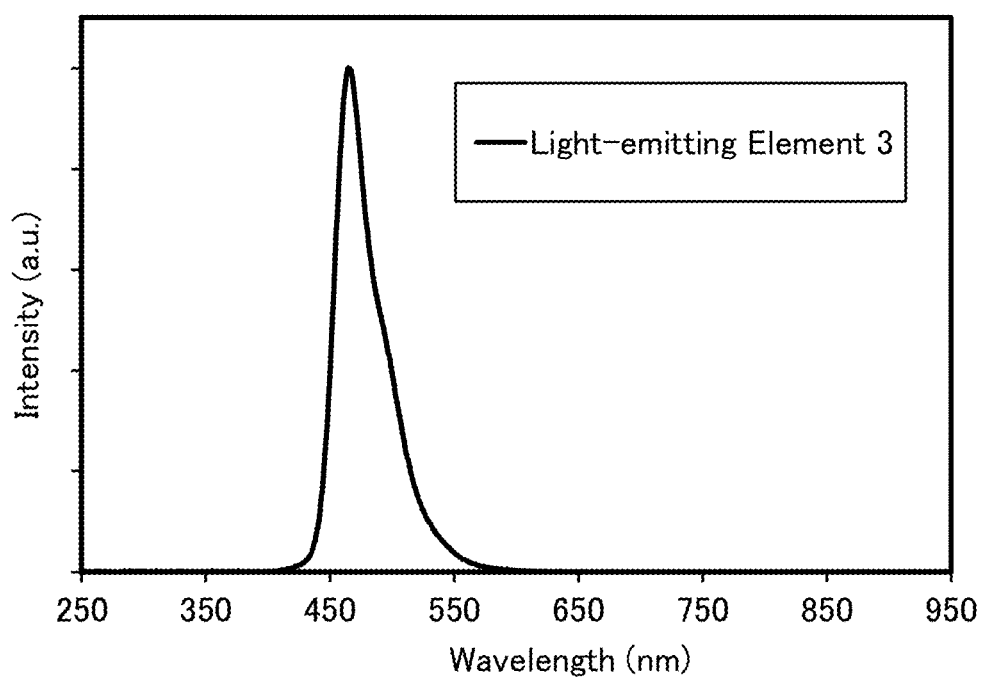
FIG. 30 A graph showing the emission spectrum of Light-emitting Element 3.

FIG. 30 shows emission spectrum in the case where current at a current density of 12.5 mA/cm² was supplied to the light-emitting element 3. As indicated by FIG. 30, the emission spectrum of the light-emitting element is derived from light emission of the light-emitting substance contained in the light-emitting layer 913.

Example 8

In this example, synthesis methods of 9-(9-phenyl-9H-carbazol-3-yl)-7H-benzo[c]carbazole (PCcBCz (structural formula (400)) and 9-(9-phenyl-9H-carbazol-2-yl)-7H-benzo[c]carbazole (PCcBCz-02 (structural formula 401)), which are used in the synthesis of PCcBCzPA (structural formula (252)) in Example 4 and the synthesis of PCcBCzPA-02 (structural formula 253)) in Example 5, respectively, will be described. The structures of PCcBCz and PCcBCz-02 are shown below.

[Chemical Formulae 27]

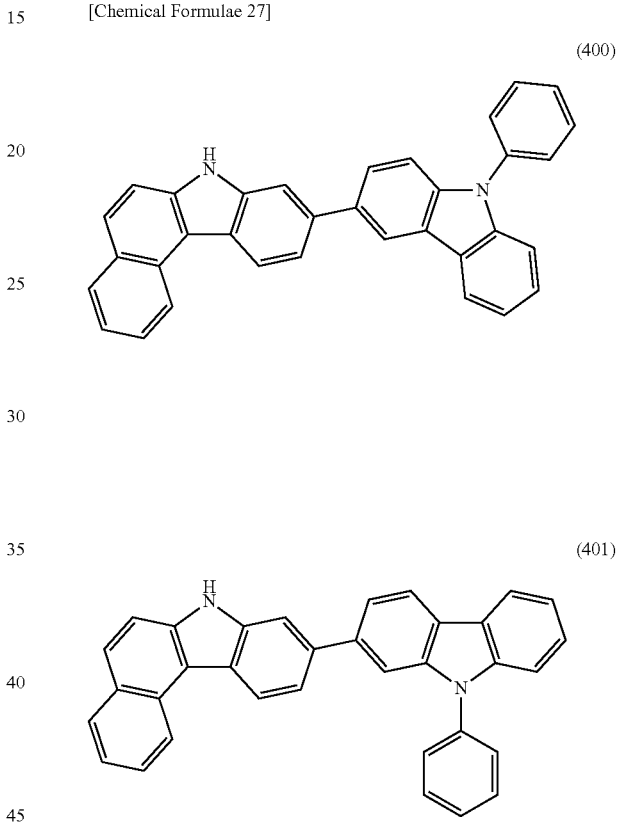

Step 1: Synthesis of 9-chloro-7H-benzo[c]carbazole

Into a 200 mL three-neck flask were put 2.9 g (10 mmol) of 1-(4-chlorophenyl)-2-nitronaphthalene, 11 g (40 mmol) of triphenylphosphine, and 50 mL of o-dichlorobenzene, and the mixture was stirred at 180° C. for 10 hours under a nitrogen stream. After the reaction, this mixture was purified by silica gel column chromatography (toluene:hexane=1:1) to give a solid. The obtained solid was washed with hexane to give 2.0 g of a white solid, which was the target substance, in a yield of 80%. The synthesis scheme of Step 1 is shown in the following formula (f-1).

[Chemical Formula 28]

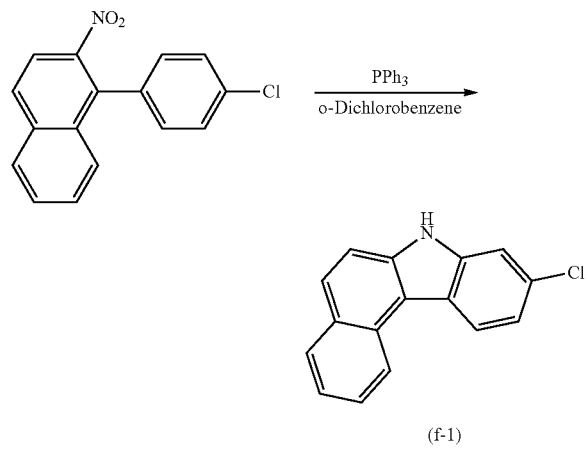

(f-1)

Figure 31A:
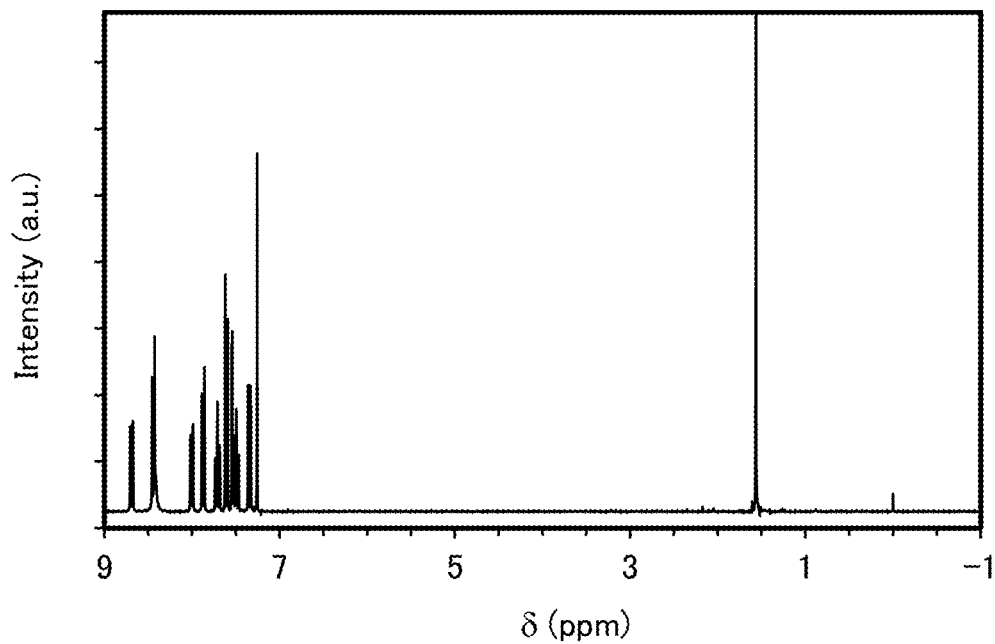
FIGS. 31A and 31B $^1$H-NMR charts of 9-chloro-7H-benzo[c]carbazole.
Figure 31B:
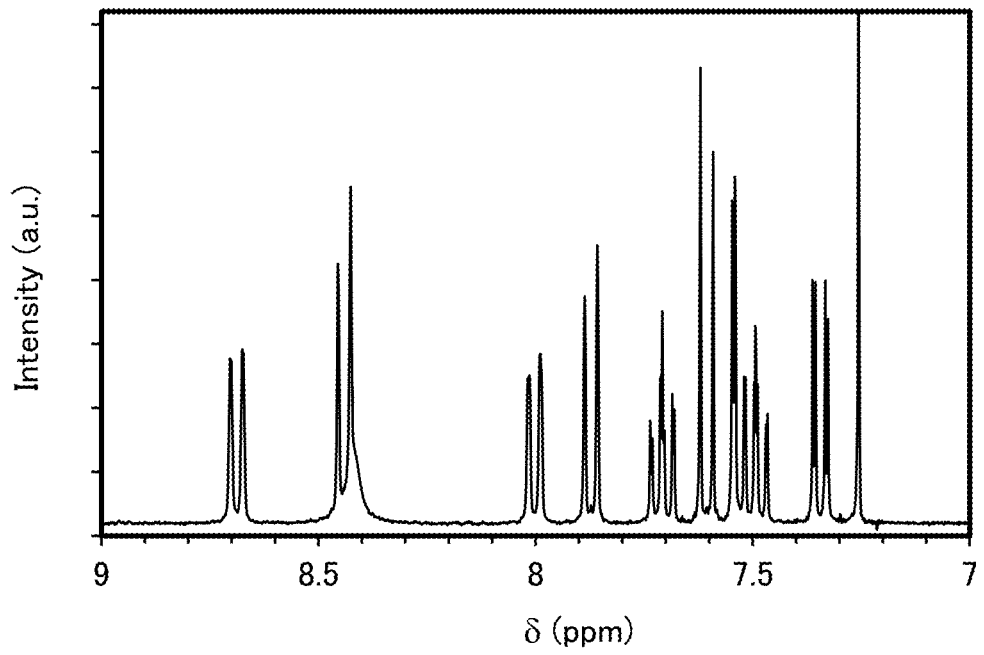

Analysis results of the obtained white solid by nuclear magnetic resonance ($^1$H-NMR) spectroscopy are shown below. In addition, $^1$H-NMR charts are shown in FIGS. 31(A) and (B). Note that FIG. 31(B) is a chart showing an enlarged view of the range of 7.0 ppm to 9.0 ppm in FIG. 31(A). These results revealed that 9-chloro-7H-benzo[c]carbazole, which was the target substance in the above formula (f-1), was obtained.

$^1$H NMR (CDCl$_3$, 300 MHz): δ=7.34 (dd, J1=9.0 Hz, J2=1.8 Hz, 1H), 7.47-7.52 (m, 1H), 7.54 (d, J=2.1 Hz, 1H), 7.61 (d, J=8.7 Hz, 1H), 7.68-7.74 (m, 1H), 7.87 (d, J=8.7 Hz, 1H), 8.00 (d, J=7.8 Hz, 1H), 8.43-8.46 (m, 2H), 8.69 (d, J=8.4 Hz, 1H)

Step 2-1: Synthesis of PCcBCz

In Step 2-1, a method for synthesizing PCcBCz with the use of 9-chloro-7H-benzo[c]carbazole, which was synthesized in Step 1 above, will be described.

Into a 200 mL three-three flask were put 1.8 g (7.1 mmol) of 9-chloro-7H-benzo[c]carbazole, which was synthesized in Step 1 above, 2.2 g (7.1 mmol) of 9-phenyl-9H-carbazole-3-boronic acid, 0.25 g (0.70 mmol) of di(1-adamantyl)-n-butylphosphine, 4.6 g (22 mmol) of tripotassium phosphate, 1.6 g (22 mmol) of tert-butyl alcohol, and 35 mL of diethylene glycol dimethyl ether, and the mixture was degassed by being stirred while the pressure was reduced. To this mixture was added 79 mg (0.35 mmol) of palladium(II) acetate, and the mixture was stirred under a nitrogen stream at 160° C. for 13 hours. After the reaction, a solid was removed from this mixture by suction filtration, and the obtained filtrate was purified by silica gel column chromatography (chloroform:hexane=1:2) to give a solid. The obtained solid was washed with hexane, so that 2.0 g of a pale brown solid, which was the target substance, was obtained in a yield of 61%. The synthesis scheme of the above synthesis method is shown in the following formula (f-2-1).

[Chemical Formula 29]

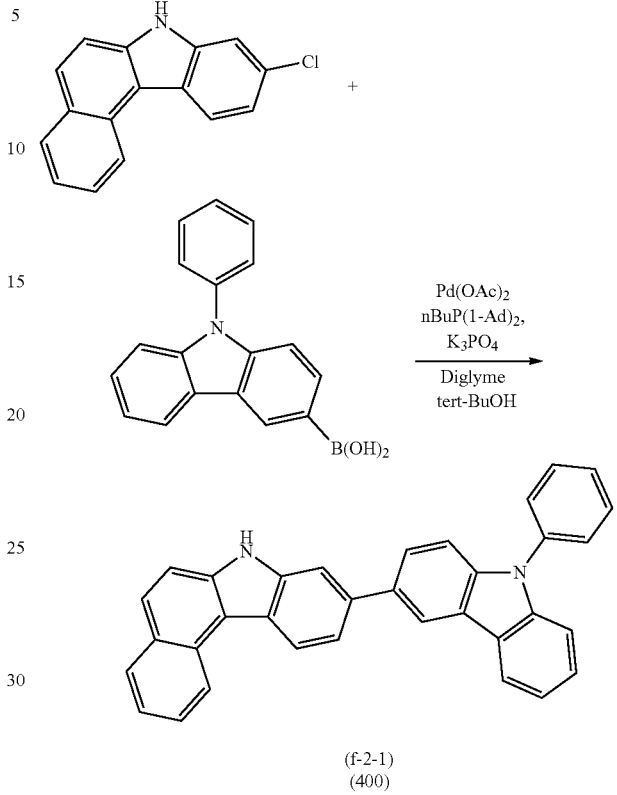

(f-2-1)
(400)

Figure 32A:
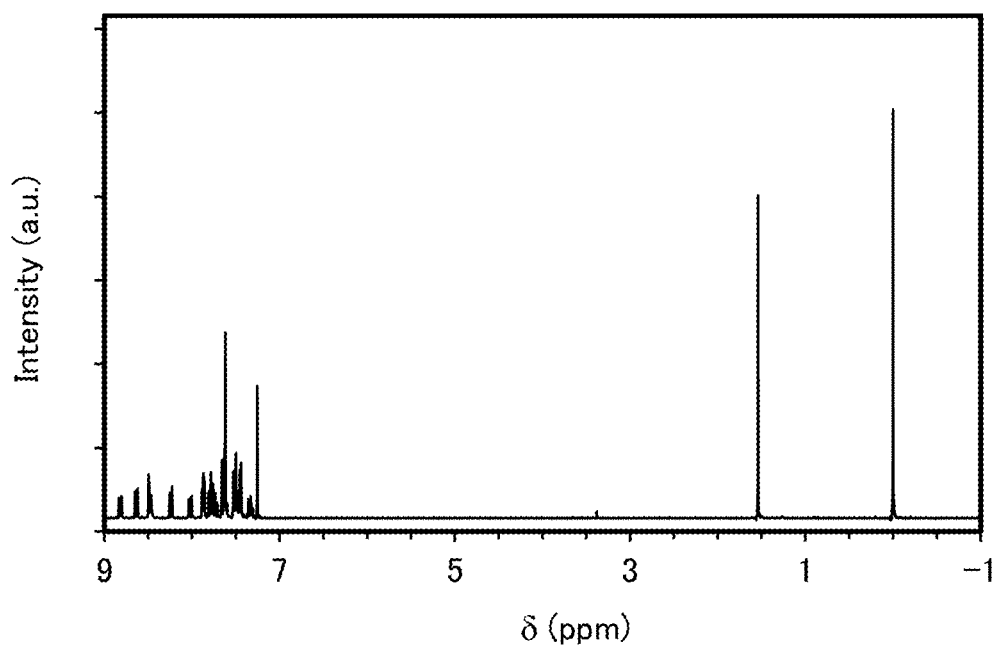
FIGS. 32A and 32B $^1$H-NMR charts of PCcBCz.
Figure 32B:
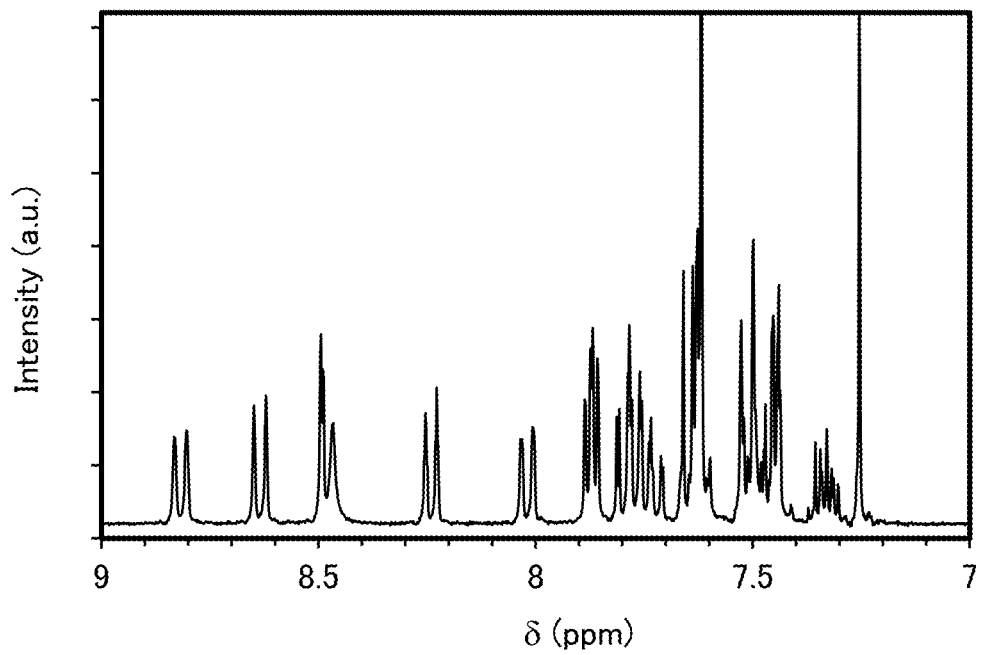

Analysis results of the obtained pale brown solid by nuclear magnetic resonance ($^1$H-NMR) spectroscopy are shown below. In addition, $^1$H-NMR charts are shown in FIGS. 32(A) and (B). Note that FIG. 32(B) is a chart showing an enlarged view of the range of 7.0 ppm to 9.0 ppm in FIG. 32(A). These results revealed that PCcBCz (structural formula (400)), which was the target substance in the above formula (f-2-1), was obtained.

$^1$H NMR (CDCl$_3$, 300 MHz): δ=7.30-7.36 (m, 1H), 7.44-7.53 (m, 5H), 7.60-7.66 (m, 5H), 7.71-7.81 (m, 3H), 7.86-7.89 (m, 2H), 8.02 (d, J=7.8 Hz, 1H), 8.23-8.25 (m, 1H), 8.47-8.49 (m, 2H), 8.63 (d, J=8.1 Hz, 1H), 8.82 (d, J=8.4 Hz, 1H)

Step 2-2: Synthesis of PCcBCz-02

In Step 2-2, a method for synthesizing PCcBCz-02 with the use of 9-chloro-7H-benzo[c]carbazole, which was synthesized in Step 1 above, will be described.

Into a 200 mL three-three flask were put 1.0 g (4.0 mmol) of 9-chloro-7H-benzo[c]carbazole, which was synthesized in Step 1 above, 1.2 g (4.0 mmol) of 9-phenyl-9H-carbazole-2-boronic acid, 29 mg (0.080 mmol) of di(1-adamantyl)-n-butylphosphine, 2.5 g (12 mmol) of tripotassium phosphate, 0.90 g (12 mmol) of tert-butyl alcohol, and 20 mL of diethylene glycol dimethyl ether, and the mixture was degassed by being stirred while the pressure was reduced. To this mixture was added 9.0 mg (0.040 mmol) of palladium(II) acetate, and the mixture was stirred under a nitrogen stream at 120° C. for 20 hours. After the reaction, a solid was removed from this mixture by suction filtration, and the obtained filtrate was purified by silica gel column chromatography (toluene:hexane=1:2) to give a solid. The obtained solid was washed with hexane, so that 0.91 g of a pale brown solid, which was the target substance, was obtained in a yield of 50%. The synthesis scheme of the above synthesis method is shown in the following formula (f-2-2).

[Chemical Formula 30]

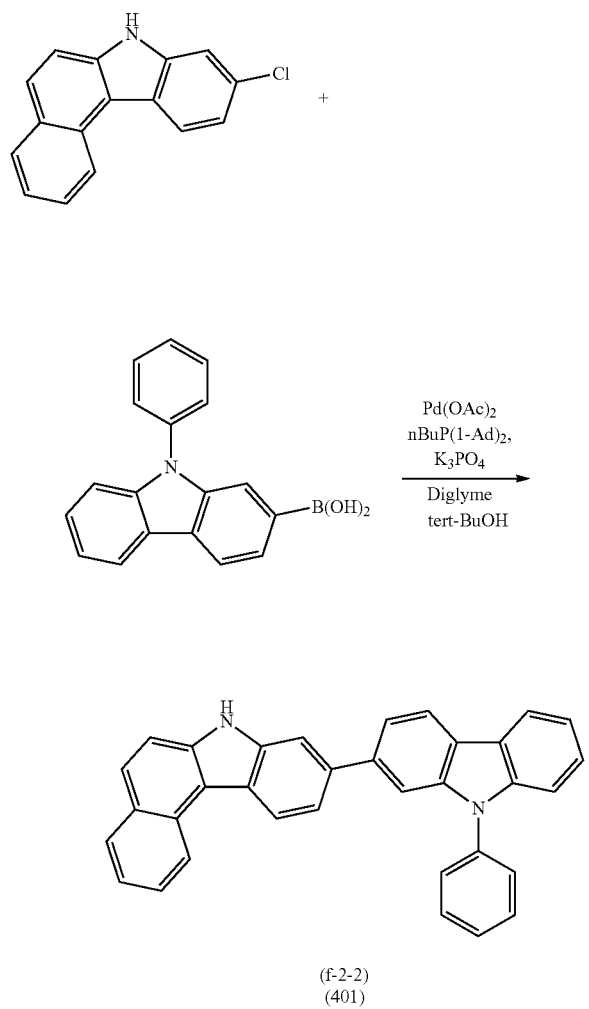

(f-2-2)
(401)

Figure 33A:
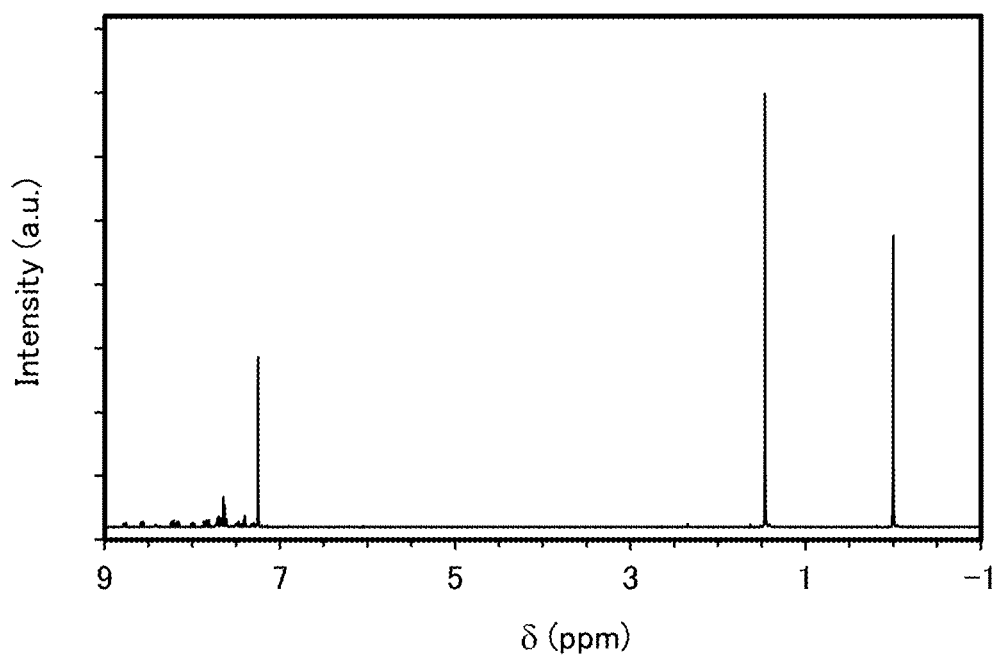
FIGS. 33A and 33B $^1$H-NMR chart of PCcBCz-02.
Figure 33B:
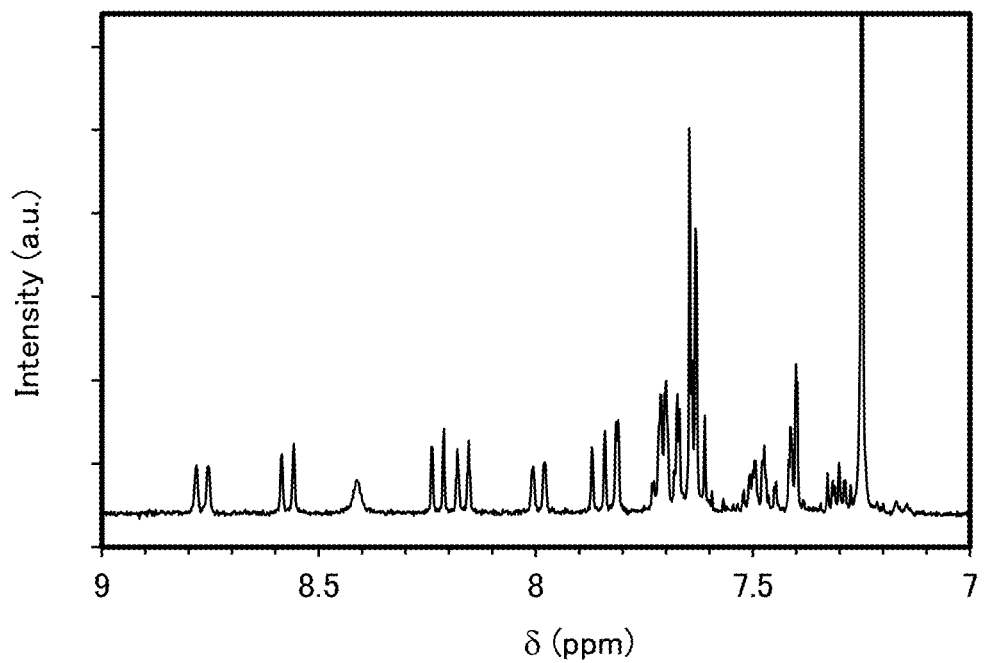

Analysis results of the obtained pale brown solid by nuclear magnetic resonance ($^1$H-NMR) spectroscopy are shown below. In addition, $^1$H-NMR charts are shown in FIGS. 33(A) and (B). Note that FIG. 33(B) is a chart showing an enlarged view of the range of 7.0 ppm to 9.0 ppm in FIG. 33(A). These results revealed that PCcBCz-02 (structural formula (401)), which was the target substance, was obtained.

$^1$H NMR (CDCl$_3$, 300 MHz): δ=7.27-7.33 (m, 1H), 7.40-7.52 (m, 4H), 7.61-7.73 (m, 9H), 7.81 (d, J=1.5 Hz, 1H), 7.86 (d, J=8.7 Hz, 1H), 7.99 (d, J=8.4 Hz, 1H), 8.17 (d, J=7.8 Hz, 1H), 8.23 (d, J=9.0 Hz, 1H), 8.41 (s, 1H), 8.57 (d, J=8.4 Hz, 1H), 8.77 (d, J=7.8 Hz, 1H)

DESCRIPTION OF NUMERALS 101 first electrode
102 second electrode
103 EL layer
103a, 103b EL layer
104 charge-generation layer
111, 111a, 111b hole-injection layer
112, 112a, 112b hole-transport layer
113, 113a, 113b light-emitting layer
114, 114a, 114b electron-transport layer
115, 115a, 115b electron-injection layer
201 first substrate
202 transistor (FET)
203R, 203G, 203B, 203W light-emitting element
204 EL layer
205 second substrate
206R, 206G, 206B color filter
206W, 206G', 206B' color filter
207 first electrode
208 second electrode
209 black layer (black matrix)
210R, 210G conductive layer
301 first substrate
302 pixel portion
303 driver circuit portion (source line driver circuit)
304a, 304b driver circuit portion (gate line driver circuit)
305 sealant
306 second substrate
307 lead wiring
308 FPC
309 FET
310 FET
311 FET
312 FET
313 first electrode
314 insulator
315 EL layer
316 second electrode
317 light-emitting element
318 space
900 substrate
901 first electrode
902 EL layer
903 second electrode
911 hole-injection layer
912 hole-transport layer
913 light-emitting layer
914 electron-transport layer
915 electron-injection layer
4000 lighting device
4001 substrate
4002 light-emitting element
4003 substrate
4004 first electrode
4005 EL layer
4006 second electrode
4007 electrode
4008 electrode
4009 auxiliary wiring
4010 insulating layer
4011 sealing substrate
4012 sealant
4013 desiccant
4015 diffusion plate
4100 lighting device
4200 lighting device 4201 substrate
4202 light-emitting element
4204 first electrode
4205 EL layer
4206 second electrode
4207 electrode
4208 electrode
4209 auxiliary wiring
4210 insulating layer
4211 sealing substrate
4212 sealant
4213 barrier film
4214 planarization film
4215 diffusion plate
4300 lighting device
5101 light
5102 wheel
5103 door
5104 display portion
5105 steering wheel
5106 shifter
5107 seat
5108 inner rear view mirror
7000 housing
7001 display portion
7002 second display portion
7003 speaker
7004 LED lamp
7005 operation key
7006 connection terminal
7007 sensor
7008 microphone
7009 switch
7010 infrared port
7011 recording medium reading portion
7012 support portion
7013 earphone
7014 antenna
7015 shutter button
7016 image receiving portion
7018 stand
7019 microphone
7020 camera
7021 external connection portion
7022, 7023 operation button
7024 connection terminal
7025 band
7026 clasp
7027 icon indicating time
7028 another icon
8001 lighting device
8002 lighting device
8003 lighting device
8004 lighting device
9310 portable information terminal
9311 display portion
9312 display region
9313 hinge
9315 housing

The invention claimed is:

1. An organic compound represented by a general formula (G1),

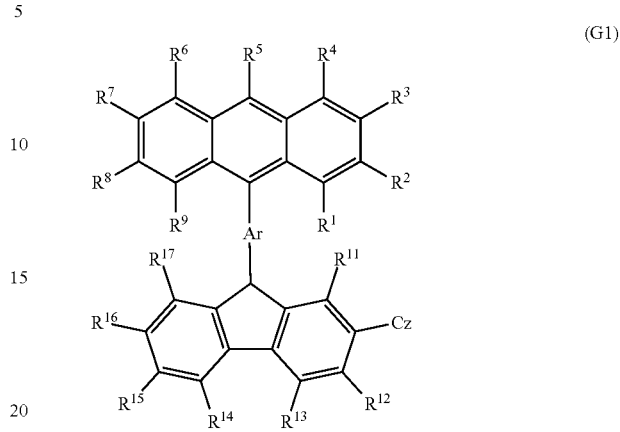

wherein Ar represents a substituted or unsubstituted arylene group having 6 to 13 carbon atoms,
wherein Cz represents a substituted or unsubstituted carbazole skeleton,
wherein each of $R^1$ to $R^4$, $R^6$ to $R^9$, $R^{11}$, $R^{13}$, $R^{14}$ and $R^{17}$ independently represents any of hydrogen, a substituted or unsubstituted alkyl group having 1 to 6 carbon atoms, a substituted or unsubstituted cycloalkyl group having 3 to 6 carbon atoms, or a substituted or unsubstituted aryl group having 6 to 13 carbon atoms,
wherein $R^5$ represents a substituted or unsubstituted aryl group having 6 to 13 carbon atoms, and
wherein each of $R^{12}$, $R^{15}$, and $R^{16}$ independently represents any of hydrogen, a substituted or unsubstituted alkyl group having 1 to 6 carbon atoms, or a substituted or unsubstituted cycloalkyl group having 3 to 6 carbon atoms.

2. The organic compound according to claim 1, wherein a bonding position of Cz bonded to the carbazole skeleton in the general formula (G1) is a 9-position, 3-position, or 2-position of the carbazole skeleton represented by Cz.

3. The organic compound according to claim 1, wherein Ar in the general formula (G1) is a substituted or unsubstituted phenylene group or a substituted or unsubstituted biphenyldiyl group.

4. The organic compound according to claim 1,
wherein the arylene group of Ar in the general formula (G1) has substituents, and
wherein the substituents are bonded to each other to form a ring.

5. A light-emitting element comprising the organic compound according to claim 1.

6. A light-emitting element comprising an EL layer between a pair of electrodes, the EL layer comprising the organic compound according to claim 1.

7. A light-emitting element comprising an EL layer between a pair of electrodes, the EL layer comprising a light-emitting layer,
wherein the light-emitting layer comprises the organic compound according to claim 1.

8. A light-emitting device comprising:
the light-emitting element according to claim 5; and
at least one of a transistor or a substrate.

9. An organic compound represented by a structural formula (200), a structural formula (220), or a structural formula (221), (200)

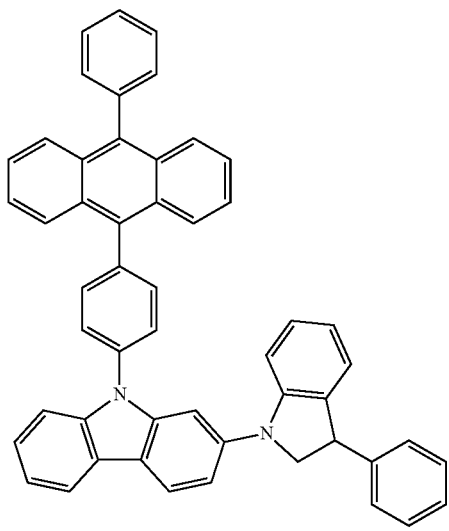

(221)

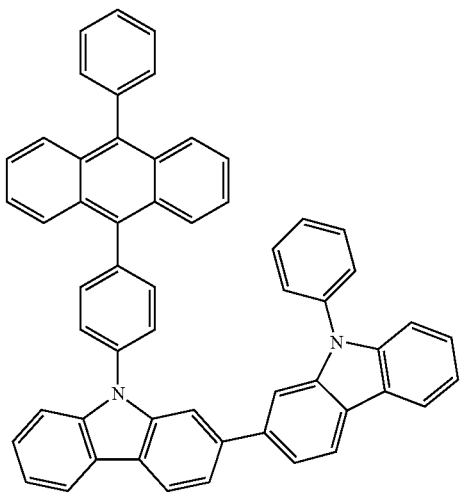

(220)

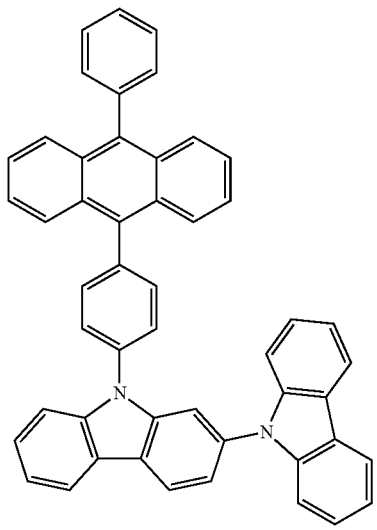

10. A light-emitting element comprising the organic compound according to claim 9.

11. A light-emitting element comprising an EL layer between a pair of electrodes, the EL layer comprising the organic compound according to claim 9.

12. A light-emitting element comprising an EL layer between a pair of electrodes, the EL layer comprising a light-emitting layer,
wherein the light-emitting layer comprises the organic compound according to claim 9.

13. A light-emitting device comprising:
the light-emitting element according to claim 10; and
at least one of a transistor or a substrate.

* * * * *